(12) United States Patent
Gai et al.

(10) Patent No.: US 8,361,958 B2
(45) Date of Patent: Jan. 29, 2013

(54) OXIMYL HCV SERINE PROTEASE INHIBITORS

(75) Inventors: Yonghua Gai, North Grafton, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 802 days.

(21) Appl. No.: 12/328,433

(22) Filed: Dec. 4, 2008

(65) Prior Publication Data

US 2009/0155210 A1 Jun. 18, 2009

(51) Int. Cl.
*A61K 38/00* (2006.01)

(52) U.S. Cl. ......................................................... 514/3.7

(58) Field of Classification Search ........................ None
See application file for complete search history.

(56) References Cited

U.S. PATENT DOCUMENTS

| | | | |
|---|---|---|---|
| 6,323,180 B1 | 11/2001 | Linas-Brunet et al. |
| 6,995,174 B2 | 2/2006 | Wang et al. |
| 7,132,504 B2 | 11/2006 | Scola et al. |
| 7,135,462 B2 | 11/2006 | Scola et al. |
| 7,273,851 B2 | 9/2007 | Miao et al. |
| 7,728,148 B2 | 6/2010 | Sun et al. |
| 2005/0261200 A1 | 11/2005 | Miao et al. |
| 2007/0281884 A1 | 12/2007 | Sun et al. |
| 2007/0281885 A1 | 12/2007 | Sun et al. |
| 2008/0038225 A1 | 2/2008 | Sun et al. |
| 2008/0125444 A1 | 5/2008 | Sun et al. |
| 2008/0181868 A1 | 7/2008 | Sun et al. |
| 2008/0187516 A1 | 8/2008 | Sun et al. |
| 2008/0267917 A1 | 10/2008 | Niu et al. |
| 2008/0274082 A1 | 11/2008 | Gai et al. |
| 2008/0287449 A1 | 11/2008 | Niu et al. |
| 2008/0292587 A1 | 11/2008 | Sun et al. |
| 2009/0175822 A1 | 7/2009 | Moore et al. |
| 2009/0191153 A1 | 7/2009 | Sun et al. |
| 2009/0197888 A1 | 8/2009 | Gai et al. |
| 2009/0202485 A1 | 8/2009 | Gai et al. |
| 2009/0202486 A1 | 8/2009 | Gai et al. |

FOREIGN PATENT DOCUMENTS

| | | |
|---|---|---|
| WO | 2007146695 A1 | 12/2007 |
| WO | 2009053828 A2 | 4/2009 |

OTHER PUBLICATIONS

Han, H.-K.. AAPS Pharmsci. (2000) 2(1), article 6, pp. 1-11.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Muller, Christa E. "Prodrug Approaches for Enhancing the Bioavailability of Drugs with Low Solubility," Chemistry & Biodiversity, vol. 6 (2009), pp. 2071-2083.*
Singh,Yashveer et al, "Recent Trends in Targeted Anticancer Prodrug and Conjugate," DesignCurr Med Chem. 2008 ; 15(18): 1802-1826.*
Ettmayer P. et al. J. Med. Chem. (2004) 47(10), pp. 2393-2404.*
Testa. Biochem. Pharm. (2004) 68, pp. 2097-2106.*
U.S. Appl. No. 12/357,805, Gai et al., co-pending application.
U.S. Appl. No. 12/357,854, Gai et al., co-pending application.
U.S. Appl. No. 12/324,071, Moore et al., co-pending application.
U.S. Appl. No. 12/327,453, Sun et al., co-pending application.
U.S. Appl. No. 12/328,628, Gai et al., co-pending application.
Dorwald, F.Z., Side Reactions in Organic Synthesis, Wiley-VCH, Weinheim, p. IX of Preface, 2005.
J. R. Herr, "A Whirlwind Tour of Current Mitsunobu Chemistry", Albany Molecular Research Inc., Technical Report, 1999, vol. 3, No. 19, pp. 1-36 (especially pp. 11-12).
International Search Report for PCT/US08/85524, dated Jun. 3, 2009.

* cited by examiner

*Primary Examiner* — Cecilia J Tsang
*Assistant Examiner* — Thomas Heard
(74) *Attorney, Agent, or Firm* — Edgar W. Harlan; Carolyn S. Elmore, Esq.; Elmore Patent Law Group, P.C.

(57) ABSTRACT

The present invention discloses compounds of formula I or pharmaceutically acceptable salts, esters, or prodrugs thereof:

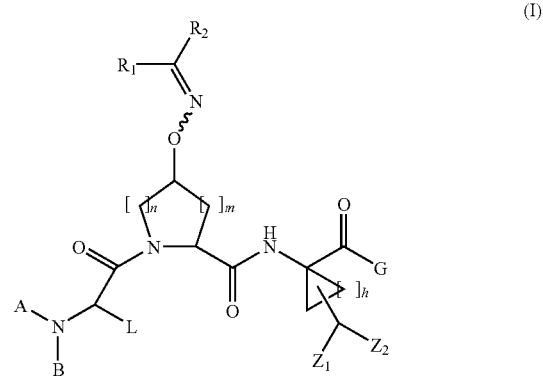

(I)

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

26 Claims, No Drawings

```
                        SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Forward Primer

<400> SEQUENCE: 1
gctgcggcct gtcgagct                                              18

<210> SEQ ID NO 2
<211> LENGTH: 19
<212> TYPE: DNA
<213> ORGANISM: Artificial Sequence
<220> FEATURE:
<223> OTHER INFORMATION: Reverse Primer

<400> SEQUENCE: 2
caaggtcgtc tccgcatac                                             19

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
cgaagctcca ggactgcacg atgct                                      25
```

US 8,361,958 B2

OXIMYL HCV SERINE PROTEASE INHIBITORS

RELATED APPLICATIONS

This application claims the benefit of U.S. provisional application No. 60/992,572 filed on Dec. 5, 2007. The contents of the above application are incorporated herein by reference.

TECHNICAL FIELD

The present invention relates to novel hepatitis C virus (HCV) protease inhibitor compounds having antiviral activity against HCV and useful in the treatment of HCV infections. More particularly, the invention relates to novel oximyl HCV protease inhibitor compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-alpha (IFN-α), while a new approved second-generation treatment involves co-treatment with IFN-α and the general antiviral nucleoside mimics like ribavirin. Both of these treatments suffer from interferon-related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug preferably possesses significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3-NS4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov., 1, 867-881 (2002). More relevant patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999); US publications 20050153877, 20050261200 and 20050065073.

SUMMARY OF THE INVENTION

The present invention relates to novel HCV protease inhibitor compounds, and pharmaceutically acceptable salts, esters, or prodrugs thereof, which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds, salts, esters or prodrugs for administration to a subject suffering from HCV infection. The present invention further features pharmaceutical compositions comprising a compound of the present invention (or a pharmaceutically acceptable salt, ester or prodrug thereof) and another anti-HCV agent, such as alpha-interferon, beta-interferon, ribavirin, amantadine, another HCV protease inhibitor, or an HCV polymerase, helicase or internal ribosome entry site inhibitor. The invention also relates to methods of treating an HCV infection in a subject by administering a pharmaceutical composition of the present invention.

In one embodiment of the present invention, there are disclosed compounds of Formula I:

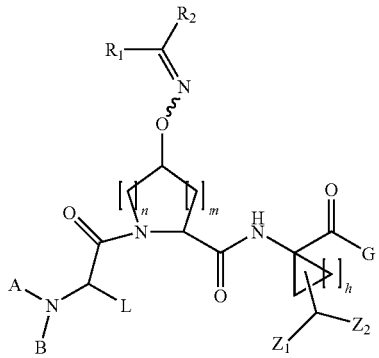

as well as the pharmaceutically acceptable salts, esters and prodrugs thereof, wherein:
$R_1$ and $R_2$ are independently selected from the group consisting of:
  a) hydrogen;
  b) aryl;
  c) substituted aryl;
  d) heteroaryl;
  e) substituted heteroaryl;
  f) heterocyclic or substituted heterocyclic;
  g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  i) —$C_3$-$C_{12}$ cycloalkyl, or —$C_3$-$C_{12}$ cycloalkenyl;
  j) substituted —$C_3$-$C_{12}$ cycloalkyl, or substituted —$C_3$-$C_{12}$ cycloalkenyl;
  k) -Q-$R_3$, where Q is (CO), (CO)O, (CO)N$R_4$, (SO), (SO$_2$), (SO$_2$)N$R_4$; and $R_3$ and $R_4$ are independently selected from the group consisting of:
    (i) hydrogen;
    (ii) aryl;
    (iii) substituted aryl;
    (iv) heteroaryl;
    (v) substituted heteroaryl;
    (vi) heterocyclic;
    (vii) substituted heterocyclic;
    (viii) —$C_1$-$C_8$ alkyl, —$C_2$-$C_8$ alkenyl, or —$C_2$-$C_8$ alkynyl each containing 0, 1, 2, or 3 heteroatoms selected from O, S or N;
    (ix) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
    (x) —$C_3$-$C_{12}$ cycloalkyl, or —$C_3$-$C_{12}$ cycloalkenyl;
    (xi) substituted —$C_3$-$C_{12}$ cycloalkyl, or substituted —$C_3$-$C_{12}$ cycloalkenyl;
or $R_1$ and $R_2$ taken together with the carbon atom to which they are attached form a cyclic moiety selected from: substituted or unsubstituted cycloalkyl, cycloalkenyl, or heterocyclic; or substituted or unsubstituted cycloalkyl, cycloalkenyl, or heterocyclic each fused with one or more group consisting of aryl, substituted aryl, heteroaryl, substituted heteroaryl, heterocyclic, substituted heterocyclic, cycloalkyl, substituted cycloalkyl, cycloakenyl, and substituted cycloalkenyl;

G is -E-$R_3$, where E is absent or E is O, CO, (CO)O, (CO)NH, N$R_5$, NH(CO), NH(CO)NH, NH(SO$_2$)NH or NHSO$_2$;
A is selected from the group consisting of $R_5$, (CO)$R_5$, (CO)OR$_5$, (CO)NHR$_5$, SO$_2$R$_5$, (SO$_2$)OR$_5$ and SO$_2$NHR$_5$;
$R_5$ is selected from the group consisting of:
  a) hydrogen
  b) aryl;
  c) substituted aryl;
  d) heteroaryl;
  e) substituted heteroaryl;
  f) heterocyclic;
  g) substituted heterocyclic;
  h) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  i) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  j) —$C_3$-$C_{12}$ cycloalkyl, or —$C_3$-$C_{12}$ cycloalkenyl;
  k) substituted —$C_3$-$C_{12}$ cycloalkyl, or substituted-$C_3$-$C_{12}$ cycloalkenyl;
B is H or $CH_3$;
L is selected from the group consisting of:
  (1) hydrogen;
  (2) aryl;
  (3) substituted aryl;
  (4) heteroaryl;
  (5) substituted heteroaryl;
  (6) heterocyclic;
  (7) substituted heterocyclic;
  (8) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  (9) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  (10) —$C_3$-$C_{12}$ cycloalkyl, or —$C_3$-$C_{12}$ cycloalkenyl;
  (11) substituted —$C_3$-$C_{12}$ cycloalkyl, or substituted —$C_3$-$C_{12}$ cycloalkenyl;
$Z_1$ and $Z_2$ are independently selected from halogen; preferably F, Cl and Br;
m=0, 1, 2 or 3;
n=1, 2 or 3 and
h=1, 2, or 3.

In another embodiment, the present invention features pharmaceutical compositions comprising a compound of the invention, or a pharmaceutically acceptable salt, ester or prodrug thereof. In still another embodiment of the present invention there are disclosed pharmaceutical compositions comprising a therapeutically effective amount of a compound of the invention, or a pharmaceutically acceptable salt, ester or prodrug thereof, in combination with a pharmaceutically acceptable carrier or excipient. In yet another embodiment of the invention are methods of treating a hepatitis C infection in a subject in need of such treatment with said pharmaceutical compositions.

DETAILED DESCRIPTION OF THE INVENTION

In a first embodiment, the present invention is a compound of formula I as illustrated above, or a pharmaceutically acceptable salt, ester or prodrug thereof.

In another embodiment, the present invention relates to a compound of formula II, or a pharmaceutically acceptable salt, ester or prodrug thereof:

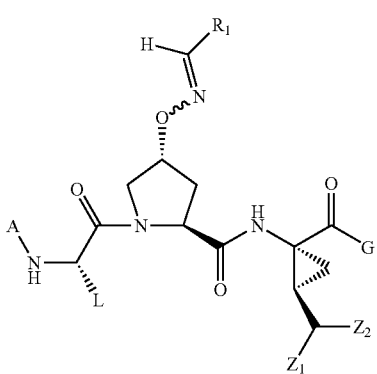

(II)

where A, G, L, $R_1$, $Z_1$ and $Z_2$ are as previously defined. In a preferred example, $R_1$ is not hydrogen.

In another example, $R_1$ is selected from the group consisting of aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L can be selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br.

In still another example, $R_1$ is selected from the group consisting of aryl, substituted aryl, heteroaryl, substituted heteroaryl, heterocyclic, and substituted heterocyclic. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still yet another example, $R_1$ is selected from the group consisting of aryl, substituted aryl, heteroaryl, substituted heteroaryl, heterocyclic, and substituted heterocyclic. A is —C(O)—O—$R_5$, where $R_5$ is —$C_3$-$C_{12}$ cycloalkyl or substituted —$C_3$-$C_{12}$ cycloalkyl. L is selected from —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is selected from —$C_3$-$C_{12}$ cycloalkyl or substituted —$C_3$-$C_{12}$ cycloalkyl.

In another example, $R_1$ is selected from the group consisting of aryl, substituted aryl, heteroaryl, substituted heteroaryl, heterocyclic, and substituted heterocyclic. A is —C(O)—NH—$R_5$, where $R_5$ is —$C_1$-$C_8$ alkyl or substituted —$C_1$-$C_8$ alkyl. L is selected from —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is selected from —$C_3$-$C_{12}$ cycloalkyl or substituted —$C_3$-$C_{12}$ cycloalkyl.

In yet another example, $R_1$ is selected from the group consisting of aryl, substituted aryl, heteroaryl, substituted heteroaryl, heterocyclic, and substituted heterocyclic. A is —C(O)—$R_5$, where $R_5$ is substituted —$C_1$-$C_8$ alkyl (e.g., substituted methyl or ethyl) and is substituted with (1) aryl or heteroaryl, (2) —NHC(O)-aryl or —NHC(O)-heteroaryl, and optionally (3) one or more other substituents. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_1$ is selected from the group consisting of aryl, substituted aryl, heteroaryl, substituted heteroaryl, heterocyclic, and substituted heterocyclic. A is —C(O)—$R_5$, where $R_5$ is substituted methyl and is substituted at least with (1) aryl or heteroaryl and (2) —NHC(O)-aryl or —NHC(O)-heteroaryl. L is —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is —$C_3$-$C_{12}$ cycloalkyl or substituted —$C_3$-$C_{12}$ cycloalkyl.

In one embodiment, the present invention relates to a compound of formula III, or a pharmaceutically acceptable salt, ester or prodrug thereof:

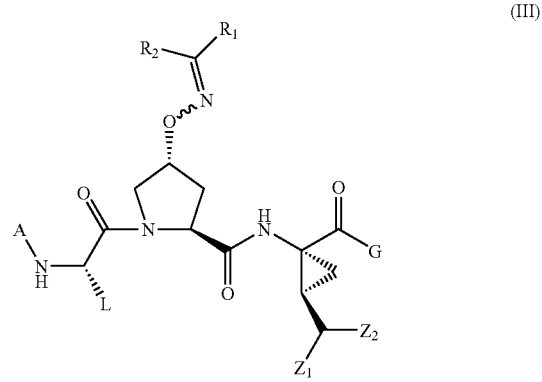

(III)

where A, G, L, $R_1$, $R_2$, $Z_1$ and $Z_2$ are as previously defined in the first embodiment. In one example, $R_1$ and $R_2$ are not both hydrogen.

In another example, $R_1$ and $R_2$ are independently selected from the group consisting of aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —C$_3$-C$_{12}$ cycloalkyl, and substituted —C$_3$-C$_{12}$ cycloalkenyl; or R$_1$ and R$_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R$_3$, where each R$_3$ is independently selected from aryl, substituted aryl, heteroaryl, substituted heteroaryl, heterocyclic or substituted heterocyclic. A can be selected from the group consisting of —C(O)—R$_5$, —C(O)—O—R$_5$ and —C(O)—NH—R$_5$, where R$_5$ is selected from aryl, substituted aryl, heteroaryl, substituted heteroaryl, heterocyclic, substituted heterocyclic, —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. L can be selected from C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. G can be —O—R$_3$, —NH—C(O)—R$_3$, —NH—SO$_2$—NH—R$_3$ or —NHSO$_2$—R$_3$, where R$_3$ is selected from hydrogen, aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. Z$_1$ and Z$_2$ are independently selected from F, Cl and Br.

In a preferred example, R$_1$ and R$_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R$_3$, where each R$_3$ is independently selected from aryl, substituted aryl, heteroaryl, substituted heteroaryl, heterocyclic or substituted heterocyclic. A is —C(O)—O—R$_5$ or —C(O)—NH—R$_5$, where R$_5$ is —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. L is selected from —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. Z$_1$ and Z$_2$ are independently selected from F, Cl and Br. G is —NHSO$_2$—R$_3$, where R$_3$ is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In another preferred example, R$_1$ and R$_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R$_3$, where each R$_3$ is independently selected from aryl, substituted aryl, heteroaryl, substituted heteroaryl, heterocyclic or substituted heterocyclic. A is —C(O)—O—R$_5$, where R$_5$ is —C$_3$-C$_{12}$ cycloalkyl or substituted —C$_3$-C$_{12}$ cycloalkyl. L is selected from —C$_1$-C$_8$ alkyl or substituted —C$_1$-C$_8$ alkyl. Z$_1$ and Z$_2$ are independently selected from F, Cl and Br. G is —NHSO$_2$—R$_3$, where R$_3$ is selected from —C$_3$-C$_{12}$ cycloalkyl or substituted —C$_3$-C$_{12}$ cycloalkyl.

In still another preferred example, R$_1$ and R$_2$ taken together with the carbon atom to which they are attached form

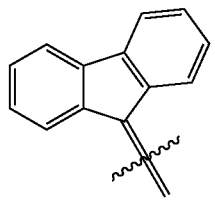 [SMILES: *=C1c2ccccc2-c2ccccc21]

which is optionally substituted with one or more groups, and each group is independently selected from halogen, hydroxy, nitro, cyano, amino, formyl, —C$_1$-C$_8$alkyl or —C$_2$-C$_8$alkenyl, or —C$_2$-C$_8$alkynyl. A is —C(O)—O—R$_5$, where R$_5$ is —C$_3$-C$_{12}$ cycloalkyl or substituted —C$_3$-C$_{12}$ cycloalkyl. L is selected from —C$_1$-C$_8$ alkyl or substituted —C$_1$-C$_8$ alkyl. Z$_1$ and Z$_2$ are independently selected from F, Cl and Br. G is —NHSO$_2$—R$_3$, where R$_3$ is selected from —C$_3$-C$_{12}$ cycloalkyl or substituted —C$_3$-C$_{12}$ cycloalkyl.

In yet another preferred example, R$_1$ and R$_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R$_3$, where each R$_3$ is independently selected from aryl, substituted aryl, heteroaryl, substituted heteroaryl, heterocyclic or substituted heterocyclic. A is —C(O)—NH—R$_5$, where R$_5$ is —C$_1$-C$_8$ alkyl or substituted —C$_1$-C$_8$ alkyl. L is selected from —C$_1$-C$_8$ alkyl or substituted —C$_1$-C$_8$ alkyl. Z$_1$ and Z$_2$ are independently selected from F, Cl and Br. G is —NHSO$_2$—R$_3$, where R$_3$ is selected from —C$_3$-C$_{12}$ cycloalkyl or substituted —C$_3$-C$_{12}$ cycloalkyl. Preferably, R$_1$ and R$_2$ taken together with the carbon atom to which they are attached form

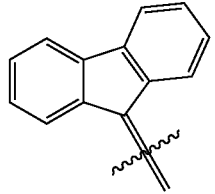 [SMILES: *=C1c2ccccc2-c2ccccc21]

which is optionally substituted with one or more groups, and each group is independently selected from halogen, hydroxy, nitro, cyano, amino, formyl, —C$_1$-C$_8$alkyl or —C$_2$-C$_8$alkenyl, or —C$_2$-C$_8$alkynyl.

In another preferred example, R$_1$ and R$_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more R$_3$, where each R$_3$ is independently selected from aryl, substituted aryl, heteroaryl, substituted heteroaryl, heterocyclic or substituted heterocyclic. A is —C(O)—R$_5$, where R$_5$ is substituted —C$_1$-C$_8$ alkyl (e.g., substituted methyl or ethyl) and is substituted with (1) aryl or heteroaryl, (2) —NHC(O)-aryl or —NHC(O)-heteroaryl, and optionally (3) one or more other substituents. L is selected from —C$_1$-C$_8$ alkyl, —C$_2$-C$_8$ alkenyl, —C$_2$-C$_8$ alkynyl, substituted —C$_1$-C$_8$ alkyl, substituted —C$_2$-C$_8$ alkenyl, substituted —C$_2$-C$_8$ alkynyl, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl. Z$_1$ and Z$_2$ are independently selected from F, Cl and Br. G is —NHSO$_2$—R$_3$, where R$_3$ is selected from aryl, substituted aryl, heteroaryl, substituted heteroaryl, heterocyclic, substituted heterocyclic, —C$_3$-C$_{12}$ cycloalkyl, —C$_3$-C$_{12}$ cycloalkenyl, substituted —C$_3$-C$_{12}$ cycloalkyl, or substituted —C$_3$-C$_{12}$ cycloalkenyl.

In yet another preferred example, $R_1$ and $R_2$ taken together with the carbon atom to which they are attached form

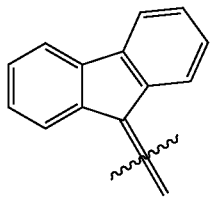 [SMILES: *=C1c2ccccc2-c2ccccc21]

which is optionally substituted with one or more groups, and each group is independently selected from halogen, hydroxy, nitro, cyano, amino, formyl, —$C_1$-$C_8$alkyl or —$C_2$-$C_8$alkenyl, or —$C_2$-$C_8$alkynyl. A is —C(O)—$R_5$, where $R_5$ is substituted methyl and is substituted at least with (1) aryl or heteroaryl and (2) —NHC(O)-aryl or —NHC(O)-heteroaryl. L is —$C_1$-$C_8$ alkyl or substituted —$C_1$-$C_8$ alkyl. $Z_1$ and $Z_2$ are independently selected from F, Cl and Br. G is —NHSO$_2$—$R_3$, where $R_3$ is —$C_3$-$C_{12}$ cycloalkyl or substituted —$C_3$-$C_{12}$ cycloalkyl.

In a further embodiment, the present invention relates to a compound of formula IV, or a pharmaceutically acceptable salt, ester or prodrug thereof:

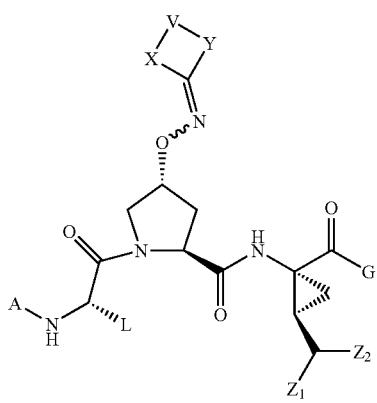

(IV)

wherein V is absent, or V is CO, O, S, SO, SO$_2$, NH, NCH$_3$, or (CH$_2$)$_q$; where q is 1, 2, 3 or 4; and where X and Y are independently selected from the group consisting of: aryl; substituted aryl; heteroaryl; substituted heteroaryl; heterocyclic; substituted heterocyclic; and where A, G, L, $Z_1$ and $Z_2$ are as previously defined in the first embodiment.

In one example,

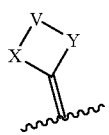

is selected from

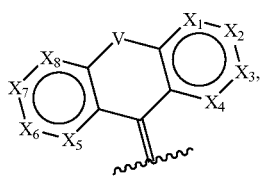

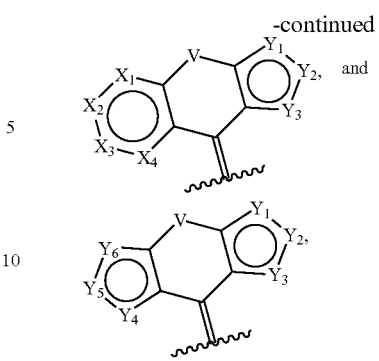

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or (CH$_2$)$_q$, where q is 1, 2 or 3. A can be selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G can be —O—$R_3$, —NH—C(O)—$R_3$, —NH—SO$_2$—NH—$R_3$ or —NHSO$_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example,

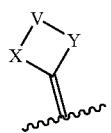

is selected from

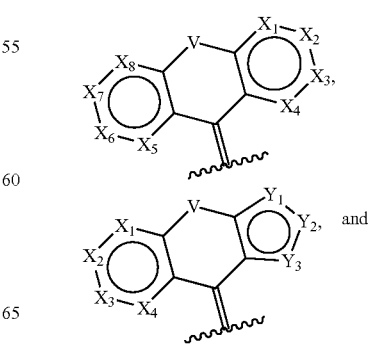

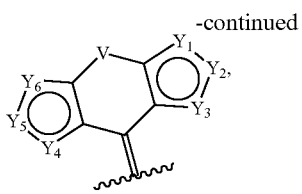

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—O—$R_5$, where $R_5$ is —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —NHSO$_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still yet another example,

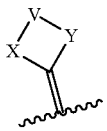

is selected from

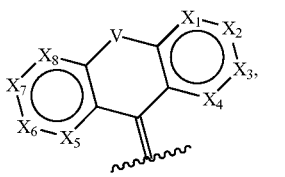

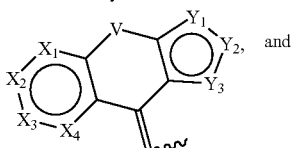 and

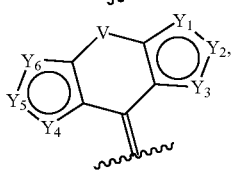

wherein $X_1$-$X_8$ are independently selected from CH and N and $X_1$-$X_8$ can be further substituted when it is a CH, and $Y_1$-$Y_3$ are independently selected from CH, N, NH, S and O and $Y_1$-$Y_3$ can be further substituted when it is CH or NH; V is absent, CO, O, S, NH, or $(CH_2)_q$, where q is 1, 2 or 3. A is —C(O)—O—$R_5$, where $R_5$ is —$C_3$-$C_{12}$ cycloalkyl or substituted —$C_3$-$C_{12}$ cycloalkyl. L is selected from —$C_1$-$C_8$ alkyl or substituted —$C_1$-$C_8$ alkyl. $Z_1$ and $Z_2$ are independently selected from F, Cl and Br. G is —NHSO$_2$—$R_3$, where $R_3$ is selected from —$C_3$-$C_{12}$ cycloalkyl or substituted —$C_3$-$C_{12}$ cycloalkyl.

In a preferred example, $R_1$ and $R_2$ taken together with the carbon atom to which they are attached form

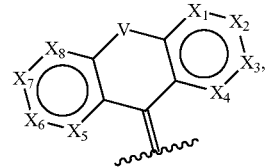

wherein $X_1$-$X_8$ are independently selected from CH and N and $X_1$-$X_8$ can be further substituted when it is a CH; V is absent, CO, O, S, NH, or $(CH_2)_q$, where q is 1, 2 or 3. A is —C(O)—O—$R_5$, where $R_5$ is —$C_3$-$C_{12}$ cycloalkyl or substituted —$C_3$-$C_{12}$ cycloalkyl. L is selected from —$C_1$-$C_8$ alkyl or substituted —$C_1$-$C_8$ alkyl. $Z_1$ and $Z_2$ are independently selected from F, Cl and Br. G is —NHSO$_2$—$R_3$, where $R_3$ is selected from —$C_3$-$C_{12}$ cycloalkyl or substituted —$C_3$-$C_{12}$ cycloalkyl.

In a most preferred example, $R_1$ and $R_2$ taken together with the carbon atom to which

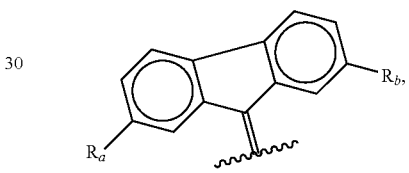

they are attached form wherein Ra and Rb is independently selected from hydrogen or halogen. A is —C(O)—O—$R_5$, where $R_5$ is —$C_3$-$C_{12}$ cycloalkyl or substituted —$C_3$-$C_{12}$ cycloalkyl. L is selected from —$C_1$-$C_8$ alkyl or substituted —$C_1$-$C_8$ alkyl. $Z_1$ and $Z_2$ are independently selected from F, Cl and Br. G is —NHSO$_2$—$R_3$, where $R_3$ is selected from —$C_3$-$C_{12}$ cycloalkyl or substituted —$C_3$-$C_{12}$ cycloalkyl.

In one embodiment, the present invention relates to a compound of formula V, or a pharmaceutically acceptable salt, ester or prodrug thereof:

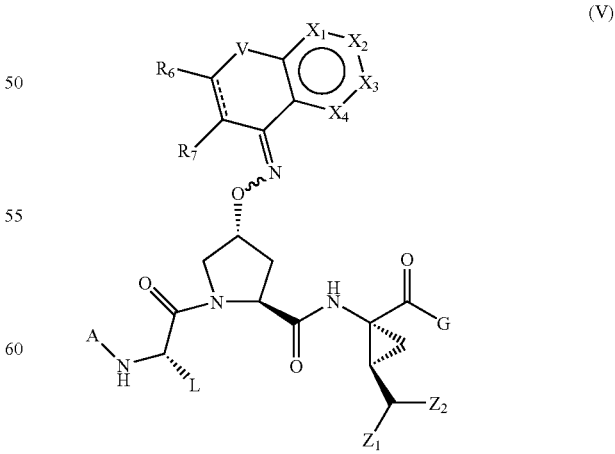

(V)

Where $X_1$-$X_4$ are independently selected from CO, CH, NH, O and N; where $X_1$-$X_4$ can be further substituted when any one of $X_1$-$X_4$ is a CH or NH; where $R_6$ and $R_7$ are independently $R_3$, where $R_3$ is independently selected from the group consisting of:
(i) hydrogen;
(ii) aryl;
(iii) substituted aryl;
(iv) heteroaryl;
(v) substituted heteroaryl;
(vi) heterocyclic;
(vii) substituted heterocyclic;
(viii) -$C_1$-$C_8$ alkyl, —$C_2$-$C_8$ alkenyl, or —$C_2$-$C_8$ alkynyl each containing 0, 1, 2, or 3 heteroatoms selected from O, S or N;
(ix) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(x) —$C_3$-$C_{12}$ cycloalkyl, or —$C_3$-$C_{12}$ cycloalkenyl;
(xi) substituted —$C_3$-$C_{12}$ cycloalkyl, or substituted —$C_3$-$C_{12}$ cycloalkenyl;
and where A, G, L, V, $Z_1$ and $Z_2$ are as previously defined in the embodiment immediately above. Alternatively, $R_6$ and $R_7$ can be independently selected from halogen, oxo, thioxo, nitro, cyano, —$OR_3$, —$SR_3$, —$NR_3R_4$, —$SOR_3$, —$SO_2R_3$, —$NHSO_2R_3$, —$SO_2NHR_3$, —$COR_3$, —$CO_2R_3$, (CO)$NHR_3$, —$OCOR_3$, $OCONHR_3$, $NHCO_2R_3$, —$NH(CO)R_3$, —$NH(CO)NHR_3$, and —$NH(SO_2)NHR_3$.

In one example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G can be —O—$R_3'$, —NH—C(O)—$R_3'$, —NH—$SO_2$—NH—$R_3'$ or —$NHSO_2$—$R_3'$, where $R_3'$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —$NHSO_2$—$R_3'$, where $R_3'$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$, where $R_5$ is —$C_3$-$C_{12}$ cycloalkyl or substituted —$C_3$-$C_{12}$ cycloalkyl. L is selected from —$C_1$-$C_8$ alkyl or substituted —$C_1$-$C_8$ alkyl. $Z_1$ and $Z_2$ are independently selected from F, Cl and Br. G is —$NHSO_2$—$R_3'$, where $R_3'$ is selected from —$C_3$-$C_{12}$ cycloalkyl or substituted —$C_3$-$C_{12}$ cycloalkyl.

In another example, $R_6$ and $R_7$ are independently from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—NH—$R_5$, where $R_5$ is —$C_1$-$C_8$ alkyl or substituted —$C_1$-$C_8$ alkyl. L is selected from —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is selected from —$C_3$-$C_{12}$ cycloalkyl or substituted —$C_3$-$C_{12}$ cycloalkyl.

In yet another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —NHC(O)-aryl or —NHC(O)-heteroaryl, and optionally (3) one or more other substituents. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —NHC(O)-aryl or —NHC(O)-heteroaryl. L is —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is —$C_3$-$C_{12}$ cycloalkyl or substituted —$C_3$-$C_{12}$ cycloalkyl.

In another embodiment, the present invention relates to a compound of formula VI, or a pharmaceutically acceptable salt, ester or prodrug thereof:

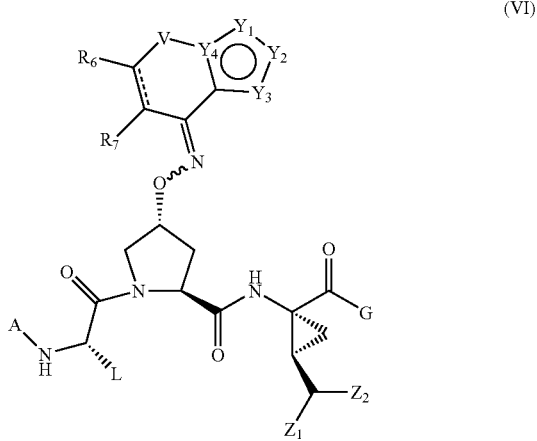

(VI)

Where $Y_1$-$Y_3$ are independently selected from CO, CH, NH, N, S and O; and $Y_1$-$Y_3$ can be further substituted when any one of $Y_1$-$Y_3$ is CH or NH; $Y_4$ is selected from C, CH and N; and where A, G, L, $R_6$, $R_7$, V, $Z_1$ and $Z_2$ are as previously defined in the embodiment immediately above.

In one example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G can be —O—$R_3'$, —NH—C(O)—$R_3'$, —NH—$SO_2$—NH—$R_3'$ or —$NHSO_2$—$R_3'$, where $R_3'$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —$NHSO_2$—$R_3'$, where $R_3'$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$, where $R_5$ is —$C_3$-$C_{12}$ cycloalkyl or substituted —$C_3$-$C_{12}$ cycloalkyl. L is selected from —$C_1$-$C_8$ alkyl or substituted —$C_1$-$C_8$ alkyl. $Z_1$ and $Z_2$ are independently selected from F, Cl and Br. G is —$NHSO_2$—$R_3'$, where $R_3'$ is selected from —$C_3$-$C_{12}$ cycloalkyl or substituted —$C_3$-$C_{12}$ cycloalkyl.

In another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—NH—$R_5$, where $R_5$ is —$C_1$-$C_8$ alkyl or substituted —$C_1$-$C_8$ alkyl. L is selected from —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is selected from —$C_3$-$C_{12}$ cycloalkyl or substituted —$C_3$-$C_{12}$ cycloalkyl.

In yet another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —NHC(O)-aryl or —NHC(O)-heteroaryl, and optionally (3) one or more other substituents. L is selected from —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. $Z_1$ and $Z_2$ are independently selected from F, Cl and Br. G is —$NHSO_2$—$R_3$, where $R_3$ is selected from aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —NHC(O)-aryl or —NHC(O)-heteroaryl. L is —$C_1$-$C_8$ alkyl or substituted —$C_1$-$C_8$ alkyl. $Z_1$ and $Z_2$ are independently selected from F, Cl and Br. G is —$NHSO_2$—$R_3$, where $R_3$ is —$C_3$-$C_{12}$ cycloalkyl or substituted —$C_3$-$C_{12}$ cycloalkyl.

Representative compounds of the invention include, but are not limited to, the following compounds (Table 1) according to Formula VII

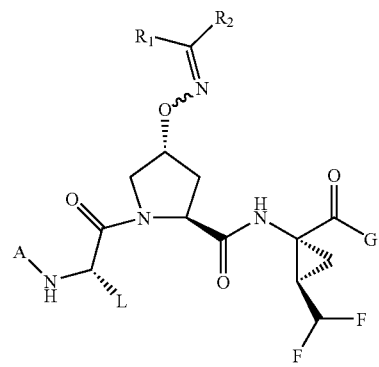

VII

Wherein $R_1$ and $R_2$ are taken together with the carbon to which they are attached to form $R_1R_2$, and A, $R_1R_2$, L and G are delineated for each example in TABLE 1.

TABLE 1

| Example | A | L | $R_1R_2$ | G |
|---|---|---|---|---|
| 1) | tert-butyl ester (–C(O)O-tBu) | tert-butyl | fluorenylidene | —OH |
| 2) | tert-butyl ester (–C(O)O-tBu) | tert-butyl | fluorenylidene | —NHSO$_2$-cyclopropyl |
| 3) | —H | tert-butyl | fluorenylidene | —NHSO$_2$-cyclopropyl |
| 4) | cyclopentyl ester (–C(O)O-cyclopentyl) | tert-butyl | fluorenylidene | —NHSO$_2$-cyclopropyl |
| 5) | cyclobutyl ester (–C(O)O-cyclobutyl) | tert-butyl | fluorenylidene | —NHSO$_2$-cyclopropyl |

TABLE 1-continued
| Example | A | L | R₁R₂ | G |
|---|---|---|---|---|
| 6) | 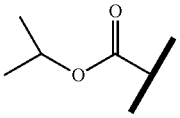 |  | 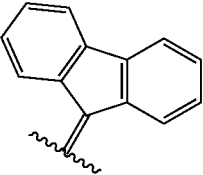 [SMILES: *=C1c2ccccc2-c2ccccc21] | 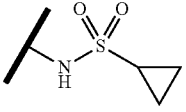 |
| 7) | 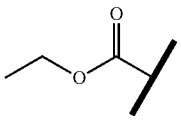 |  | 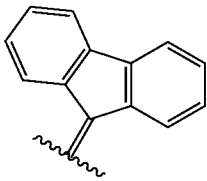 [SMILES: *=C1c2ccccc2-c2ccccc21] | 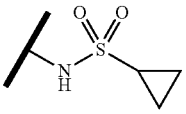 |
| 8) | 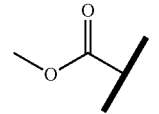 |  | 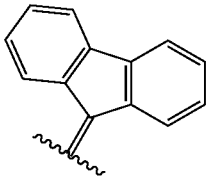 [SMILES: *=C1c2ccccc2-c2ccccc21] | 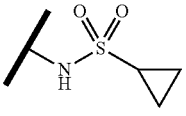 |
| 9) | 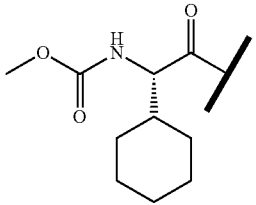 |  | 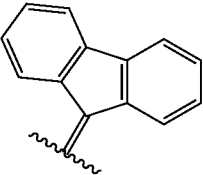 [SMILES: *=C1c2ccccc2-c2ccccc21] | 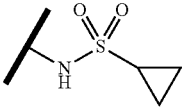 |
| 10) | 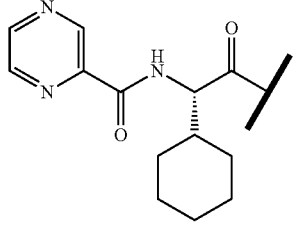 |  | 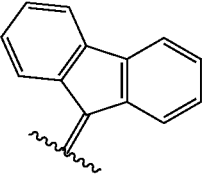 [SMILES: *=C1c2ccccc2-c2ccccc21] | 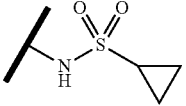 |
| 11) | 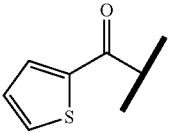 |  | 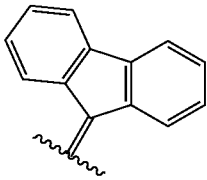 [SMILES: *=C1c2ccccc2-c2ccccc21] | 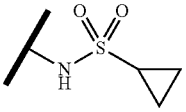 |
| 12) | 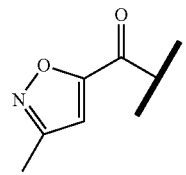 |  | 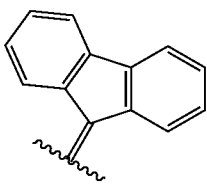 [SMILES: *=C1c2ccccc2-c2ccccc21] | 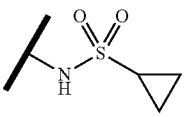 |
| 13) | 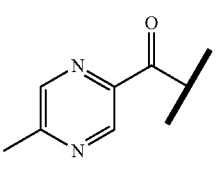 |  | 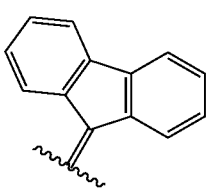 [SMILES: *=C1c2ccccc2-c2ccccc21] | 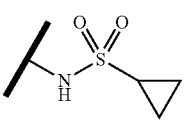 |

TABLE 1-continued
| Example | A | L | R₁R₂ | G |
|---|---|---|---|---|
| 14) |  |  |  |  |
| 15) |  |  |  | 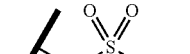 |
| 16) |  |  |  | —OH |
| 17) |  |  |  | 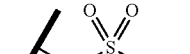 |
| 18) | —H |  |  | 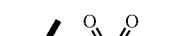 |
| 19) |  |  |  | 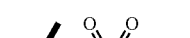 |
| 20) |  |  |  | 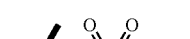 |
| 21) |  |  |  | 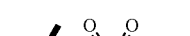 |

TABLE 1-continued
| Example | A | L | R₁R₂ | G |
|---|---|---|---|---|
| 22) | 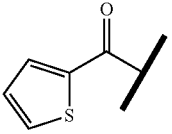 |  | 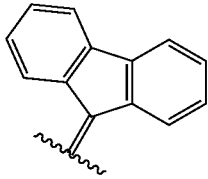 [SMILES: *=C1c2ccccc2-c2ccccc21] | 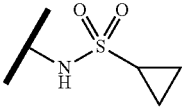 |
| 23) | 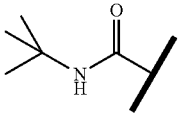 |  | 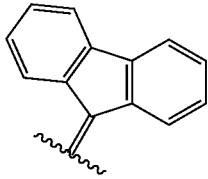 [SMILES: *=C1c2ccccc2-c2ccccc21] | 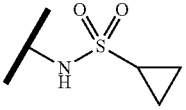 |
| 24) | 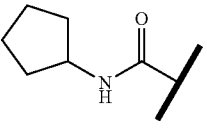 |  | 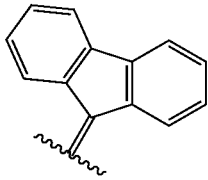 [SMILES: *=C1c2ccccc2-c2ccccc21] | 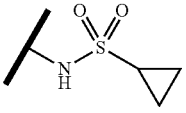 |
| 25) | 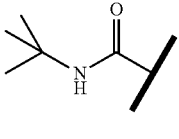 |  | 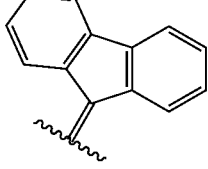 | 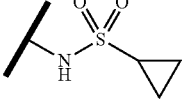 |
| 26) | 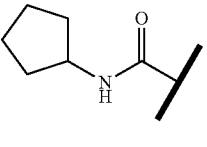 |  | 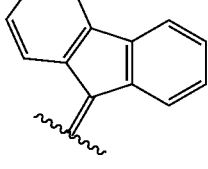 | 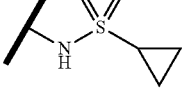 |
| 27) | 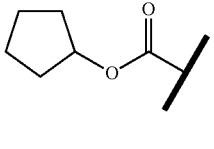 |  | 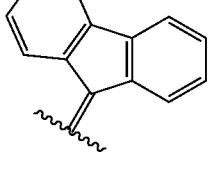 | —OH |
| 28) | 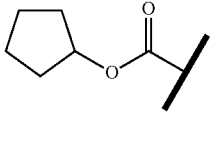 |  | 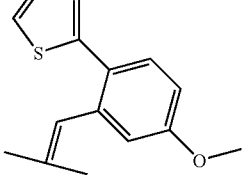 | —OH |
| 29) | 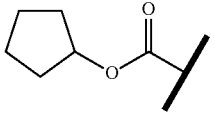 |  | 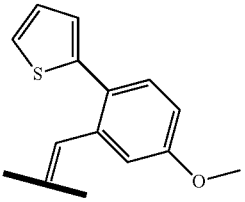 | 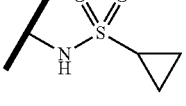 |

TABLE 1-continued

| Example | A | L | R₁R₂ | G |
|---|---|---|---|---|
| 30) | cyclopentyl ester | tBu | 6-fluorochroman-4-ylidene | —OH |
| 31) | cyclopentyl ester | tBu | 6-fluorochroman-4-ylidene | cyclopropanesulfonamide |
| 32) | tert-butyl ester | tBu | xanthen-9-ylidene | —OH |
| 33) | tert-butyl ester | tBu | xanthen-9-ylidene | cyclopropanesulfonamide |
| 34) | cyclopentyl ester | tBu | xanthen-9-ylidene | cyclopropanesulfonamide |
| 35) | tert-butyl ester | tBu | fluoren-9-yl | —OH |
| 36) | tert-butyl ester | tBu | fluoren-9-yl | N,N-dimethylsulfamide |
| 37) | cyclopentyl ester | tBu | fluoren-9-yl | N,N-dimethylsulfamide |

TABLE 1-continued
| Example | A | L | R₁R₂ | G |
|---|---|---|---|---|
| 38) | 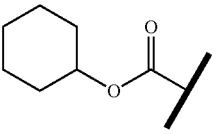 |  | 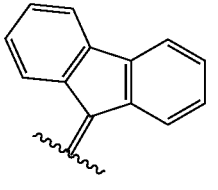 [SMILES: *=C1c2ccccc2-c2ccccc21] | 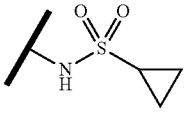 |
| 39) | 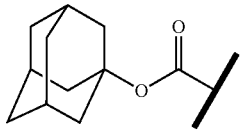 |  | 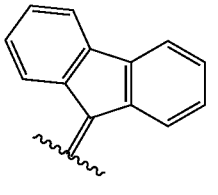 [SMILES: *=C1c2ccccc2-c2ccccc21] | 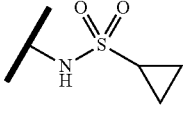 |
| 40) | 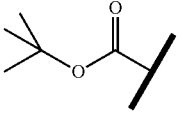 |  | 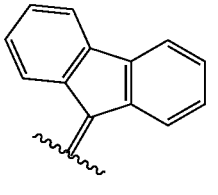 [SMILES: *=C1c2ccccc2-c2ccccc21] | 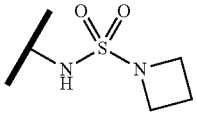 |
| 41) | 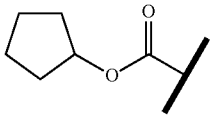 |  | 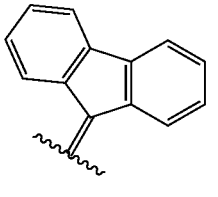 [SMILES: *=C1c2ccccc2-c2ccccc21] | 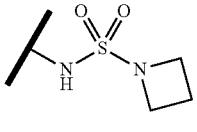 |
| 42) | 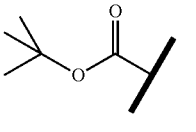 |  | 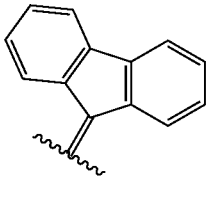 [SMILES: *=C1c2ccccc2-c2ccccc21] | 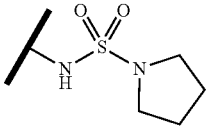 |
| 43) | 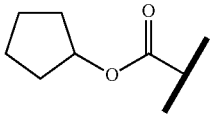 |  | 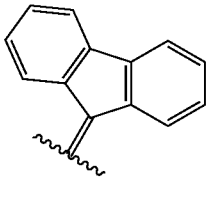 [SMILES: *=C1c2ccccc2-c2ccccc21] | 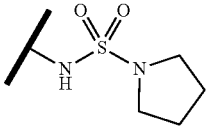 |
| 44) | 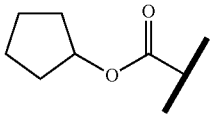 | 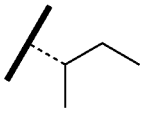 | 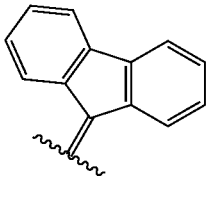 [SMILES: *=C1c2ccccc2-c2ccccc21] | 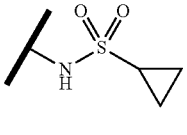 |
| 45) | 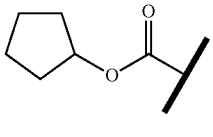 | 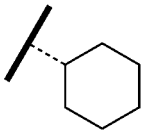 | 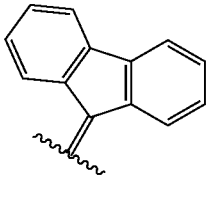 [SMILES: *=C1c2ccccc2-c2ccccc21] | 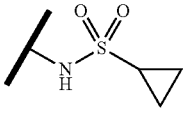 |

TABLE 1-continued

| Example | A | L | R₁R₂ | G |
|---------|---|---|------|---|
| 46) | | | | |
| 47) | | | | |
| 48) | | | | |
| 49) | | | | |
| 50) | | | | |
| 51) | | | | |
| 52) | | | | |
| 53) | | | | |

TABLE 1-continued

| Example | A | L | R₁R₂ | G |
| --- | --- | --- | --- | --- |
| 54) | cyclohexyl ester | tert-butyl | xanthene-ylidene | —NH-SO₂-cyclopropyl |
| 55) | adamantyl ester | tert-butyl | 2-(thiophen-2-yl)-4-methoxyphenyl vinylidene | —NH-SO₂-cyclopropyl |
| 56) | adamantyl ester | tert-butyl | 6-fluorochroman-4-ylidene | —NH-SO₂-cyclopropyl |
| 57) | adamantyl ester | tert-butyl | xanthene-ylidene | —NH-SO₂-cyclopropyl |
| 58) | cyclopentyl ester | tert-butyl | 1-phenylethylidene | —OH |
| 59) | cyclopentyl ester | tert-butyl | diphenylmethylidene | —OH |
| 60) | cyclopentyl ester | tert-butyl | (1-isopropyl-1-phenyl)methylidene | —OH |
| 61) | norbornyl ester | tert-butyl | (1-cyclopentyl-1-phenyl)methylidene | —OH |
| 62) | cyclopentyl ester | tert-butyl | benzylidene | —OH |

TABLE 1-continued

| Example | A | L | R₁R₂ | G |
|---|---|---|---|---|
| 63) | cyclopentyl-O-C(=O)- | -C(CH₃)₂- | 2-phenylphenyl-CH=CH- | —OH |
| 64) | cyclopentyl-O-C(=O)- | -C(CH₃)₂- | 3-phenylphenyl-CH=CH- | —OH |
| 65) | cyclopentyl-O-C(=O)- | -C(CH₃)₂- | 4-phenylphenyl-CH=CH- | —OH |
| 66) | cyclopentyl-O-C(=O)- | -C(CH₃)₂- | naphthalen-1-yl-CH=CH- | —OH |
| 67) | cyclopentyl-O-C(=O)- | -C(CH₃)₂- | naphthalen-2-yl-CH=CH- | —OH |
| 68) | cyclopentyl-O-C(=O)- | -C(CH₃)₂- | 2-phenylphenyl-C(Et)=CH- | —OH |
| 69) | cyclopentyl-O-C(=O)- | -C(CH₃)₂- | quinolin-4-yl-CH=CH- | —OH |
| 70) | cyclopentyl-O-C(=O)- | -C(CH₃)₂- | quinolin-3-yl-CH=CH- | —OH |

TABLE 1-continued

| Example | A | L | R₁R₂ | G |
|---|---|---|---|---|
| 71) | cyclopentyl-O-C(=O)- | -C(CH₃)₃- | 2-(thiophen-2-yl)phenyl with propenyl | —OH |
| 72) | cyclopentyl-O-C(=O)- | -C(CH₃)₃- | 2-(pyrazol-1-yl)phenyl with propenyl | —OH |
| 73) | cyclopentyl-O-C(=O)- | -C(CH₃)₃- | 2-(1,2,4-triazol-1-yl)phenyl with propenyl | —OH |
| 74) | cyclopentyl-O-C(=O)- | -C(CH₃)₃- | 2-(thiazol-2-yl)phenyl with propenyl | —OH |
| 75) | cyclopentyl-O-C(=O)- | -C(CH₃)₃- | 2-(imidazol-1-yl)phenyl with propenyl | —OH |
| 76) | cyclopentyl-O-C(=O)- | -C(CH₃)₃- | 2-(thiazol-2-yl)-4-methoxyphenyl with propenyl | —OH |
| 77) | cyclopentyl-O-C(=O)- | -C(CH₃)₃- | 5H-pyrrolo[2,3-b:4,5-b']dipyridin-5-ylidene | —OH |

TABLE 1-continued

| Example | A | L | R₁R₂ | G |
|---|---|---|---|---|
| 78) | cyclopentyl ester | tBu | N-methyl acridine | —OH |
| 79) | cyclopentyl ester | tBu | anthracenone | —OH |
| 80) | cyclopentyl ester | tBu | dibenzosuberylidene | —OH |
| 81) | cyclopentyl ester | tBu | indanylidene | —OH |
| 82) | cyclopentyl ester | tBu | tetrahydronaphthalenylidene | —OH |
| 83) | cyclopentyl ester | tBu | methoxy-tetrahydronaphthalenylidene | —OH |
| 84) | cyclopentyl ester | tBu | methoxy-tetrahydroquinolinylidene | —OH |
| 85) | cyclopentyl ester | tBu | dimethoxy-tetrahydronaphthalenylidene | —OH |
| 86) | cyclopentyl ester | tBu | tetrahydroquinolinylidene | —OH |

TABLE 1-continued

| Example | A | L | R₁R₂ | G |
|---------|---|---|------|---|
| 87) | cyclopentyl ester | tBu | thiochroman-4-ylidene | —OH |
| 88) | cyclopentyl ester | tBu | chroman-4-ylidene | —OH |
| 89) | cyclopentyl ester | tBu | 6-methoxychroman-4-ylidene | —OH |
| 90) | cyclopentyl ester | tBu | 7-(thiophen-2-yl)-tetrahydronaphthalen-1-ylidene | —OH |
| 91) | cyclopentyl ester | tBu | 2-phenyl-4H-chromen-4-ylidene | —OH |
| 92) | cyclopentyl ester | tBu | 3-phenyl-4H-chromen-4-ylidene | —OH |
| 93) | cyclopentyl ester | tBu | 1-phenylethylidene (α-methylstyrene) | —NHS(O)₂-cyclopropyl |
| 94) | cyclopentyl ester | tBu | diphenylmethylidene | —NHS(O)₂-cyclopropyl |
| 95) | cyclopentyl ester | tBu | 3-methyl-2-phenylbut-1-en-1-ylidene | —NHS(O)₂-cyclopropyl |

TABLE 1-continued
| Example | A | L | R₁R₂ | G |
|---|---|---|---|---|
| 96) | 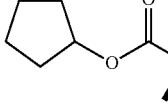 |  | 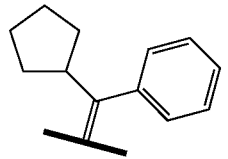 | 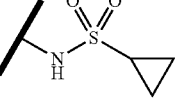 |
| 97) | 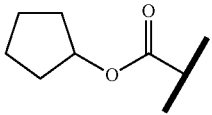 |  | 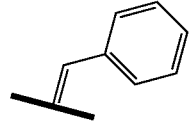 | 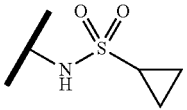 |
| 98) | 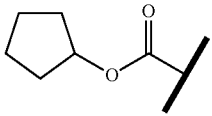 |  | 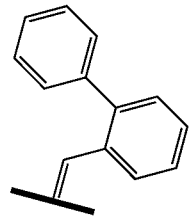 | 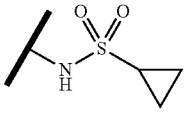 |
| 99) | 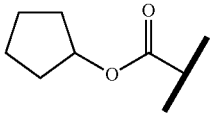 |  | 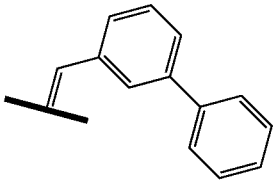 | 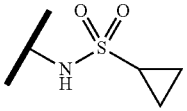 |
| 100) | 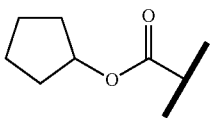 |  | 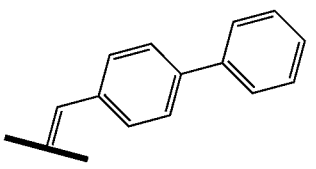 | 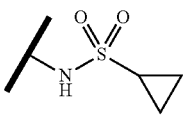 |
| 101) | 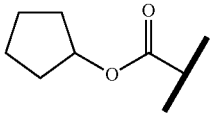 |  | 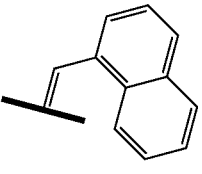 | 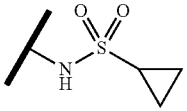 |
| 102) | 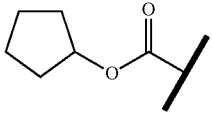 |  | 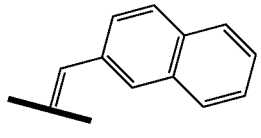 | 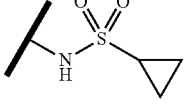 |
| 103) | 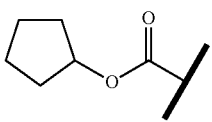 |  | 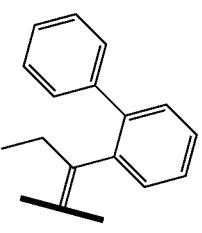 | 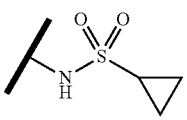 |

TABLE 1-continued
| Example | A | L | R₁R₂ | G |
|---|---|---|---|---|
| 104) | 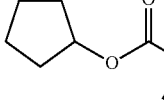 |  | 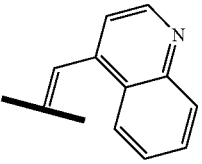 | 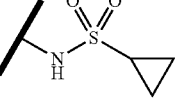 |
| 105) | 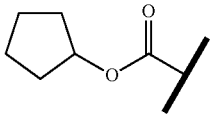 |  | 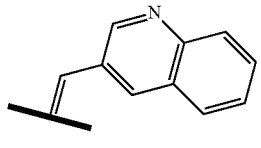 | 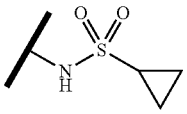 |
| 106) | 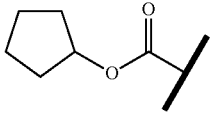 |  | 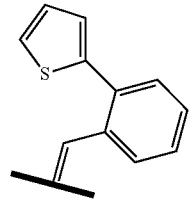 | 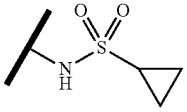 |
| 107) | 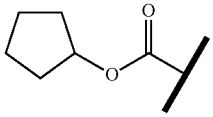 |  | 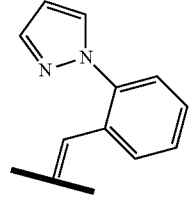 | 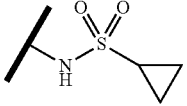 |
| 108) | 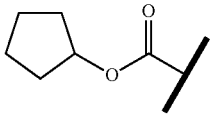 |  | 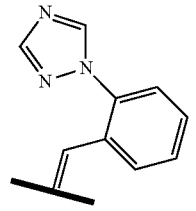 | 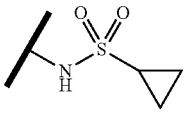 |
| 109) | 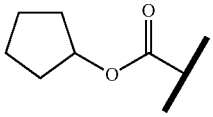 |  | 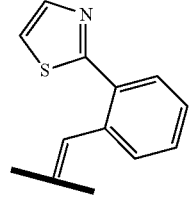 | 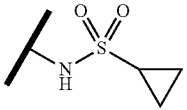 |
| 110) | 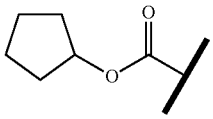 |  | 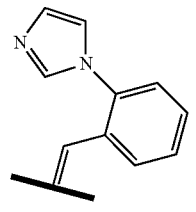 | 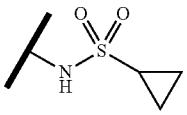 |

TABLE 1-continued
| Example | A | L | R₁R₂ | G |
|---|---|---|---|---|
| 111) | 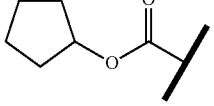 |  | 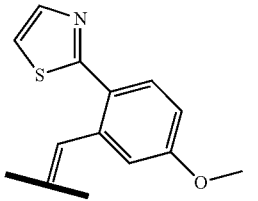 | 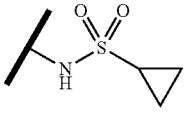 |
| 112) | 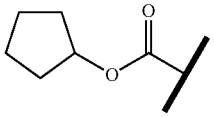 |  | 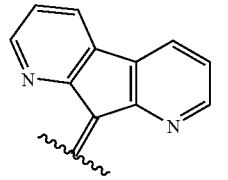 | 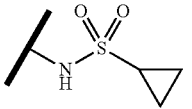 |
| 113) | 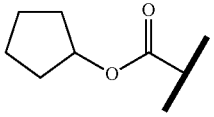 |  | 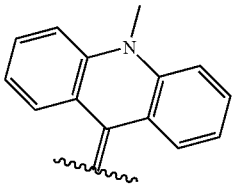 [SMILES: *=C1c2ccccc2N(C)c2ccccc21] | 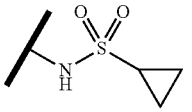 |
| 114) | 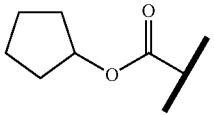 |  | 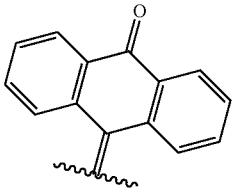 [SMILES: *=C1c2ccccc2C(=O)c2ccccc21] | 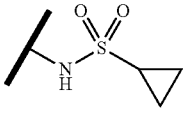 |
| 115) | 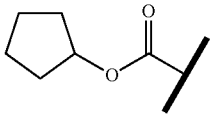 |  | 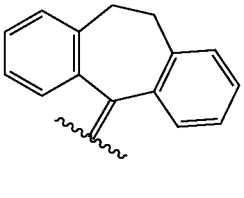 [SMILES: *=C1c2ccccc2CCc2ccccc21] | 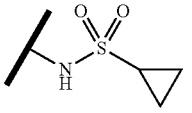 |
| 116) | 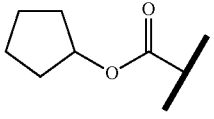 |  | 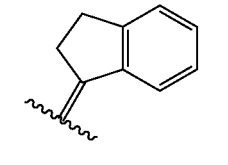 [SMILES: *=C1CCc2ccccc21] | 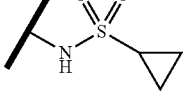 |
| 117) | 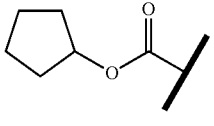 |  | 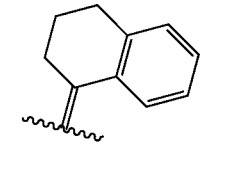 [SMILES: *=C1CCCc2ccccc21] | 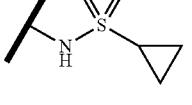 |
| 118) | 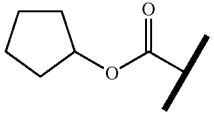 |  | 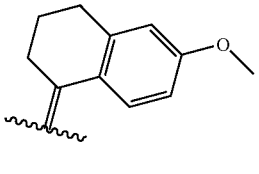 [SMILES: *=C1CCCc2cc(OC)ccc21] | 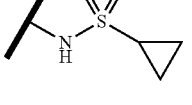 |

TABLE 1-continued
| Example | A | L | R₁R₂ | G |
|---|---|---|---|---|
| 119) | 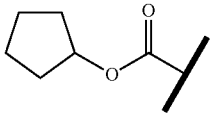 | 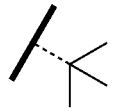 | 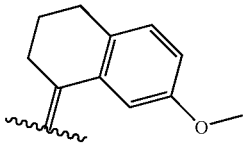 | 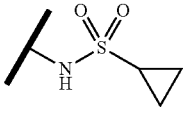 |
| 120) | 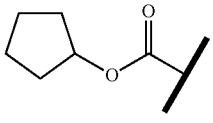 |  | 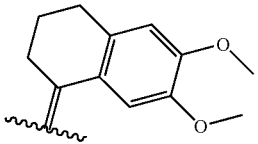 [SMILES: *=C1CCCc2cc(OC)c(OC)cc21] | 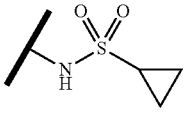 |
| 121) | 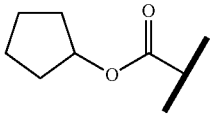 |  | 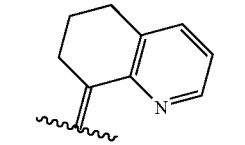 [SMILES: *=C1CCCc2cccnc21] | 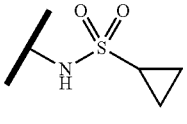 |
| 122) | 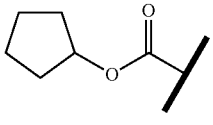 | 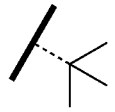 | 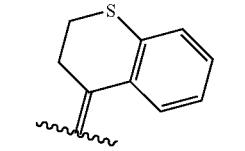 [SMILES: *=C1CCSc2ccccc21] | 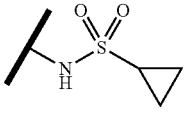 |
| 123) | 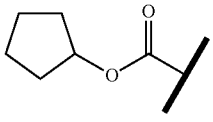 | 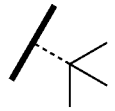 | 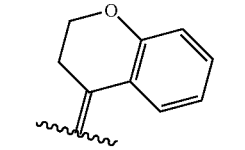 [SMILES: *=C1CCOc2ccccc21] | 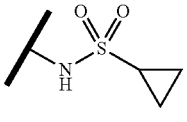 |
| 124) | 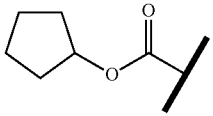 |  | 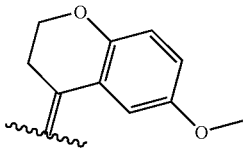 | 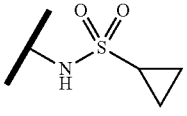 |
| 125) | 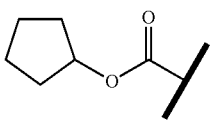 |  | 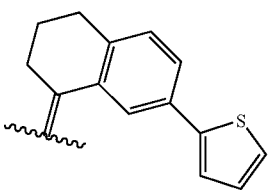 [SMILES: *=C1CCCc2ccc(-c3cccs3)cc21] | 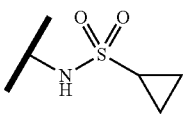 |
| 126) | 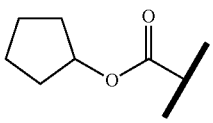 |  | 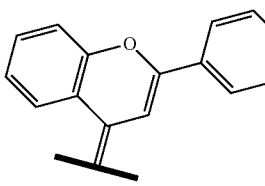 | 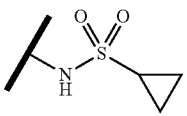 |
| 127) | 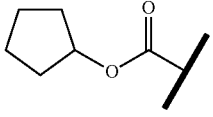 | 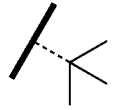 | 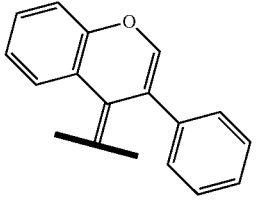 | 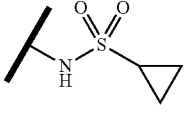 |

Additional non-limiting examples of the compounds of the invention are those compounds 128)-227) of the formula VIII:
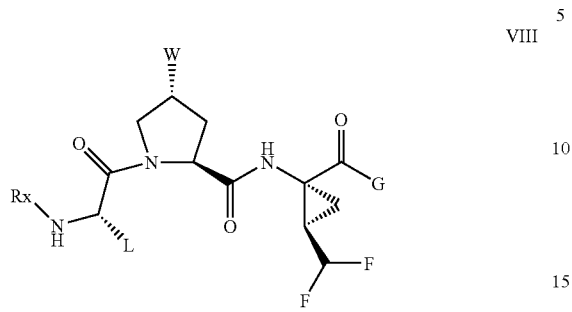
VIII
Rx, L, W and G are delineated for each example in TABLE 2.
TABLE 2
| Example | Rx | L | W | G |
|---|---|---|---|---|
| 128) | | | | |
| 129) | | | | |
| 130) | | | | |
| 131) | | | | |
| 132) | | | | |

TABLE 2-continued
| Example | Rx | L | W | G |
|---|---|---|---|---|
| 133) | 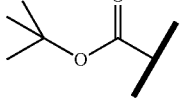 | 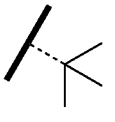 | 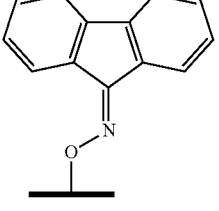 | 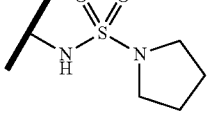 |
| 134) | 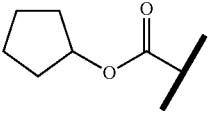 |  | 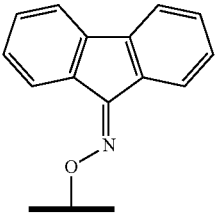 | 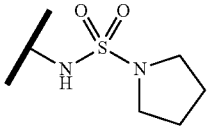 |
| 135) | 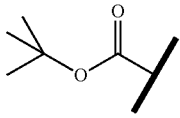 |  | 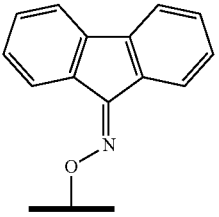 | 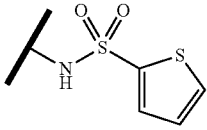 |
| 136) | 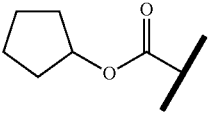 |  | 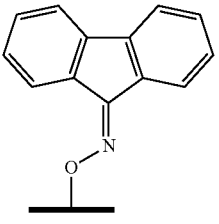 | 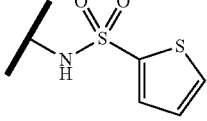 |
| 137) | 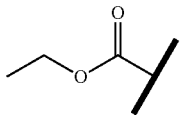 |  | 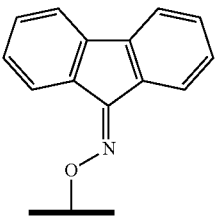 | 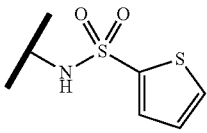 |
| 138) | 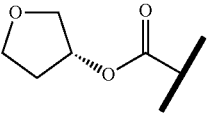 |  | 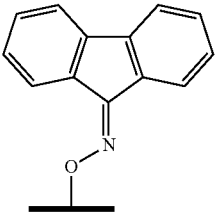 | 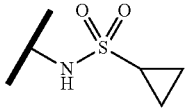 |
| 139) | 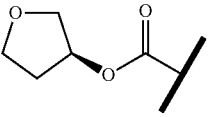 |  | 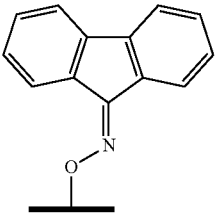 | 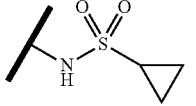 |

TABLE 2-continued
| Example | Rx | L | W | G |
|---|---|---|---|---|
| 140) | 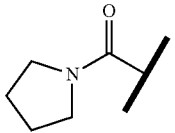 |  | 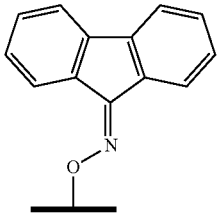 | 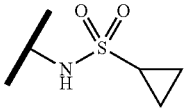 |
| 141) | 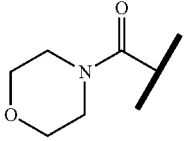 |  | 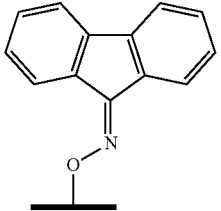 | 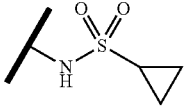 |
| 142) | 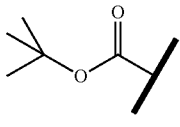 |  | 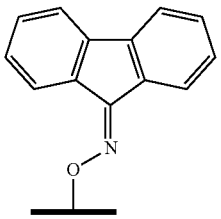 | 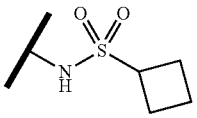 |
| 143) | 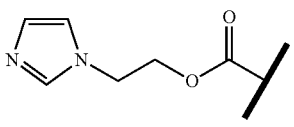 |  | 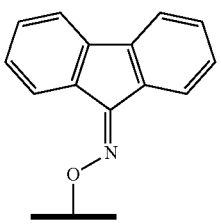 | 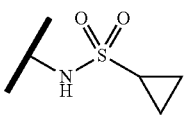 |
| 144) | 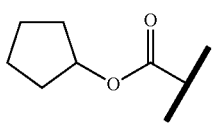 |  | —O—NH$_2$ | 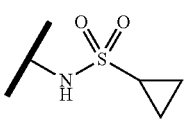 |
| 145) | 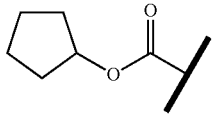 |  | 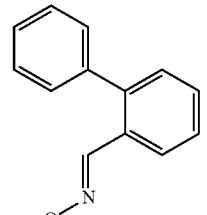 | 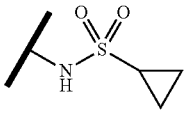 |
| 146) | 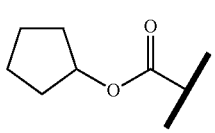 |  | 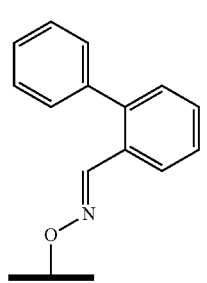 | 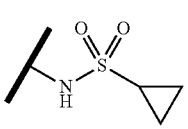 |

TABLE 2-continued
| Example | Rx | L | W | G |
|---|---|---|---|---|
| 147) | 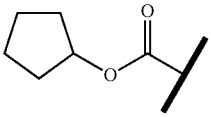 | 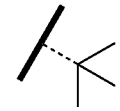 | 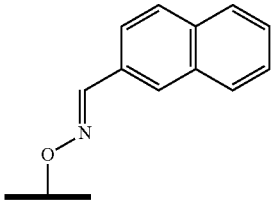 | 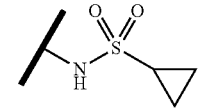 |
| 148) | 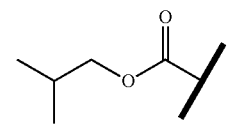 | 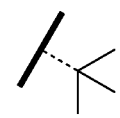 | 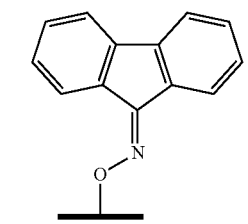 | 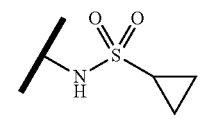 |
| 149) | 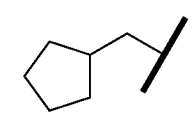 | 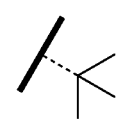 | 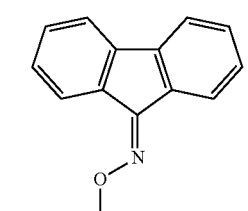 | 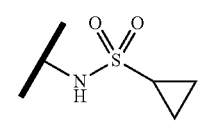 |
| 150) | 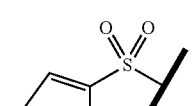 | 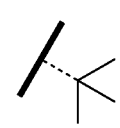 | 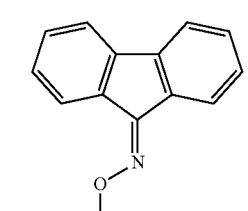 | 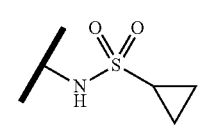 |
| 151) | 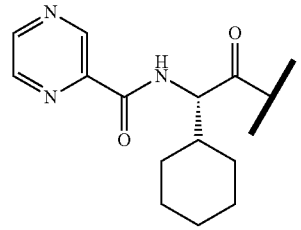 | 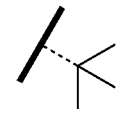 | 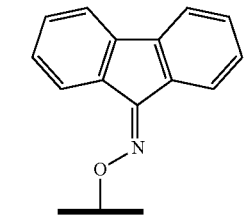 | 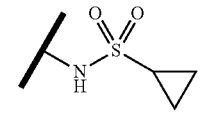 |
| 152) | 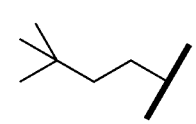 |  | 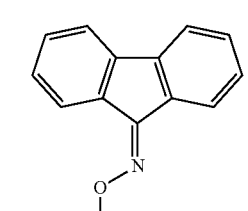 | 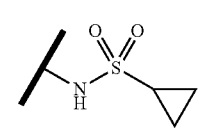 |
| 153) | 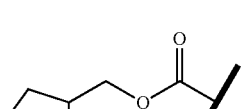 |  | 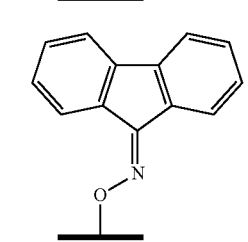 | 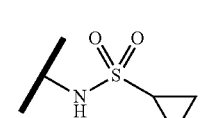 |

TABLE 2-continued
| Example | Rx | L | W | G |
|---|---|---|---|---|
| 154) | 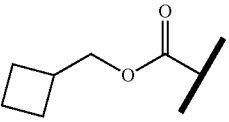 | 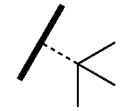 | 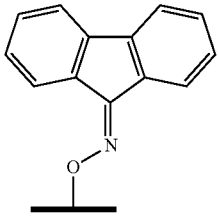 | 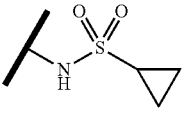 |
| 155) | 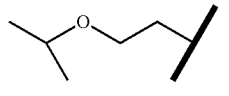 |  | 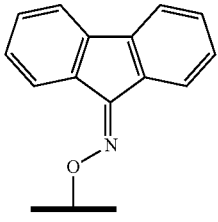 | 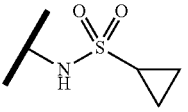 |
| 156) | 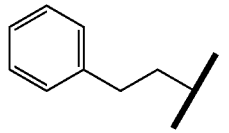 |  | 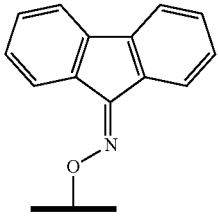 | 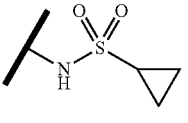 |
| 157) | 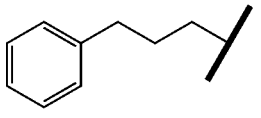 |  | 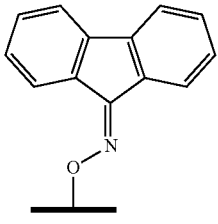 | 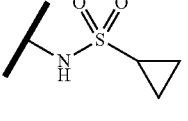 |
| 158) | 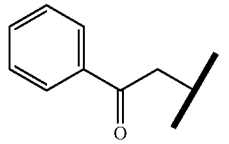 |  | 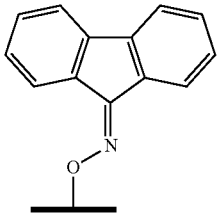 | 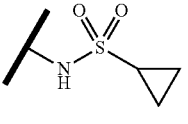 |
| 159) | 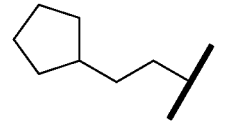 |  | 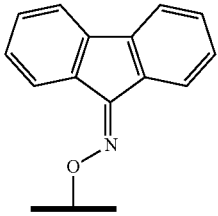 | 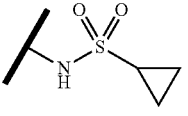 |
| 160) | 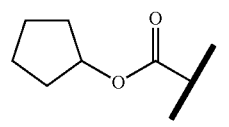 |  | 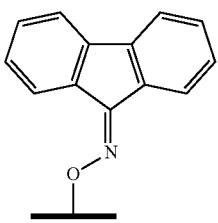 | 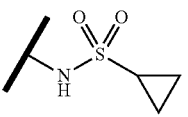 |

TABLE 2-continued

| Example | Rx | L | W | G |
|---|---|---|---|---|
| 161) | 4,4,4-trifluorobutyl | tert-butyl | fluoren-9-ylidene aminooxy | cyclopropanesulfonamido |
| 162) | 4,4-dimethyl-3-oxopentyl | tert-butyl | fluoren-9-ylidene aminooxy | cyclopropanesulfonamido |
| 163) | 3-carboxypropyl | tert-butyl | fluoren-9-ylidene aminooxy | cyclopropanesulfonamido |
| 164) | 4-(tert-butylamino)-4-oxobutyl | tert-butyl | fluoren-9-ylidene aminooxy | cyclopropanesulfonamido |
| 165) | 3-(2-fluorophenyl)propyl | tert-butyl | fluoren-9-ylidene aminooxy | cyclopropanesulfonamido |
| 166) | 3-(3-fluorophenyl)propyl | tert-butyl | fluoren-9-ylidene aminooxy | cyclopropanesulfonamido |
| 167) | 3-(4-fluorophenyl)propyl | tert-butyl | fluoren-9-ylidene aminooxy | cyclopropanesulfonamido |

TABLE 2-continued

| Example | Rx | L | W | G |
|---|---|---|---|---|
| 168) | adamantylmethyl | tert-butyl | fluorenylidene-aminooxy | NH-SO2-cyclopropyl |
| 169) | 2-(naphthalen-1-yl)ethyl | tert-butyl | fluorenylidene-aminooxy | NH-SO2-cyclopropyl |
| 170) | 2-(naphthalen-2-yl)ethyl | tert-butyl | fluorenylidene-aminooxy | NH-SO2-cyclopropyl |
| 171) | cyclohexyl | tert-butyl | fluorenylidene-aminooxy | NH-SO2-cyclopropyl |
| 172) | 2-(adamantan-1-yl)ethyl | tert-butyl | fluorenylidene-aminooxy | NH-SO2-cyclopropyl |
| 173) | adamantan-2-yl | tert-butyl | fluorenylidene-aminooxy | NH-SO2-cyclopropyl |
| 174) | 2-(2-(trifluoromethyl)phenyl)ethyl | tert-butyl | fluorenylidene-aminooxy | NH-SO2-cyclopropyl |

TABLE 2-continued
| Example | Rx | L | W | G |
|---|---|---|---|---|
| 175) | 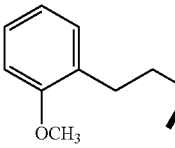 |  | 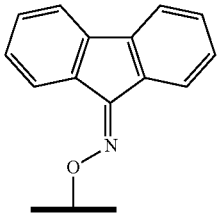 | 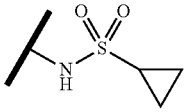 |
| 176) | 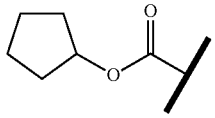 |  | 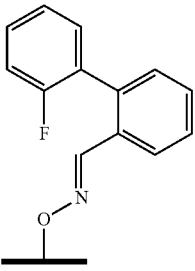 | 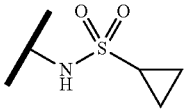 |
| 177) | 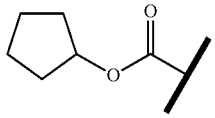 |  | 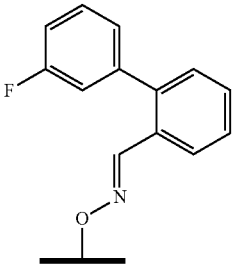 | 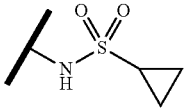 |
| 178) | 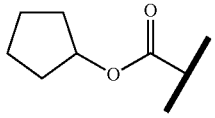 |  | 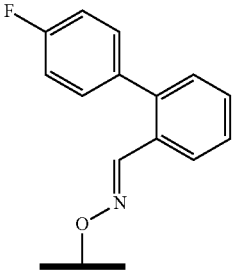 | 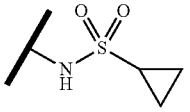 |
| 179) | 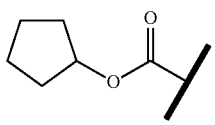 |  | 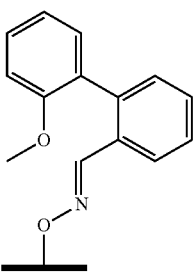 | 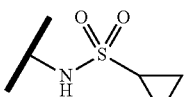 |

TABLE 2-continued
| Example | Rx | L | W | G |
|---|---|---|---|---|
| 180) | 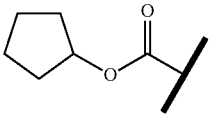 | 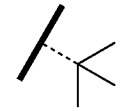 | 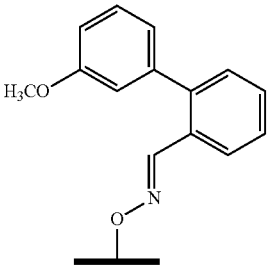 | 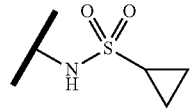 |
| 181) | 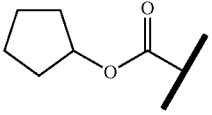 | 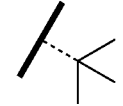 | 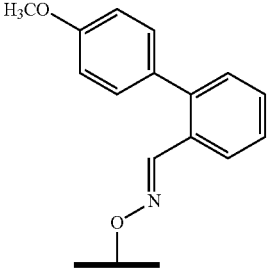 | 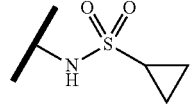 |
| 182) | 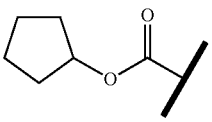 |  | 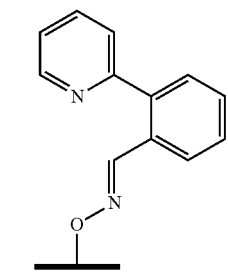 | 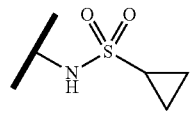 |
| 183) | 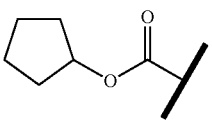 | 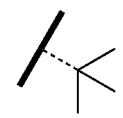 | 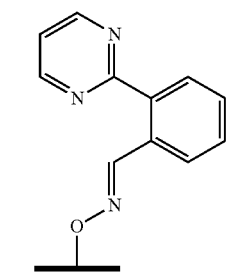 | 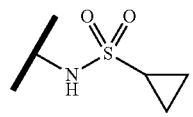 |
| 184) | 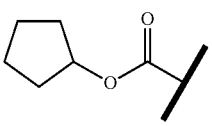 | 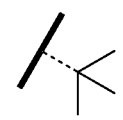 | 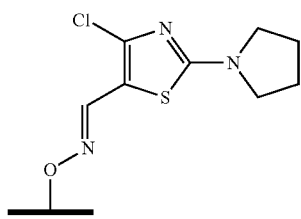 | 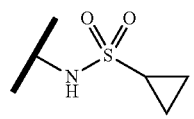 |

TABLE 2-continued
| Example | Rx | L | W | G |
|---|---|---|---|---|
| 185) | 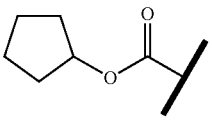 |  | 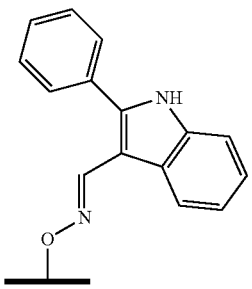 | 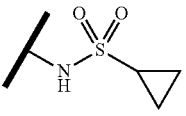 |
| 186) | 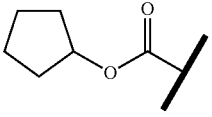 |  | 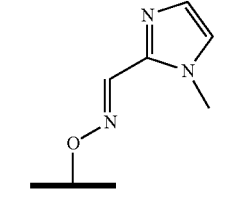 | 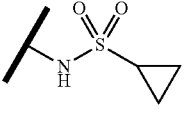 |
| 187) | 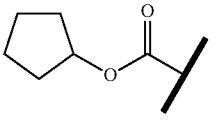 |  | 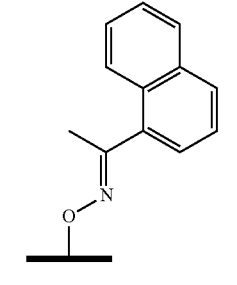 | 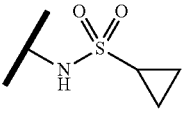 |
| 188) | 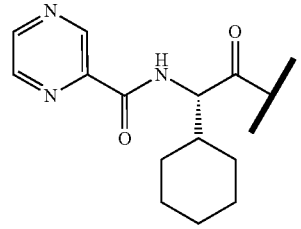 |  | 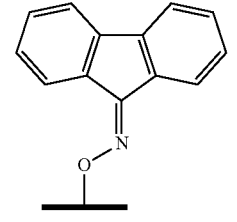 | 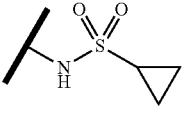 |
| 189) | 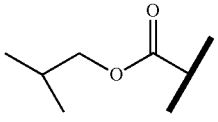 |  | 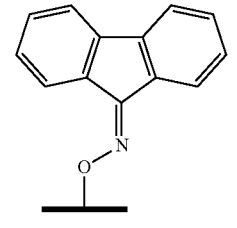 | 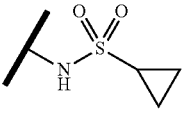 |
| 190) | 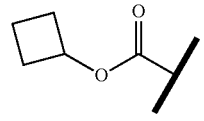 |  | 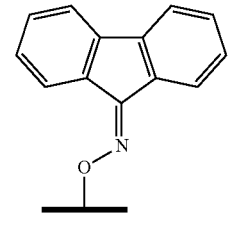 | 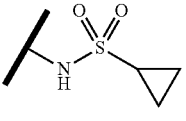 |

TABLE 2-continued

| Example | Rx | L | W | G |
|---|---|---|---|---|
| 191) | cyclobutyl ester | isopropyl | fluorenyl oxime | cyclopropanesulfonamide |
| 192) | cyclopentyl ester | tert-butyl | 6-methoxychroman-4-one oxime | cyclopropanesulfonamide |
| 193) | tert-butyl ester | (R)-1-hydroxyethyl | fluorenyl oxime | cyclopropanesulfonamide |
| 194) | cyclopentyl ester | (R)-1-hydroxyethyl | fluorenyl oxime | cyclopropanesulfonamide |
| 195) | tert-butyl ester | (S)-1-hydroxyethyl | fluorenyl oxime | cyclopropanesulfonamide |
| 196) | cyclopentyl ester | (S)-1-hydroxyethyl | fluorenyl oxime | cyclopropanesulfonamide |
| 197) | tert-butyl ester | 2-hydroxyprop-2-yl | fluorenyl oxime | cyclopropanesulfonamide |

TABLE 2-continued
| Example | Rx | L | W | G |
|---|---|---|---|---|
| 198) | 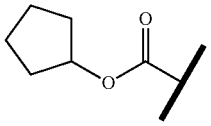 |  | 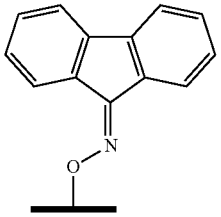 | 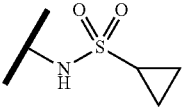 |
| 199) | 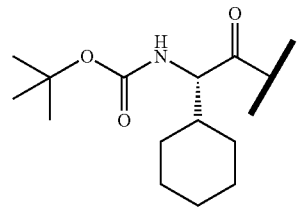 |  | 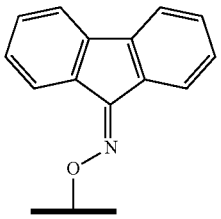 | 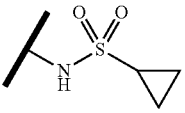 |
| 200) | 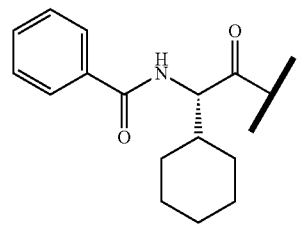 |  | 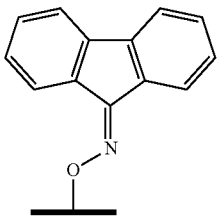 | 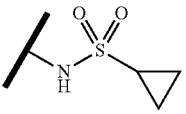 |
| 201) | 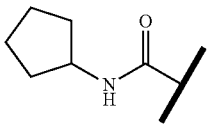 |  | 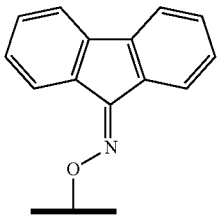 | 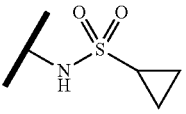 |
| 202) | 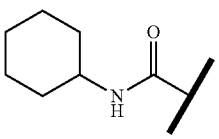 |  | 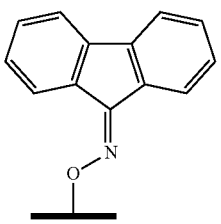 | 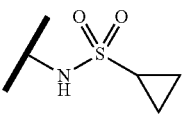 |
| 203) | 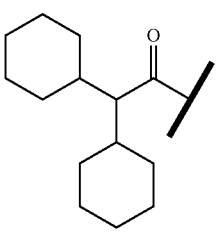 |  | 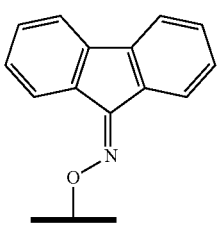 | 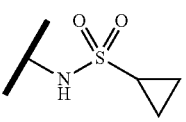 |

TABLE 2-continued

| Example | Rx | L | W | G |
|---|---|---|---|---|
| 204) | | | | |
| 205) | | | | |
| 206) | | | | |
| 207) | | | | |
| 208) | | | | |
| 209) | | | | |

US 8,361,958 B2
TABLE 2-continued
| Example | Rx | L | W | G |
|---|---|---|---|---|
| 210) | 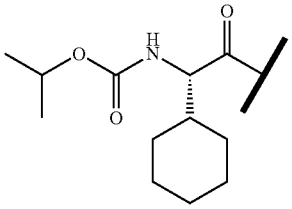 |  | 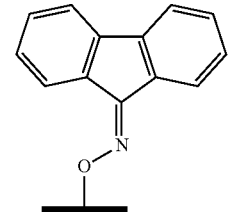 | 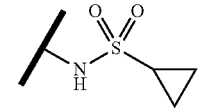 |
| 211) | 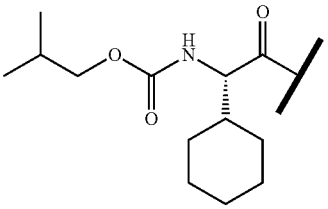 |  | 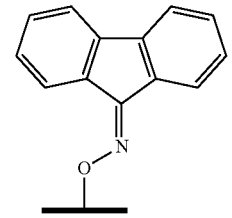 | 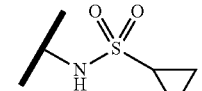 |
| 212) | 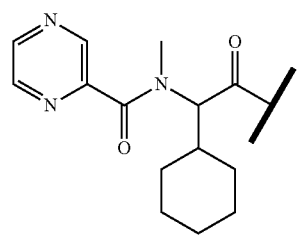 |  | 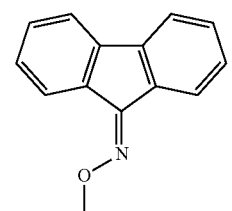 | 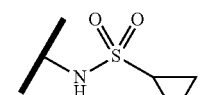 |
| 213) | 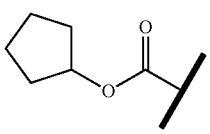 |  | 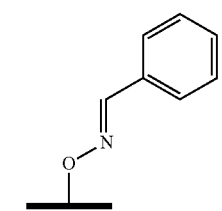 | 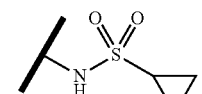 |
| 214) | 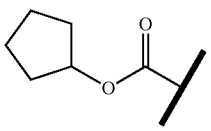 |  | 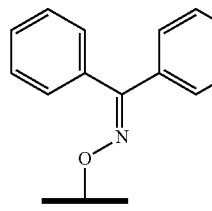 | 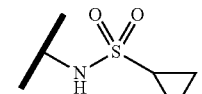 |
| 215) | 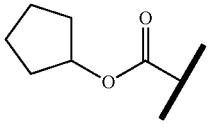 |  | 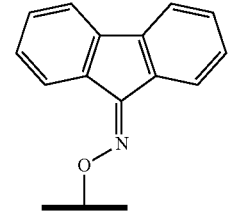 | 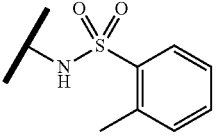 |
| 216) | 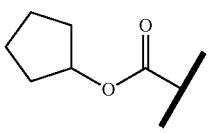 |  | 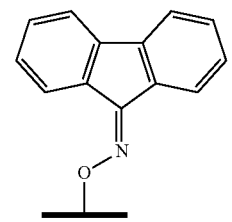 | 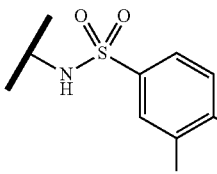 |

TABLE 2-continued
| Example | Rx | L | W | G |
|---|---|---|---|---|
| 217) | 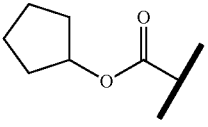 |  | 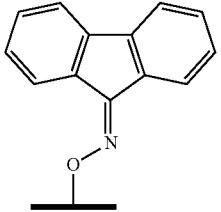 | 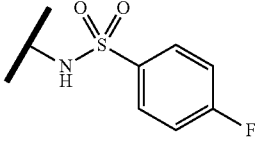 |
| 218) | 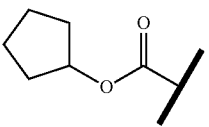 |  | 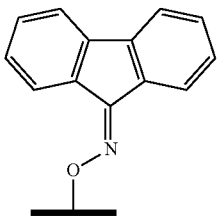 | 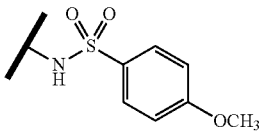 |
| 219) | 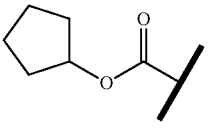 |  | 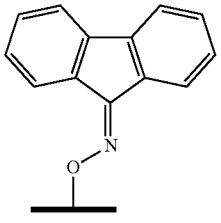 | 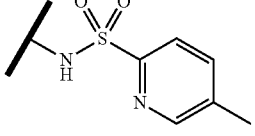 |
| 220) | 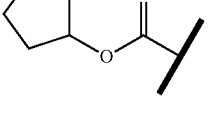 |  | 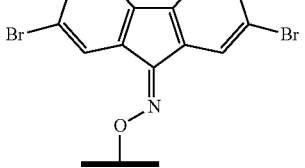 | 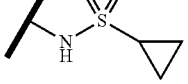 |
| 221) | 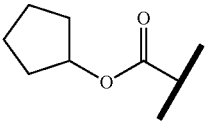 |  | 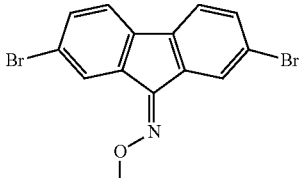 | 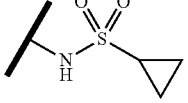 |
| 222) | 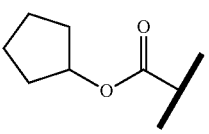 | 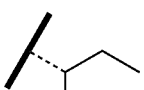 | 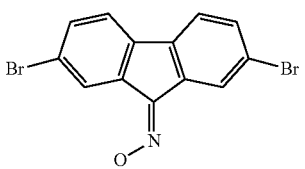 | 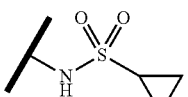 |
| 223) | 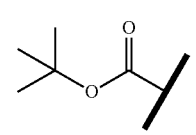 |  | 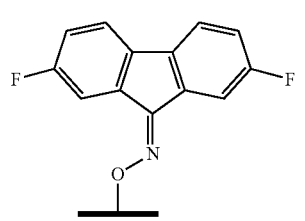 | 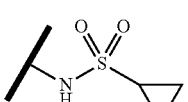 |

TABLE 2-continued

| Example | Rx | L | W | G |
|---|---|---|---|---|
| 224) | (cyclopentyl-O-C(=O)-CH(CH3)-) | (t-butyl) | (2,7-difluorofluorene with =N-O- at 9-position) | (-NH-S(=O)2-cyclopropyl) |
| 225) | (cyclopentyl-O-C(=O)-CH(CH3)-) | (isobutyl) | (2,7-difluorofluorene with =N-O- at 9-position) | (-NH-S(=O)2-cyclopropyl) |
| 226) | (t-butyl-O-C(=O)-CH(CH3)-) | (t-butyl) | (2,7-difluorofluorene with =N-O- at 9-position) | (-NH-S(=O)2-cyclopropyl) |

The present invention also features pharmaceutical compositions comprising a compound of the present invention, or a pharmaceutically acceptable salt, ester or prodrug thereof.

Compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01 90121(A2), or U.S. Pat. No. 6,348,587B1 or WO0160315 or WO0132153 or non-nucleoside inhibitors such as, for example, benzimidazole polymerase inhibitors described in EP 1162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agents include but are not limited to therapies for disease caused by hepatitis B (HBV) infection such as, for example, adefovir, lamivudine, and tenofovir or therapies for disease caused by human immunodeficiency virus (HIV) infection.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenfovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the pharmaceutical compositions of the present invention may further comprise another anti-viral, anti-bacterial, anti-fungal or anti-cancer agent, or an immune modulator, or another therapeutic agent.

According to still another embodiment, the present invention includes methods of treating viral infection such as, but not limited to, hepatitis C infections in a subject in need of such treatment by administering to said subject an effective amount of a compound of the present invention or a pharmaceutically acceptable salt, ester, or prodrug thereof.

According to a further embodiment, the present invention includes methods of treating hepatitis C infections in a subject in need of such treatment by administering to said subject an anti-HCV virally effective amount or an inhibitory amount of a pharmaceutical composition of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "anti-cancer agent" refers to a compound or drug capable of preventing or inhibiting the advancement of cancer. Examples of such agents include cis-platin, actinomycin D, doxorubicin, vincristine, vinblastine, etoposide, amsacrine, mitoxantrone, tenipaside, taxol, colchicine, cyclosporin A, phenothiazines or thioxantheres.

The term "anti-fungal agent" shall used to describe a compound which may be used to treat a fungus infection other than 3-AP, 3-AMP or prodrugs of 3-AP and 3-AMP according to the present invention. Anti-fungal agents according to the present invention include, for example, terbinafine, fluconazole, itraconazole, posaconazole, clotrimazole, griseofulvin, nystatin, tolnaftate, caspofungin, amphotericin B, liposomal amphotericin B, and amphotericin B lipid complex.

The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

The term "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a monovalent group derived from a hydrocarbon moiety by the removal of a single hydrogen atom wherein the hydrocarbon moiety has at least one carbon-carbon double bond and contains from two to six, or two to eight carbon atoms, respectively. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety by the removal of a single hydrogen atom wherein the hydrocarbon moiety has at least one carbon-carbon triple bond and contains from two to six, or two to eight carbon atoms, respectively. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom where the saturated carbocyclic ring compound has from 3 to 8, or from 3 to 12, ring atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom where the carbocyclic ring compound has from 3 to 8, or from 3 to 12, ring atoms, respectively. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxy, —NO₂, —CN, —NH₂, N₃, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH₂, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —OCO₂—$C_1$-$C_{12}$-alkyl, —OCO₂—$C_2$-$C_{12}$-alkenyl, —OCO₂—$C_2$-$C_{12}$-alkynyl, —OCO₂—$C_3$-$C_{12}$-cycloalkyl, —OCO₂-aryl, —OCO₂-heteroaryl, —OCO₂-heterocycloalkyl, —OCONH₂, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —NHCO₂—$C_1$-$C_{12}$-alkyl, —NHCO₂—$C_2$-$C_{12}$-alkenyl, —NHCO₂—$C_2$-$C_{12}$-alkynyl, —NHCO₂—$C_3$-$C_{12}$-cycloalkyl, —NHCO₂-aryl, —NHCO₂— heteroaryl, —NHCO₂— heterocycloalkyl, —NHC(O)NH₂, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH₂, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH₂, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —SO₂NH₂, —SO₂NH—$C_1$-$C_{12}$-alkyl, —SO₂NH—$C_2$-$C_{12}$-alkenyl, —SO₂NH—$C_2$-$C_{12}$-alkynyl, —SO₂NH—$C_3$-$C_{12}$-cycloalkyl, —SO₂NH-aryl, —SO₂NH-heteroaryl, —SO₂NH— heterocycloalkyl, —NHSO₂—$C_1$-$C_{12}$-alkyl, —NHSO₂—$C_2$-$C_{12}$-alkenyl, —NHSO₂—$C_2$-$C_{12}$-alkynyl, —NHSO₂—$C_3$-$C_{12}$-cycloalkyl, —NHSO₂-aryl, —NHSO₂-heteroaryl, —NHSO₂-heterocycloalkyl, —CH₂NH₂, —CH₂SO₂CH₃, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO₂, —CN, or —NH₂.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, and methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$). Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject (e.g., resulting in at least 10%, preferably at least 50%, more preferably at least 80%, and most preferably at least 90% or 95%, reduction in viral load). As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject (e.g., resulting in at least 10%, preferably at least 50%, more preferably at least 80%, and most preferably at least 90% or 95%, reduction in viral load). It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DCM for dichloromethane;
DIAD for diisopropyl azodicarboxylate;
DIBAL-H for diisobutylaluminum hydride;
DIEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DUPHOS for

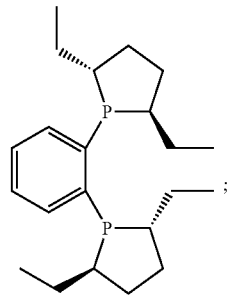 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for 0 (7-Azabenzotriazole-1-yl)-N,N,N',N'-tetramethyluronium hexafluorophosphate;
Hoveyda's Cat. for Dichloro(o-isopropoxyphenylmethylene) (tricyclohexylphosphine)ruthenium(II);
KHMDS is potassium bis(trimethylsilyl)amide;
Ms for mesyl;
NMM for N-4-methylmorpholine;
PyBrOP for Bromo-tri-pyrrolidino-phosphonium hexafluorophosphate;
Ph for phenyl;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran;
TLC for thin layer chromatography;
TPP or $PPh_3$ for triphenylphosphine;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

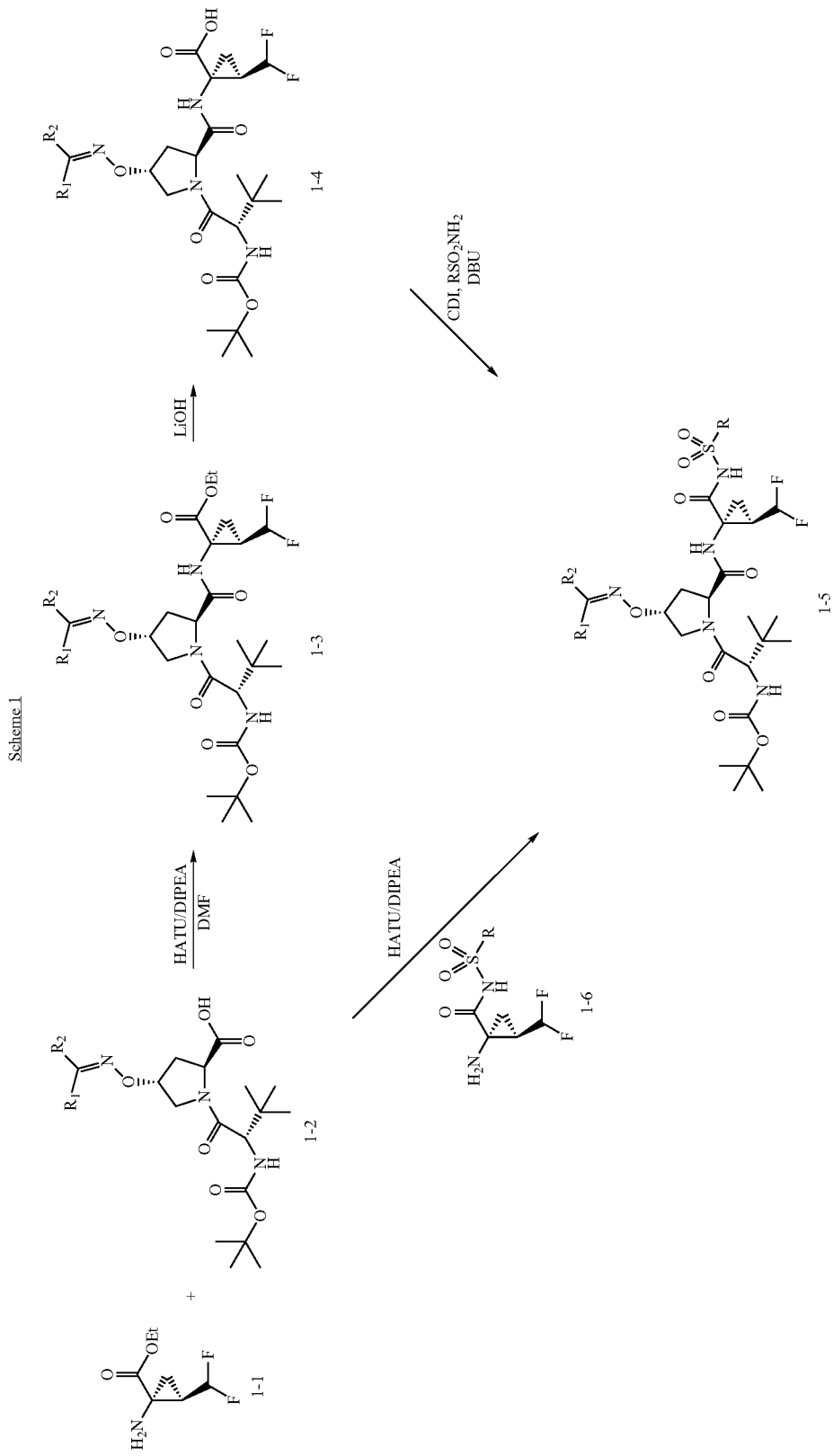
Scheme 1

The general synthetic strategies of compounds of present invention are shown in Scheme 1. Difluoromethyl P1 aminoacid compound 1-1 was coupled with oxime P2-P3 intermediate 1-2 to give ester 1-3, which was hydrolyzed to give carboxylic acid 1-4. The conversion of acid 1-4 to sulfonimide compound 1-5 was achieved using CDI and sulfonamide $RSO_2NH_2$. Final compound 1-5 was also prepared via direct coupling of oxime P2-P3 intermediate 1-2 with difluoromethyl P1 sulfonimide compound 1-6. The syntheses of oxime P2-P3 intermediates and difluoromethyl P1 derivatives are described in the following schemes.

The synthesis of difluoromethyl P1 (1-1) is outlined in Scheme 2. Mono-Boc amino acid ester was further protected as bis-Boc aminoacid ester 2-2. Oxidative cleavage of compound 2-2 resulted in the aldehyde 2-3, which was then converted to difluoromethyl compound 2-4 using aminosulfur trifluoride derivatives such as diethylminosulfur trifluoride (DAST). Deprotection of 2-4 using HCl afforded the desired difluoromethyl P1 compound 1-1.

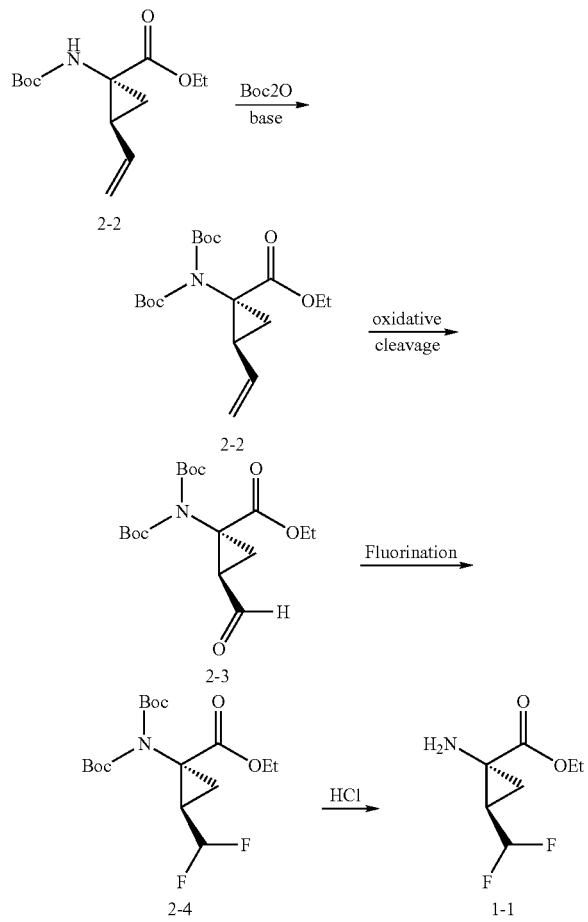

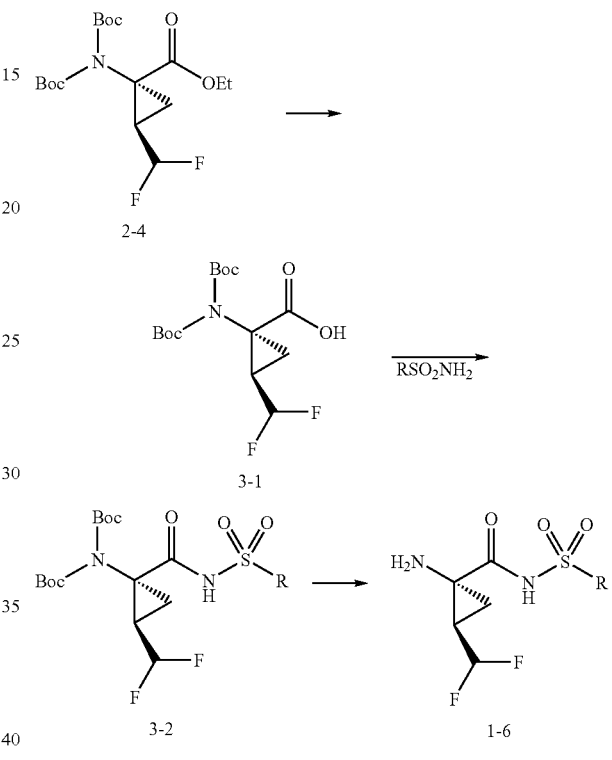

Difluoromethyl P1 sulfonimide derivative 1-6 was prepared as shown in Scheme 3. The hydrolysis of compound 2-4 gave the acid 3-1, which was converted to 3-2 using CDI/$RSO_2NH_2$/DBU or HATU/DIPEA/$RSO_2NH_2$. Deprotection of 3-2 afforded the desired intermediate 1-6.

Scheme 4

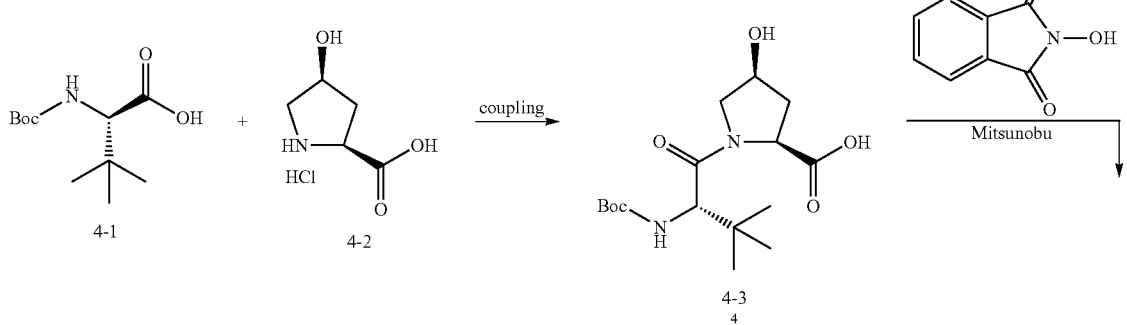

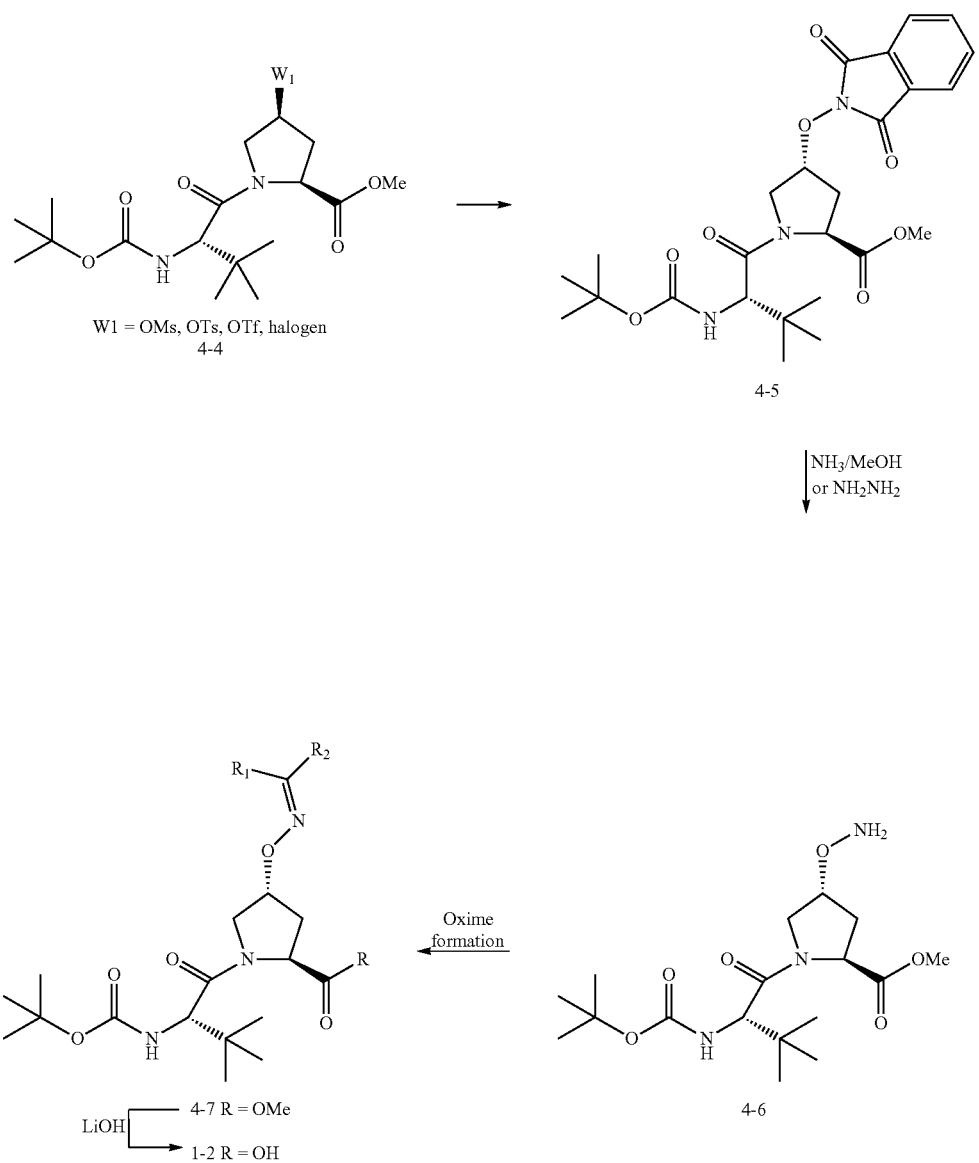

A general method to prepare oxime intermediate 1-2 is outlined in Scheme 4. The acyclic dipeptide precursor 4-3 was synthesized from Boc-L-tert-leucine 4-1 and cis-L-hydroxyproline methyl ester 4-2. The coupling of compound 4-3 with commercially available hydroxyphthalimide using Mitsunobu conditions followed by deprotection of the phthalimide moiety with ammonia or hydrazine gave hydroxy amine 4-6. For further details on the Mitsunobu reaction, see O. Mitsunobu, Synthesis 1981, 1-28; D. L. Hughes, Org. React. 29, 1-162 (1983); D. L. Hughes, Organic Preparations and Procedures Int. 28, 127-164 (1996); and J. A. Dodge, S. A. Jones, Recent Res. Dev. Org. Chem. 1, 273-283 (1997). Alternatively, intermediate 4-6 was made by converting hydroxy intermediate 4-3 to a suitable leaving group such as, but not limited to OMs, OTs, OTf, bromide, or iodide; followed by the deprotection of the phthalimide moiety with ammonia or hydrazine. Oximes 4-7 was prepared by treating hydroxy amine 4-6 with appropriate aldehyde or ketone optionally in the presence of an acid. Subsequent removal of the acid protecting group afforded compounds of formula 1-2.

Scheme 5

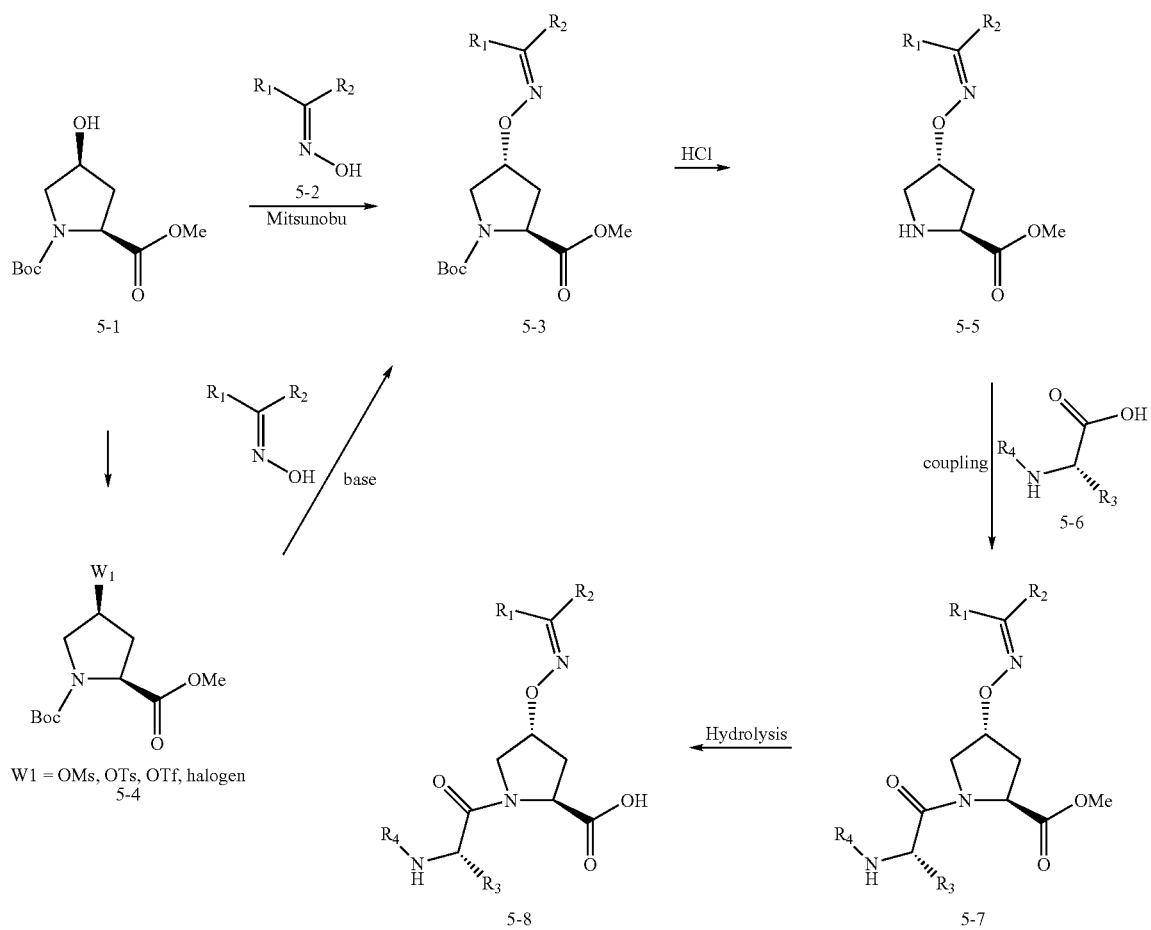

Another general method to prepare oxime intermediates (with formula 1-2 or 5-8) is shown in Scheme 5. Boc-cis-L-hydroxyproline methyl ester 5-1 was coupled with oxime 5-2 under Mitsunobu conditions to give intermediate 5-3. Alternatively, compound 5-3 was made through SN2 replacement of activated hydroxyl group of compound 5-4. Deprotection of intermediate 5-3 gave free amine 5-5 (as HCl salt), which was coupled with amino acid 5-6 to give ester 5-7. The final hydrolysis of compound 5-7 afforded the desired oxime intermediate 5-8.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

Compound of Formula VII, Wherein A=T-Butyloxycarbonyl L=T-Butyl $R_1$ and $R_2$ Taken Together with the Carbon Atom to which they are Attached are

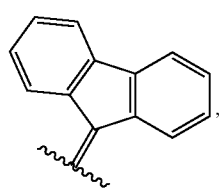 [SMILES: *=C1c2ccccc2-c2ccccc21]

and G=OH

Step 1A

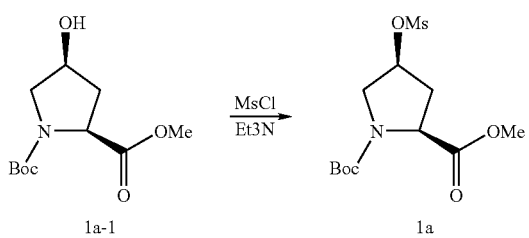

To a solution of Boc cis-L-hydroxyproline methyl ester (2 g, 8.15 mmol) 1a-1 and Et3N (1.7 ml, 12.23 mmol) in dichloromethane at 0° C. was added slowly MsCl (0.7 ml, 8.96 mmol). The resulting mixture was stirred at room temperature for 1~2 h, diluted with EtOAc, washed with brine, dried (MgSO$_4$) and concentrated in vacuo to dryness to give crude 1a which was directly used in next step.

Step 1B

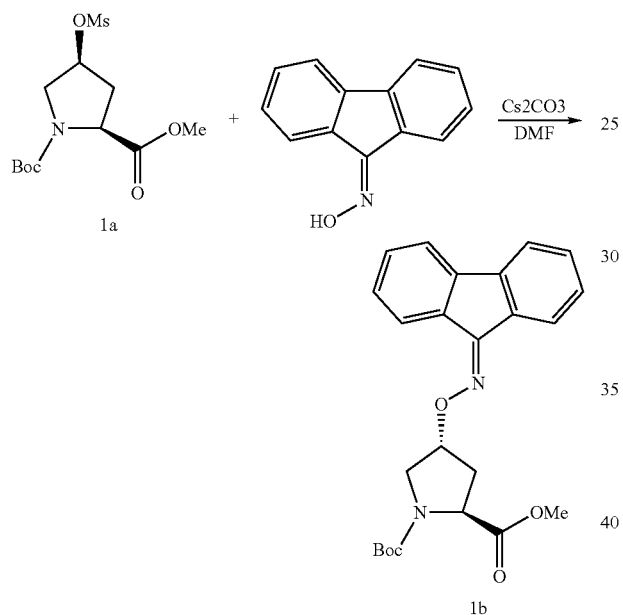

A mixture of the above crude 1a, 9H-fluoren-9-one oxime (1.8 g, 8.97 mmol), cesium carbonate (4 g, 12.2 mmol) and DMF (12 ml) was stirred at 50° C. for 20 h, diluted with EtOAc, washed with brine, dried (MgSO$_4$) and concentrated in vacuo. The residue was purified by silica gel chromatography (Hexane/EtOAc=9:1 to 4:1) to afford 1b (2.736 g). MS (ESI): m/z 323.11 (M-Boc); 423.15 (M+H).

Step 1C

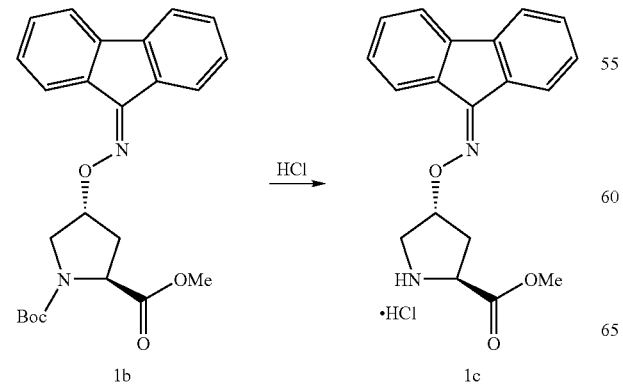

A solution of compound 1b (960 mg, 2.2 mmol) in dichloromethane (3 ml) was treated with 4N HCl in 1,4-dioxane (5 ml, 20 mmoL). The mixture was stirred at room temperature for an hour, concentrated to dryness to afford 1c (~100%).

Step 1D

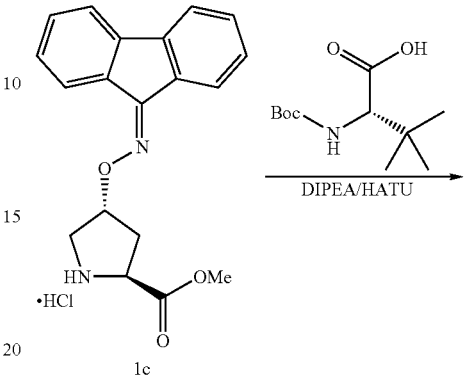

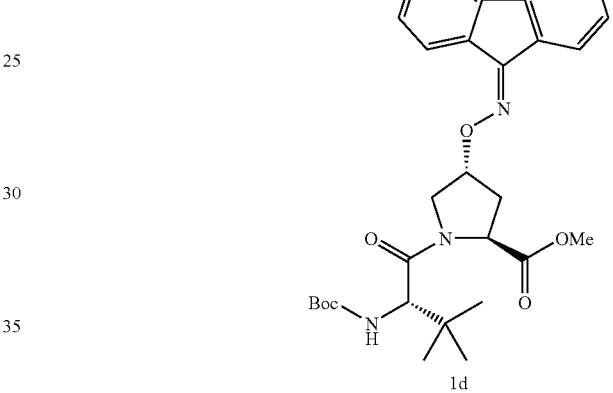

To a solution of 1c (2.2 mmol), Boc-L-tert-leucine (560 mg, 2.42 mmol) and DIPEA (1.15 ml, 6.6 mmol) in DMF (10 ml) at 0° C. was added HATU (920 mg, 2.42 mmol). The mixture was stirred at room temperature for 18 h, diluted with EtOAc and washed with half-sat.-aq. NaCl four times. The organic phase was dried over anhydrous MgSO$_4$, filtered, and then concentrated in vacuo. The residue was purified by silica gel column (Hexane/EtOAc=4:1 to 2:1) to afford compound 1d (1.16 g). MS (ESI): m/z 536.23 (M+H).

Step 1E

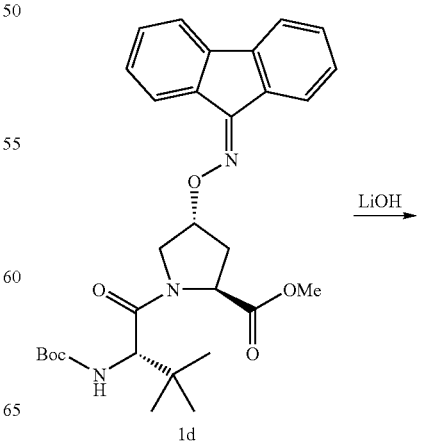

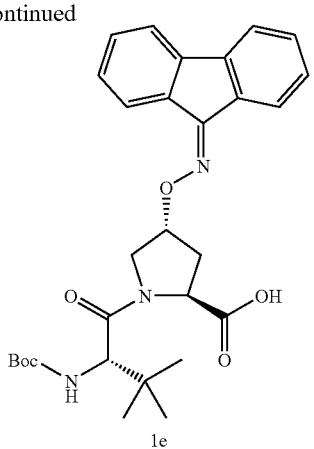

1e

To a solution of compound 1d (1.06 g, 1.98 mmol) in THF/MeOH/water (20 ml-10 ml-10 ml) was added lithium hydroxide hydrate (494 mg, 11.78 mmol). The mixture was stirred at room temperature for 18 hours. Most organic solvents were evaporated in vacuo, and the resulting residue was diluted with water and acidified to pH 5 to 6. The mixture was extracted with EtOAc three times. The combined organic extracts were dried (MgSO$_4$), filtered and concentrated in vacuo to afford 1e (~100%). MS (ESI): m/z 528.32 (M+Li).
Step 1F

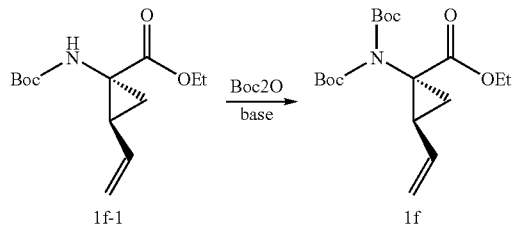

To a solution of compound 1f-1 (6.6 g, 25.85 mmol) in THF (115 ml) at −78° C. was added slowly NaHMDS (1.0M in THF, 28.5 ml, 28.5 mmol). After the mixture was stirred at −78° C. for an hour, Boc2O (6.8 g, 1.2 eq.) in THF (15 ml) was added. The resulting mixture was stirred, and the temperature allowed to rise gradually to rt overnight. The reaction mixture was diluted with EtOAc, washed with brine (2×), dried (MgSO4) and concentrated in vacuo. The residue was purified by silica gel chromatography (Hexane/EtOAc=1:0 to 85:15) to afford 1f (8.05 g).
Step 1G

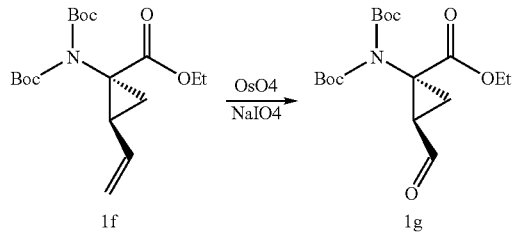

To a solution of compound 1f (0.5 g, 1.4 mmol) in iso-propanol (5 ml) was added NaIO4 (0.9 g, 4.2 mmol), followed by water (5 ml). To this vigorously stirred mixture was added OsO4 (0.4% aq. solution, 0.22 m, 2.5% eq.). The resulting mixture was stirred at rt for 4 h, diluted with EtOAc, washed with aq. NaHCO3, aq. Na2S2O3, brine, dried (MgSO4) and concentrated in vacuo. The residue was purified by silica gel chromatography (Hexane/EtOAc=1:0 to 85:15) to afford 1g (0.37 g).
Step 1H

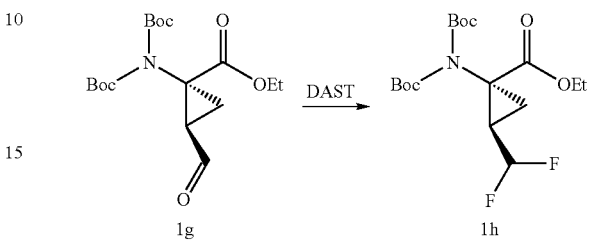

To a solution of compound 1g (2.9 g, 8.1 mmol) in dichloromethane (25 ml) at −78° C. was added diethylaminosulfur trifluoride (DAST) (2.7 ml, 20.25 mmol). The resulting mixture was stirred at −78° C. for an hour, then the temperature allowed to rise gradually to rt over 6 h, diluted with EtOAc, washed with aq. NaHCO3 (2×), brine, dried (MgSO4) and concentrated in vacuo. The residue was purified by silica gel chromatography (Hexane/EtOAc=1:0 to 85:15) to afford 1 h (1.49 g). Recovered starting material 1g (1.2 g).
Step 1I

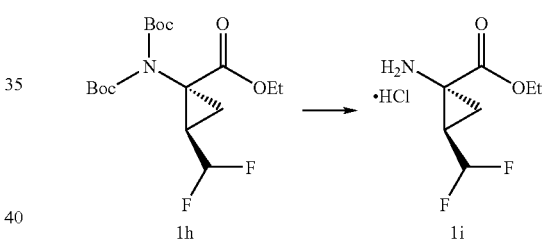

A solution of compound 1h (491 mg, 1.29 mmol) in dichloromethane (1 ml) was treated with 4N HCl in 1,4-dioxane (6 ml, 24 mmoL). The mixture was stirred at room temperature for an hour, concentrated to dryness to afford 1i (~100%).
Step 1J

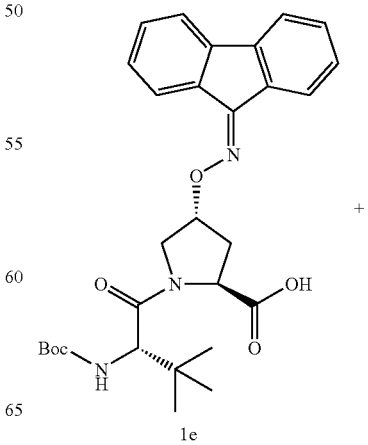

1e

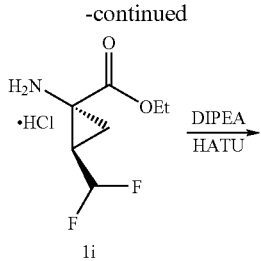

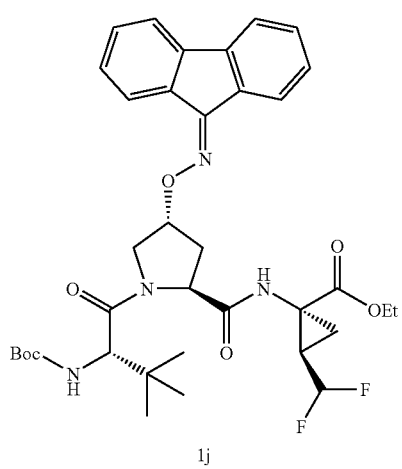

To a solution of 1i (1.29 mmol), compound 1e (657 mg, 1.26 mmol) and DIPEA (0.7 ml, 3 eq.) in DMF (6 ml) at 0° C. was added HATU (540 mg, 1.42 mmol). The mixture was stirred at room temperature for 18 h, diluted with EtOAc and washed with half-sat.-aq. NaCl four times. The organic phase was dried over anhydrous MgSO$_4$, filtered, and then concentrated in vacuo. The residue was purified by silica gel column (Hexane/EtOAc=8:2 to 6:4) to afford compound 1j (790 mg). MS (ESI): m/z 683.17 (M+H).

Step 1K

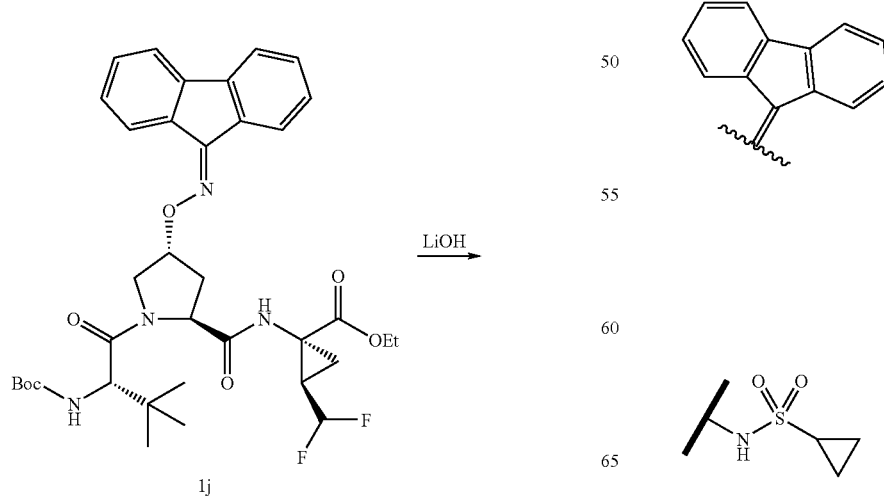

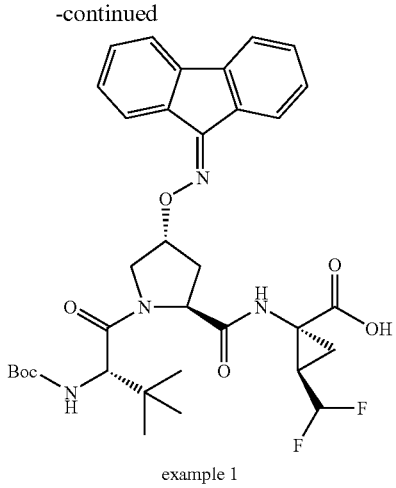

example 1

To a solution of compound 1j (770 mg, 1.12 mmol) in THF/MeOH (20 ml-10 ml) was added aq. lithium hydroxide hydrate 1.0M, 10 ml, 10 mmol). The mixture was stirred at room temperature for 18 hours. Most organic solvents were evaporated in vacuo, and the resulting residue was diluted with water and acidified to pH 5 to 6. The mixture was extracted with EtOAc three times. The combined organic extracts were dried (MgSO$_4$), filtered and concentrated in vacuo to afford the title compound (100%). MS (ESI): m/z 655.15 (M+H); 661.15 (M+Li).

Example 2

Compound of Formula VII, Wherein A=T-Butyloxycarbonyl L=T-Butyl R$_1$ and R$_2$ Taken Together with the Carbon Atom to which they are Attached are and G=

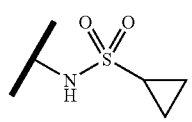

Method I

Step 2A

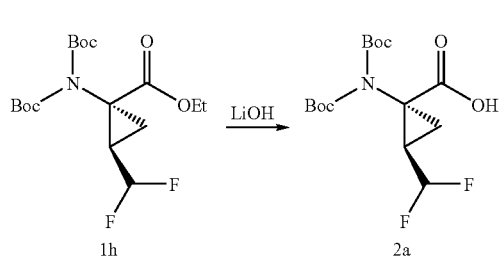

Step 2C

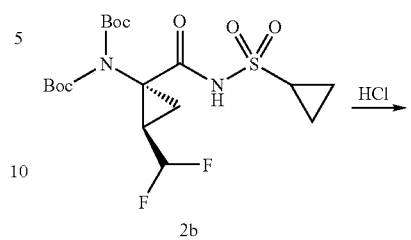

To a solution of compound 1h (381 mg, 1.4 mmol) in THF/MeOH (24 ml-12 ml) was added aq. lithium hydroxide hydrate 1.0M, 12 ml, 12 mmol). The mixture was stirred at room temperature for 2 days. Most organic solvents were evaporated in vacuo, and the resulting residue was diluted with water and acidified to pH 5 to 6. The mixture was extracted with EtOAc three times. The combined organic extracts were dried (MgSO₄), filtered and concentrated in vacuo to afford compound 2a (~100%), directly used in next step.

Step 2B

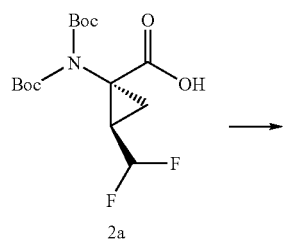

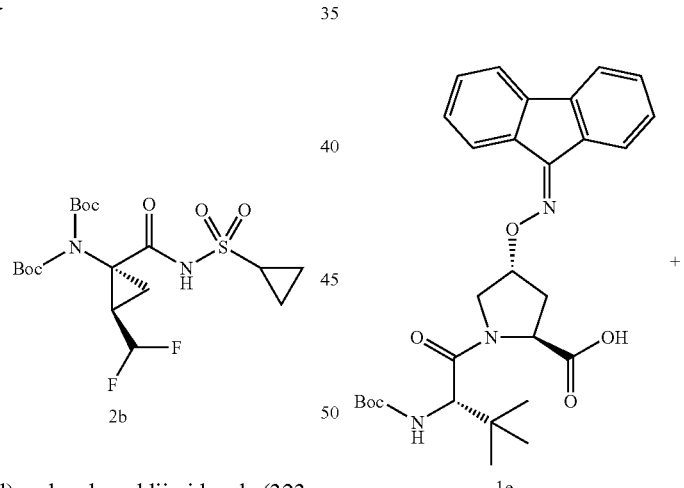

A solution of above compound 2h in dichloromethane (1 ml) was treated with 4N HCl in 1,4-dioxane (4 ml, 16 mmol). The mixture was stirred at room temperature for an hour, concentrated to dryness to afford 2c, directly used in next step.

Step 2D

Compound 2a (1.33 mmol) and carbonyldiimidazole (323 mg, 2.mmol) were dissolved in 5 ml of anhydrous DMF and the resulting solution was stirred at 40° C. for 1 hour. Cyclopropylsulfonamide (483 mg, 4 mmol) was added to the reaction mixture followed by DBU (0.26 ml, 1.7 mmol). The reaction mixture was stirred at 40° C. for 18 hours. The reaction mixture was diluted with ethyl acetate and washed with half-saturated-aqueous NaCl solution four times. The organic layer was dried over anhydrous (MgSO₄) and concentrated in vacuo to give compound 2b, which was directly used in next step 2C.

Alternatively, compound 2b was made from compound 2a using coupling reagent HATU/base and cyclopropylsulfonamide.

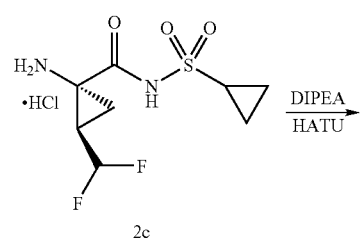

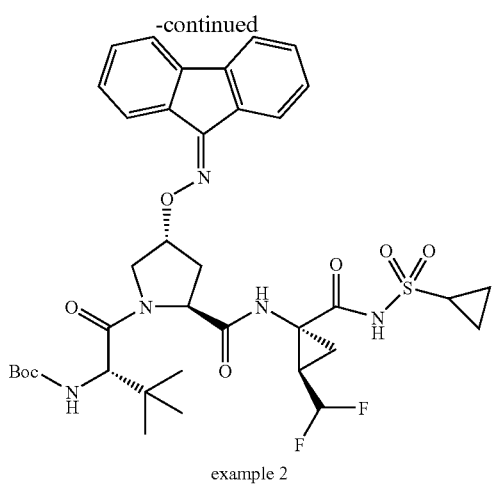

example 2

To a solution of compound 1e (52 mg, 0.1 mmol) 2c (1 eq.), and DIPEA (0.18 ml, 1 mmol) in DMF (2.5 ml) at 0° C. was added HATU (50 mg, 0.13 mmol). The mixture was stirred at room temperature for 18 h, diluted with EtOAc and washed with half-sat.-aq. NaCl four times. The organic phase was dried over anhydrous MgSO$_4$, filtered, and then concentrated in vacuo. The residue was purified by preparative HPLC to afford the title compound (40 mg). MS (ESI); m/z 758.28 (M+H).

Method II

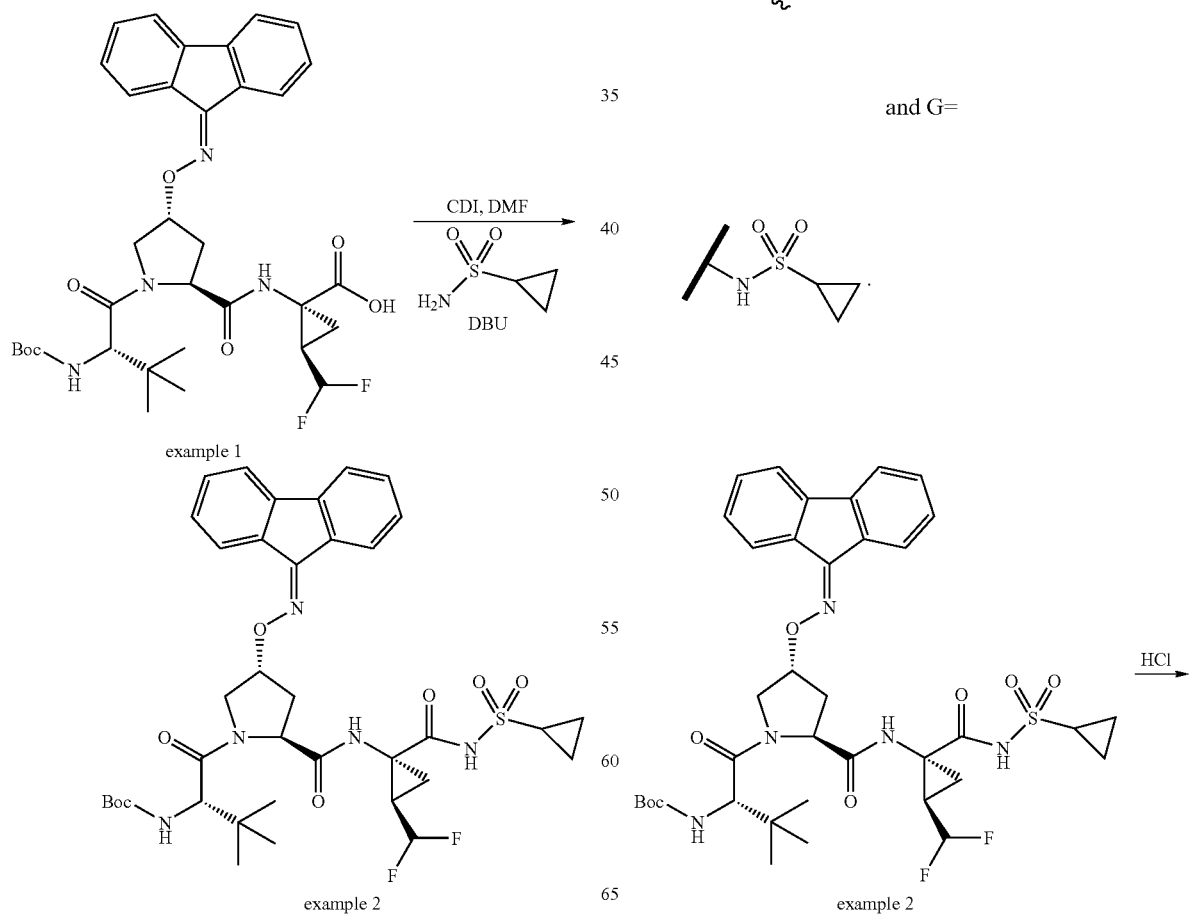

example 1 example 2 example 2

Compound example 1 (697 mg, 1.06 mmol) and carbonyl-diimidazole (343 mg, 2.1 mmol) were dissolved in 10 ml of anhydrous DMF and the resulting solution was stirred at 40° C. for 1 hour. Cyclopropylsulfonamide (385 mg, 3.18 mmol) was added to the reaction followed by DBU (0.24 ml, 1.6 mmol). The reaction mixture was stirred at 40° C. for 2 hours. The reaction mixture was diluted with ethyl acetate and washed with half-saturated-aqueous NaCl solution three times. The organic layer was dried over anhydrous (MgSO4) and concentrated in vacuo. The residue was purified by silica gel chromatography (Hexanes/EtOAc=1:1 to 0:1) to give the title compound (750 mg). MS (ESI); m/z 758.28 (M+H).

Example 3

Compound of Formula VII, Wherein A=H, L=T-Butyl R$_1$ and R$_2$ Taken Together with the Carbon Atom to which they are Attached are

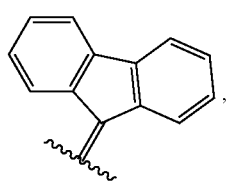 [SMILES: *=C1c2ccccc2-c2ccccc21]

and G=

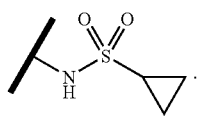

-continued

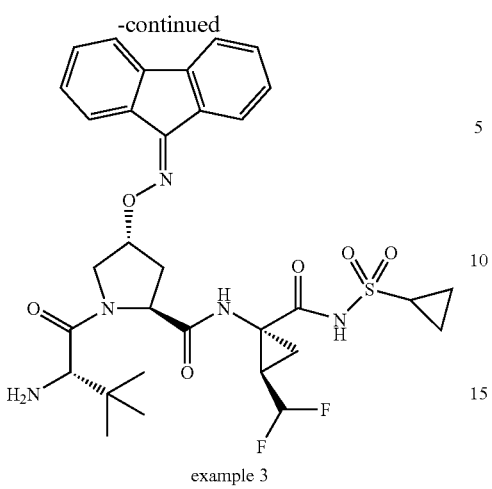

example 3

A solution of compound example 2 (25 mg) in dichloromethane (0.25 ml) was treated with 4N HCl in 1,4-dioxane (1 ml, 4 mmol). The mixture was stirred at room temperature for an hour, concentrated to dryness to afford the title compound (HCL salt). MS (ESI): 658.21 (M+H).

Example 4

Compound of Formula VII, Wherein A=Cyclopentyloxycarbonyl L=T-Butyl $R_1$ And $R_2$ Taken Together with the Carbon Atom to which they are Attached are

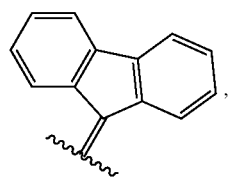 [SMILES: *=C1c2ccccc2-c2ccccc21]

and G=

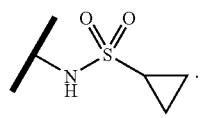

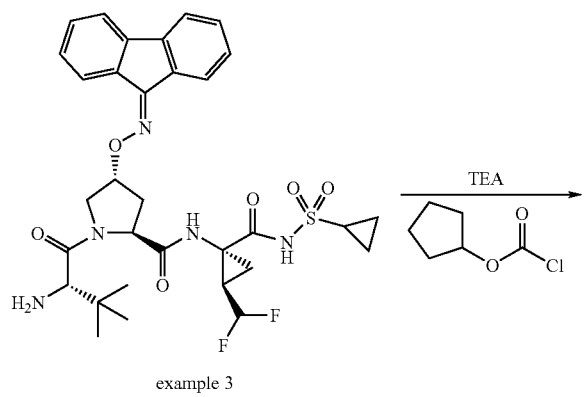

example 3

-continued

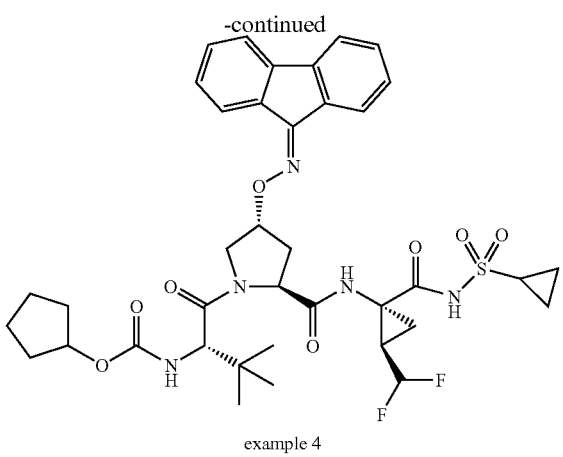

example 4

To a solution of compound example 3 (0.014 mmol) and triethylamine (0.08 ml, 40 eq.) in dichloromethane (1.5 ml) at 0° C. was added cyclopentyl chloroformate (1.5M in toluene, 0.09 ml, 0.135 mmol). The resulting mixture was then stirred at rt for 0.5 to 2 h, diluted with EtOAc, washed with brine (2×), dried (MgSO4) and concentrated in vacuo. The residue was purified by preparative HPLC to afford the title compound (4 mg). MS (ESI); m/z 770.64 (M+H).

Example 5

Compound of formula VII, Wherein A=Cyclobutyloxycarbonyl L=T-Butyl $R_1$ and $R_2$ Taken Together with the Carbon Atom to which they are Attached are

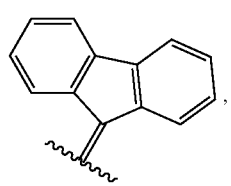 [SMILES: *=C1c2ccccc2-c2ccccc21]

and G=

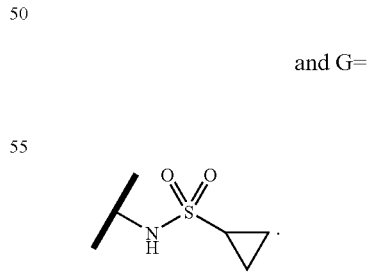

The title compound was prepared by using the same procedure as described in example 4. MS (ESI): m/z 756.27 (M+H).

Example 6

Compound of Formula VII, Wherein
A=Iso-Propyloxycarbonyl L=T-Butyl $R_1$ and $R_2$
Taken Together with the Carbon Atom to which they
are Attached are

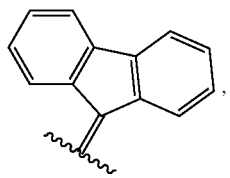 [SMILES: *=C1c2ccccc2-c2ccccc21]

and G=

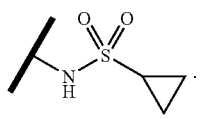

The title compound was prepared by using the same procedure as described in example 4. MS (ESI): m/z 744.16 (M+H).

Example 7

Compound of Formula VII, Wherein
A=Ethoxycarbonyl L=T-Butyl $R_1$ and $R_2$ Taken
Together with the Carbon Atom to which they are
Attached are

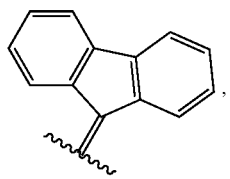 [SMILES: *=C1c2ccccc2-c2ccccc21]

and G=

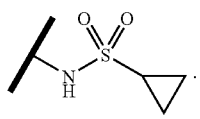

The title compound was prepared by using the same procedure as described in example 4. MS (ESI): m/z 730.24 (M+H).

Example 8

Compound of Formula VII, Wherein
A=Methoxycarbonyl L=T-Butyl $R_1$ and $R_2$ Taken
Together with the Carbon Atom to which they are
Attached are

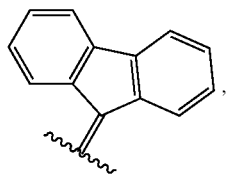 [SMILES: *=C1c2ccccc2-c2ccccc21]

and G=

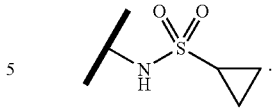

The title compound was prepared by using the same procedure as described in example 4. MS (ESI): m/z 716.25 (M+H).

Example 9

Compound of Formula VII, Wherein A=

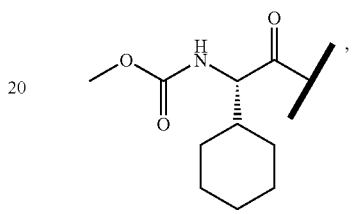

L=T-Butyl $R_1$ and $R_2$ Taken Together with the
Carbon Atom to which they are Attached are

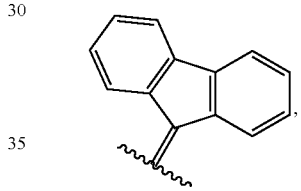

and G=

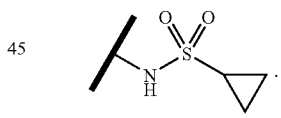

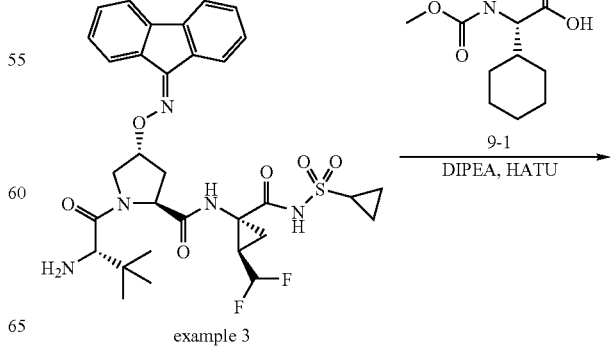

-continued

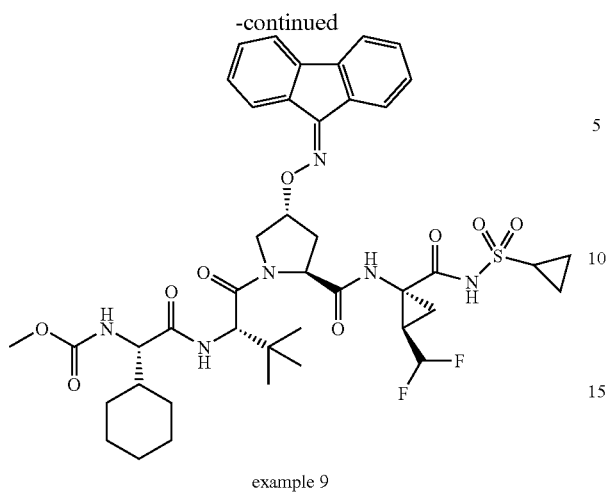

example 9

To a solution of compound 9-1 (5.5 mg, 0.025 mmol, compound example 3 (0.013 mmol) and DIPEA (0.22 ml, 0.25 mmol) in DMF (1 ml) at 0° C. was added HATU (10 mg, 0.025 mmol). The mixture was stirred at room temperature for 18 h, diluted with EtOAc and washed with half-sat.-aq. NaCl four times. The organic phase was dried over anhydrous MgSO$_4$, filtered, and then concentrated in vacuo. The residue was purified by preparative HPLC to afford the title compound (8 mg). MS (ESI); m/z 855.44 (M+H).

Example 10

Compound of Formula VII, Wherein A=

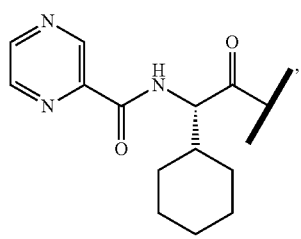

L=T-Butyl R$_1$ and R$_2$ Taken Together with the Carbon Atom to which they are Attached are

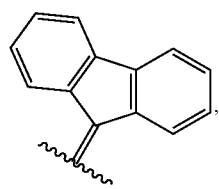 [SMILES: *=C1c2ccccc2-c2ccccc21]

and G=

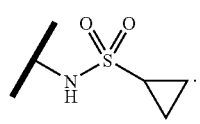

The title compound was prepared by using the same procedure as described in example 9. MS (ESI): m/z 903.43 (M+H)

Example 11

Compound of Formula VII, Wherein A=

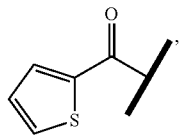

L=T-Butyl R$_1$ and R$_2$ Taken Together with the Carbon Atom to which they are Attached are

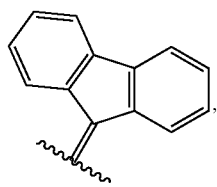 [SMILES: *=C1c2ccccc2-c2ccccc21]

and G=

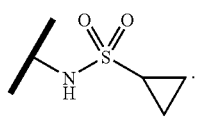

The title compound was prepared by using the same procedure as described in example 9. MS (ESI): m/z 768.57 (M+H).

Example 12

Compound of Formula VII, Wherein A=

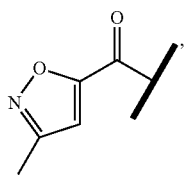

L=T-Butyl R$_1$ and R$_2$ Taken Together with the Carbon Atom to which they are Attached are

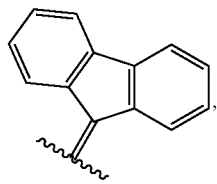

and G=

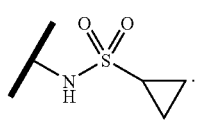

The title compound was prepared by using the same procedure as described in example 9. MS (ESI): m/z 767.20 (M+H).

Example 13

Compound of Formula VII, Wherein A=

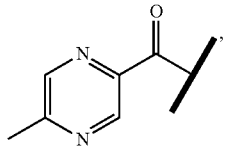

L=T-Butyl $R_1$ and $R_2$ Taken Together with the Carbon Atom to which they are Attached are

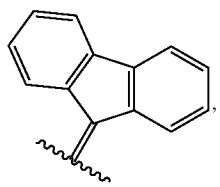 [SMILES: *=C1c2ccccc2-c2ccccc21]

and G=

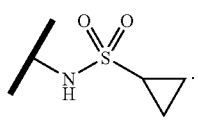

The title compound was prepared by using the same procedure as described in example 9. MS (ESI): m/z 778.20 (M+H).

Example 14

Compound of Formula VII, Wherein A=

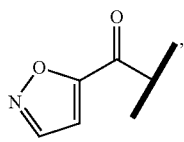

L=T-Butyl $R_1$ and $R_9$ Taken Together with the Carbon Atom to which they are Attached are

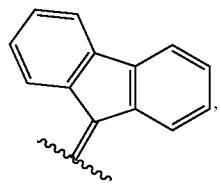

and G=

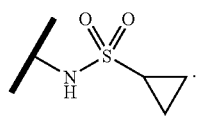

The title compound was prepared by using the same procedure as described in example 9. MS (ESI): m/z 753.15 (M+H).

Example 15

Compound of Formula VII, Wherein A=

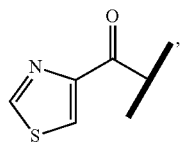

L=T-Butyl $R_1$ and $R_2$ Taken Together with the Carbon Atom to which they are Attached are

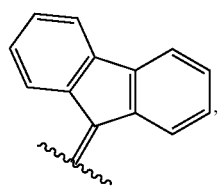 [SMILES: *=C1c2ccccc2-c2ccccc21]

and G=

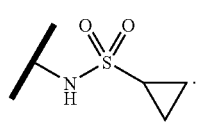

The title compound was prepared by using the same procedure as described in example 9. MS (ESI): m/z 769.13 (M+H).

Example 16

Compound of Formula VII, Wherein A=

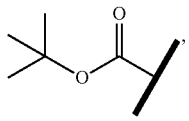

L=Iso-Propyl R$_1$ and R$_2$ Taken Together with the Carbon Atom to which they are Attached are

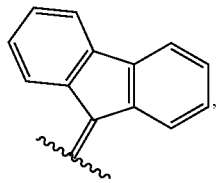 [SMILES: *=C1c2ccccc2-c2ccccc21]

and G=OH

The title compound was prepared by using the same procedure as described in example 1. MS (ESI): m/z 647.43 (M+Li).

Example 17

Compound of Formula VII, Wherein A=

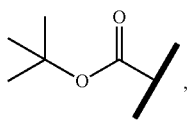

L=Iso-Propyl R$_1$ and R$_2$ Taken Together with the Carbon Atom to which they are Attached are

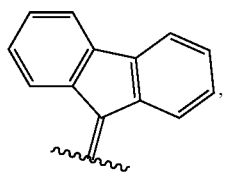 [SMILES: *=C1c2ccccc2-c2ccccc21]

and G=

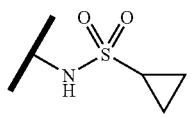

The title compound was prepared by using the same procedure as described in example 2. MS (ESI): m/z 744.17 (M+H).

Example 18

Compound of Formula VII, Wherein A=H
L=Iso-Propyl R$_1$ and R$_2$ Taken Together with the Carbon Atom to which they are Attached are

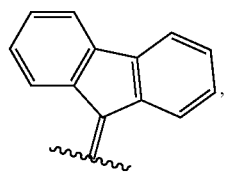 [SMILES: *=C1c2ccccc2-c2ccccc21]

and G=

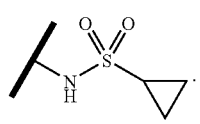

The title compound was prepared by using the same procedure as described in example 3. MS (ESI): m/z 644.32 (M+H).

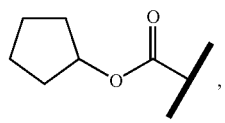

Example 19

Compound of Formula VII, Wherein A=L=Iso-Propyl R$_1$ and R$_2$ Taken Together with the Carbon Atom to which they are Attached are

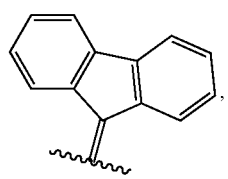 [SMILES: *=C1c2ccccc2-c2ccccc21]

and G=

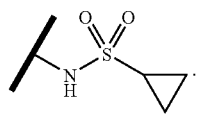

The title compound was prepared by using the same procedure as described in example 4. MS (ESI): m/z 756.15 (M+H).

Example 20

Compound of Formula VII, Wherein A=

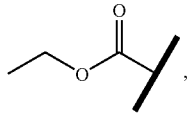

,

L=Iso-Propyl $R_1$ and $R_2$ Taken Together with the Carbon Atom to which they are Attached are

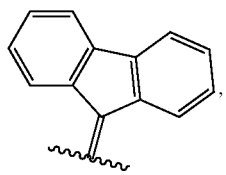 [SMILES: *=C1c2ccccc2-c2ccccc21]

, and G=

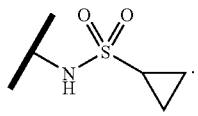

.

The title compound was prepared by using the same procedure as described in example 4. MS (ESI): m/z 716.15 (M+H).

Example 21

Compound of Formula VII, Wherein A=

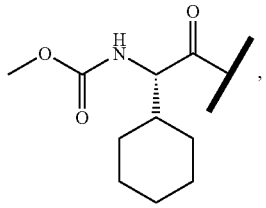

,

L=Iso-Propyl $R_1$ and $R_2$ Taken Together with the Carbon Atom to which they are Attached are

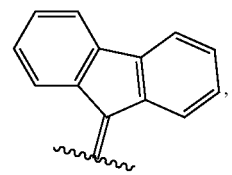

, and G=

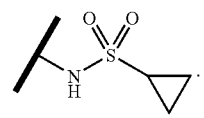

.

The title compound was prepared by using the same procedure as described in example 9. MS (ESI): m/z 841.59 (M+H).

Example 22

Compound of Formula VII, Wherein A=

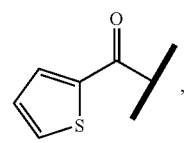

,

L=Iso-Propyl $R_1$ and $R_2$ Taken Together with the Carbon Atom to which they are Attached are

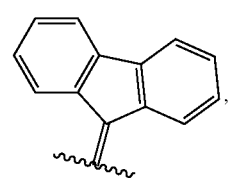

, and G=

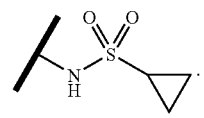

.

The title compound was prepared by using the same procedure as described in example 9. MS (ESI): m/z 754.06 (M+H).

Example 23 to 127, compounds of Formula VII in Table 1 are made following the procedures described in Example 1 to 22 and the Synthetic Methods section.

Example 128 to 227, compounds of Formula VIII in Table 2 are made following the procedures described in Example 1 to 22 and the Synthetic Methods section.

The compounds of the present invention exhibit potent inhibitory properties against the HCV NS3 protease. The following examples describe assays in which the compounds of the present invention can be tested for anti-HCV effects.

Example 228

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence is measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 µM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-NH$_2$, AnaSpec 22991, MW 1548.6) is used as the fluorogenic peptide substrate. The assay buffer contains 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, [−20° C.] and HCV Inh 2 (Anaspec 25346, MW 913.1) Ac-Asp-Glu-Dif-Cha-Cys-OH, are used as reference compounds.

IC$_{50}$ values are calculated using XLFit in ActivityBase (IDBS) using equation 205:

$$y=A+((B-A)/(1+((C/x)^D))).$$

Example 229

Cell-Based Replicon Assay

Quantification of HCV replicon RNA (HCV Cell Based Assay) is accomplished using the Huh 11-7 cell line (Lohmann, et al Science 285:110-113, 1999). Cells are seeded at 4×10$^3$ cells/well in 96 well plates and fed media containing DMEM (high glucose), 10% fetal calf serum, penicillin-streptomycin and non-essential amino acids. Cells are incubated in a 7.5% CO$_2$ incubator at 37° C. At the end of the incubation period, total RNA is extracted and purified from cells using Ambion RNAqueous 96 Kit (Catalog No. AM1812). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

```
HCV Forward primer "RBNS5bfor"
5'GCTGCGGCCTGTCGAGCT         (SEQ ID NO: 1):

HCV Reverse primer "RBNS5Brev"
5'CAAGGTCGTCTCCGCATAC.       (SEQ ID NO 2)
```

Detection of the RT-PCR product is accomplished using the Applied Biosystems (ABI) Prism 7500 Sequence Detection System (SDS) that detects the fluorescence that is emitted when the probe, which is labeled with a fluorescence reporter dye and a quencher dye, is degraded during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
                                     (SEQ ID NO: 3)
  5' FAM-CGAAGCTCCAGGACTGCACGATGCT-TAMRA
  FAM = Fluorescence reporter dye.
  TAMRA := Quencher dye.
```

The RT reaction is performed at 48° C. for 30 minutes followed by PCR. Thermal cycler parameters used for the PCR reaction on the ABI Prism 7500 Sequence Detection System are: one cycle at 95° C., 10 minutes followed by 40 cycles each of which include one incubation at 95° C. for 15 seconds and a second incubation for 60° C. for 1 minute.

To normalize the data to an internal control molecule within the cellular RNA, RT-PCR is performed on the cellular messenger RNA glyceraldehyde-3-phosphate dehydrogenase (GAPDH). The GAPDH copy number is very stable in the cell lines used. GAPDH RT-PCR is performed on the same RNA sample from which the HCV copy number is determined. The GAPDH primers and probes are contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines.

The effect of a specific anti-viral compound on HCV replicon RNA levels in Huh-1'-7 cells is determined by comparing the amount of HCV RNA normalized to GAPDH (e.g. the ratio of HCV/GAPDH) in the cells exposed to compound versus cells exposed to the DMSO vehicle (negative control). Specifically, cells are seeded at 4×10$^3$ cells/well in a 96 well plate and are incubated either with: 1) media containing 1% DMSO (0% inhibition control), or 2) media/1% DMSO containing a fixed concentration of compound. 96 well plates as described above are then incubated at 37° C. for 4 days (EC50 determination). Percent inhibition is defined as:

% Inhibition=100−100*S/C1 where

S=the ratio of HCV RNA copy number/GAPDH RNA copy number in the sample;

C1=the ratio of HCV RNA copy number/GAPDH RNA copy number in the 0% inhibition control (media/1% DMSO).

The dose-response curve of the inhibitor is generated by adding compound in serial, three-fold dilutions over three logs to wells starting with the highest concentration of a specific compound at 1.5 uM and ending with the lowest concentration of 0.23 nM. Further dilution series (500 nM to 0.08 nM for example) is performed if the EC50 value is not positioned well on the curve. EC50 is determined with the IDBS Activity Base program "XL Fit" using a 4-parameter, non-linear regression fit (model #205 in version 4.2.1, build 16).

What is claimed is:

1. A compound represented by the formula I:

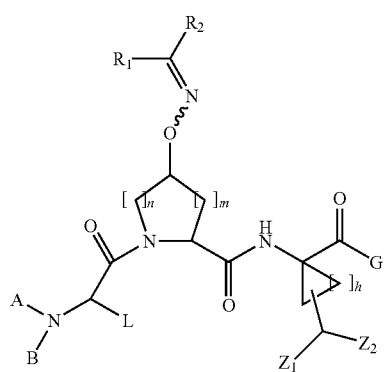

(I)

or a pharmaceutically acceptable salt thereof, wherein:

$R_1$ and $R_2$ are independently selected from the group consisting of:
  a) hydrogen;
  b) aryl;
  c) substituted aryl;
  d) heteroaryl;
  e) substituted heteroaryl;
  f) heterocyclic or substituted heterocyclic;
  g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  i) —$C_3$-$C_{12}$ cycloalkyl, or —$C_3$-$C_{12}$ cycloalkenyl;
  j) substituted —$C_3$-$C_{12}$ cycloalkyl, or substituted —$C_3$-$C_{12}$ cycloalkenyl;
  k) -Q-$R_3$, where Q is (CO), (CO)O, (CO)$NR_4$, (SO), ($SO_2$), ($SO_2$)$NR_4$; and $R_3$ and $R_4$ are independently selected from the group consisting of:
    (i) hydrogen;
    (ii) aryl;
    (iii) substituted aryl;
    (iv) heteroaryl;
    (v) substituted heteroaryl;
    (vi) heterocyclic;
    (vii) substituted heterocyclic;

(viii) —$C_1$-$C_8$ alkyl, —$C_2$-$C_8$ alkenyl, or —$C_2$-$C_8$ alkynyl each containing 0, 1, 2, or 3 heteroatoms selected from O, S or N;

(ix) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;

(x) —$C_3$-$C_{12}$ cycloalkyl, or —$C_3$-$C_{12}$ cycloalkenyl;

(xi) substituted —$C_3$-$C_{12}$ cycloalkyl, or substituted —$C_3$-$C_{12}$ cycloalkenyl;

or $R_1$ and $R_2$ taken together with the carbon atom to which they are attached form a cyclic moiety selected from: substituted or unsubstituted cycloalkyl, cycloalkenyl, or heterocyclic; or substituted or unsubstituted cycloalkyl, cycloalkenyl, or heterocyclic each fused with one or more group consisting of aryl, substituted aryl, heteroaryl, substituted heteroaryl, heterocyclic, substituted heterocyclic, cycloalkyl, substituted cycloalkyl, cycloakenyl, and substituted cycloalkenyl;

G is -E-$R_3$, where E is absent or E is O, CO, (CO)O, (CO)NH, $NR_5$, NH(CO), NH(CO)NH, NH($SO_2$)NH or $NHSO_2$;

A is selected from the group consisting of $R_5$, (CO)$R_5$, (CO)$OR_5$, (CO)$NHR_5$, $SO_2R_5$, ($SO_2$)$OR_5$ and $SO_2NHR_5$;

$R_5$ is selected from the group consisting of:
a) hydrogen;
b) aryl;
c) substituted aryl;
d) heteroaryl;
e) substituted heteroaryl;
f) heterocyclic;
g) substituted heterocyclic;
h) —$C_1$-$C_8$ alkyl, —$C_2$-$C_8$ alkenyl, or —$C_2$-$C_8$ alkynyl each containing 0, 1, 2, or 3 heteroatoms selected from O, S or N;
i) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
j) —$C_3$-$C_{12}$ cycloalkyl, or —$C_3$-$C_{12}$ cycloalkenyl;
k) substituted —$C_3$-$C_{12}$ cycloalkyl, or substituted —$C_3$-$C_{12}$ cycloalkenyl;

B is H or $CH_3$;

L is selected from the group consisting of:
(1) hydrogen;
(2) aryl;
(3) substituted aryl;
(4) heteroaryl;
(5) substituted heteroaryl;
(6) heterocyclic;
(7) substituted heterocyclic;
(8) —$C_1$-$C_8$ alkyl, —$C_2$-$C_8$ alkenyl, or —$C_2$-$C_8$ alkynyl each containing 0, 1, 2, or 3 heteroatoms selected from O, S or N;
(9) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(10) —$C_3$-$C_{12}$ cycloalkyl, or —$C_3$-$C_{12}$ cycloalkenyl;
(11) substituted —$C_3$-$C_{12}$ cycloalkyl, or substituted —$C_3$-$C_{12}$ cycloalkenyl;

$Z_1$ and $Z_2$ are independently selected from halogen;
m=0, 1, 2 or 3;
n=1, 2 or 3 and
h=1, 2, or 3.

2. A compound according to claim 1 represented by formula II:

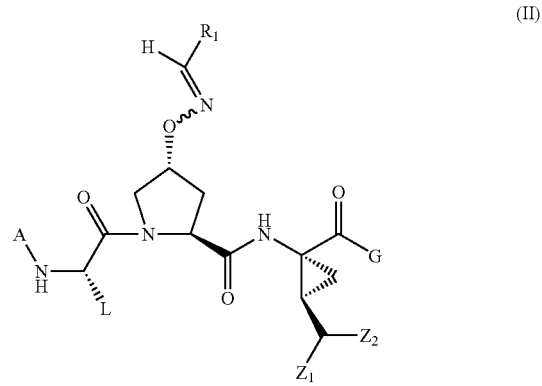

(II)

where A, G, L, $R_1$, $Z_1$ and $Z_2$ are as previously defined in claim 1.

3. A compound according to claim 2, wherein $R_1$ is selected from the group consisting of aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl G is —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; and $Z_1$ and $Z_2$ are independently selected from F, Cl, and Br.

4. A compound according to claim 1 represented by formula III:

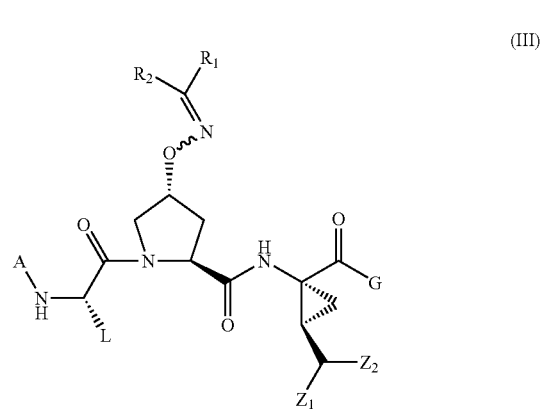

(III)

where A, G, L, $R_1$, $R_2$, $Z_1$ and $Z_2$ are as previously defined in claim 1.

5. A compound according to claim 4, wherein $R_1$ and $R_2$ are independently selected from the group consisting of aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; or $R_1$ and $R_2$ taken together with the carbon atom to which they are attached form a cyclic moiety selected from aryl, heteroaryl, heterocyclic, substituted aryl, substituted heteroaryl, and substituted heterocyclic; A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; G is —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; and $Z_1$ and $Z_2$ are independently selected from F, Cl, and Br.

6. A compound represented by formula IV:

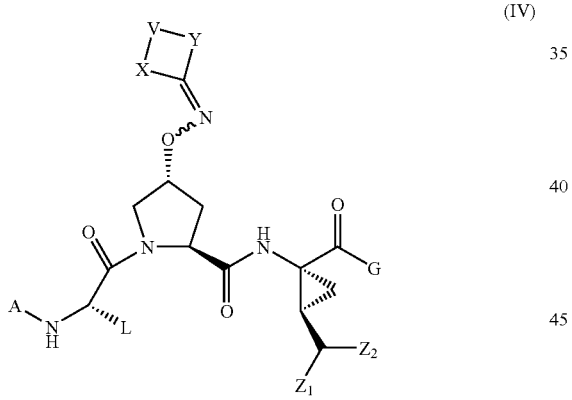

(IV)

wherein V is absent, or V is CO, O, S, SO, $SO_2$, NH, $NCH_3$, or $(CH_2)_q$; q is 1, 2, 3 or 4; and X and Y are independently selected from the group consisting of: aryl; substituted aryl; heteroaryl; substituted heteroaryl; heterocyclic; and substituted heterocyclic;

G is -E-$R_3$ where E is absent or E is O, CO, (CO)O, (CO)NH, $NR_5$, NH(CO), NH(CO)NH, NH($SO_2$)NH or $NHSO_2$;

A is selected from the group consisting of $R_5$, (CO)$R_5$, (CO)O$R_5$, (CO)NH$R_5$, ($SO_2$)O$R_5$ and $SO_2$NH$R_5$;

$R_5$ is selected from the group consisting of:
  a) hydrogen;
  b) aryl;
  c) substituted aryl;
  d) heteroaryl;
  e) substituted heteroaryl;
  f) heterocyclic;
  g) substituted heterocyclic;
  h) $C_1$-$C_8$ alkyl, —$C_2$-$C_8$ alkenyl, or —$C_2$-$C_8$ alkenyl each containing 0, 1, 2, or 3 heteroatoms selected from O, S or N;
  i) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  j) —$C_3$-$C_{12}$ cycloalkyl, or —$C_3$-$C_{12}$ cycloalkenyl;
  k) substituted —$C_3$-$C_{12}$ cycloalkyl, or substituted —$C_3$-$C_{12}$ cycloalkenyl;

L is selected from the group consisting of:
  (1) hydrogen;
  (2) aryl;
  (3) substituted aryl;
  (4) heteroaryl;
  (5) substituted heteroaryl;
  (6) heterocyclic;
  (7) substituted heterocyclic;
  (8) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  (9) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  (10) —$C_3$-$C_{12}$ cycloalkyl, or —$C_3$-$C_{12}$ cycloalkenyl;
  (11) substituted —$C_3$-$C_{12}$ cycloalkyl, or substituted —$C_3$-$C_{12}$ cycloalkenyl; and $Z_1$ and $Z_2$ are independently selected from halogen.

7. A compound represented by one of the formulas below:

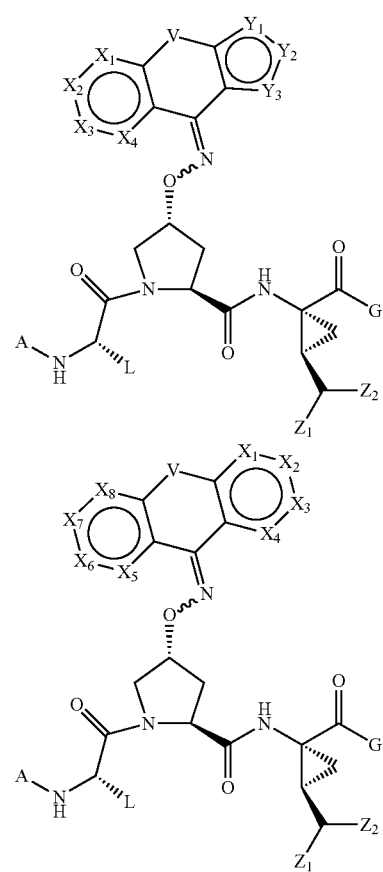

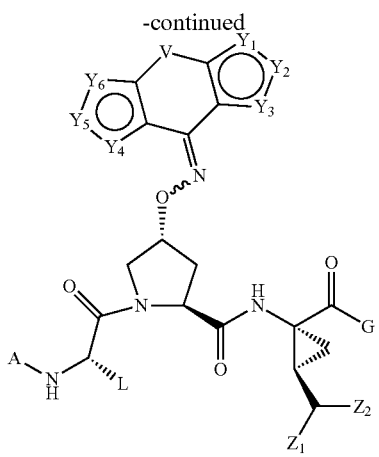

wherein $X_1$-$X_8$ are independently selected from CH and N and can each be further substituted when it is a CH, and $Y_1$-$Y_3$ are independently selected from CH, N, NH, S and O and can each be further substituted when it is CH or NH; V is absent, CO, O, S, NH, or $(CH_2)_q$, where q is 1, 2 or 3; A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; G is —O—$R_3$, —NH—C(O)—$R_3$, —NH—$SO_2$—NH—$R_3$ or —$NHSO_2$—$R_3$, where $R_3$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; and $Z_1$ and $Z_2$ are independently selected from F, Cl, and Br.

8. A compound according to claim 7 represented by the formula

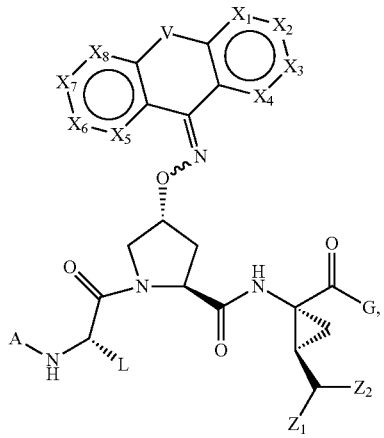

wherein $X_1$-$X_8$ are independently selected from CH and N and can each be further substituted when it is a CH; V is absent, CO, O, S, NH, or $(CH_2)_q$, where q is 1, 2 or 3; A is —C(O)—O—$R_5$, where $R_5$ is —$C_3$-$C_{12}$ cycloalkyl or substituted —$C_3$-$C_{12}$ cycloalkyl; L is selected from —$C_1$-$C_8$ alkyl and substituted —$C_1$-$C_8$ alkyl; $Z_1$ and $Z_2$ are independently selected from F, Cl, and Br; and G is —$NHSO_2$—$R_3$, where $R_3$ is selected from —$C_3$-$C_{12}$ cycloalkyl and substituted —$C_3$-$C_{12}$ cycloalkyl.

9. A compound according to claim 8 represented by the formula

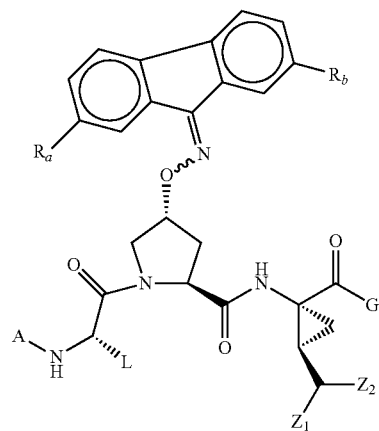

wherein Ra and Rb are independently selected from hydrogen and halogen; A is —C(O)—O—$R_5$, where $R_5$ is —$C_3$-$C_{12}$ cycloalkyl or substituted —$C_3$-$C_{12}$ cycloalkyl; L is selected from —$C_1$-$C_8$ alkyl and substituted —$C_1$-$C_8$ alkyl; $Z_1$ and $Z_2$ are independently selected from F, Cl, and Br; and G is —$NHSO_2$—$R_3$, where $R_3$ is —$C_3$-$C_{12}$ cycloalkyl or substituted —$C_3$-$C_{12}$ cycloalkyl.

10. A compound of claim 1 represented by formula V:

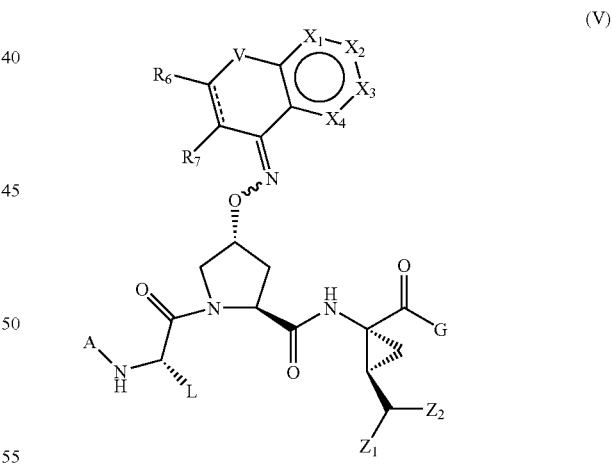

(V)

where $X_1$-$X_4$ are independently selected from CO, CH, NH, O and N; $X_1$-$X_4$ can be further substituted when CH or NH; $R_6$ and $R_7$ are independently $R_3$ or $R_6$ and $R_7$ taken together with the carbon atoms to which they are attached form a cyclic moiety selected from $C_3$-$C_{12}$ cycloalkyl, substituted $C_3$-$C_{12}$ cycloalkyl, $C_3$-$C_{12}$ cycloalkenyl, substituted $C_3$-$C_{12}$ cycloalkenyl, aryl, heteroaryl, heterocyclic, substituted aryl, substituted heteroaryl and substituted heterocyclic; V is absent, or V is CO, O, S, SO, $SO_2$, NH or $NCH_3$, or $(CH_2)_q$; where q is 1, 2, 3 or 4; and $R_3$, A, G, L, $Z_1$ and $Z_2$ are as previously defined in claim 1.

11. A compound according to claim 10, wherein $R_6$ and $R_7$ taken together with the carbon atoms to which they are attached form a cyclic moiety selected from $C_3$-$C_{12}$ cycloalkyl, substituted $C_3$-$C_{12}$ cycloalkyl, $C_3$-$C_{12}$ cycloalkenyl, substituted $C_3$-$C_{12}$ cycloalkenyl, aryl, heteroaryl, heterocyclic, substituted aryl, substituted heteroaryl and substituted heterocyclic; A is selected from the group consisting of —C(O)—$R_5$, —C(O)—O—$R_5$ and —C(O)—NH—$R_5$, where $R_5$ is selected from aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; G is —O—$R_3$, —NH—C(O)—$R_3$, —NH—$SO_2$—NH—$R_3$ or —$NHSO_2$—$R_3$, where $R_3$ is hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl; and $Z_1$ and $Z_2$ are independently selected from F, Cl, and Br.

12. A compound of claim 1 represented by formula VI:

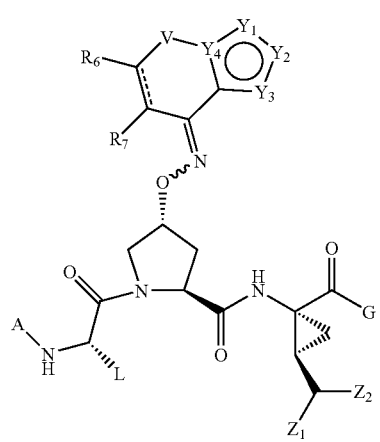

(VI)

where $Y_1$-$Y_3$ are independently selected from CO, CH, NH, N, S and O; and can each be further substituted when it is CH or NH; $Y_4$ is selected from C, CH and N; V is absent, or V is CO, O, S, SO, $SO_2$, NH or $NCH_3$, or $(CH_2)_q$; where q is 1, 2, 3 or 4; $R_6$ and $R_7$ are independently $R_3$, or $R_6$ and $R_7$ taken together with the carbon atoms to which they are attached form a cyclic moiety selected from $C_3$-$C_{12}$ cycloalkyl, substituted $C_3$-$C_{12}$ cycloalkyl, $C_3$-$C_{12}$ cycloalkenyl, substituted $C_3$-$C_{12}$ cycloalkenyl, aryl, heteroaryl, heterocyclic, substituted aryl, substituted heteroaryl and substituted heterocyclic; and $R_3$, A, G, L, $Z_1$ and $Z_2$ are defined as in claim 1.

13. A compound according to claim 12, wherein $R_6$ and $R_7$ taken together with the carbon atoms to which they are attached form a cyclic moiety selected from $C_3$-$C_{12}$ cycloalkyl, substituted $C_3$-$C_{12}$ cycloalkyl, $C_3$-$C_{12}$ cycloalkenyl, substituted $C_3$-$C_{12}$ cycloalkenyl, aryl, heteroaryl, heterocyclic, substituted aryl, substituted heteroaryl and substituted heterocyclic; A is selected from the group consisting of —C(O)—$R_5$, —C(O)—O—$R_5$ and —C(O)—NH—$R_5$, where $R_5$ is aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl; L is selected from $C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl; G is —O—$R_3'$, —NH—C(O)—$R_3'$, —NH—$SO_2$—NH—$R_3'$ or —$NHSO_2$—$R_3'$, where $R_3'$ is selected from hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl and $Z_1$ and $Z_2$ are independently selected from F, Cl, and Br.

14. A compound of claim 1 having the Formula VII selected from compounds 1)-127) of Table 1:

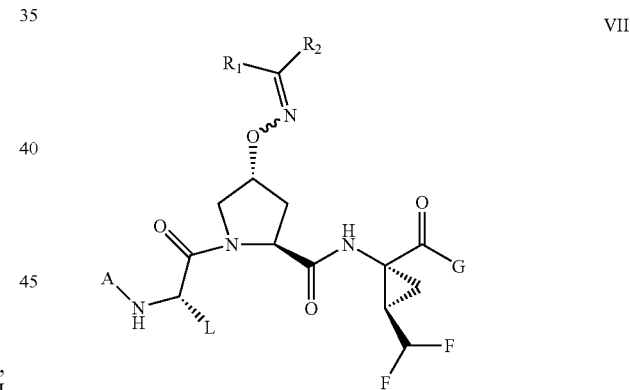

VII where $R_1$ and $R_2$ are taken together with the carbon to which they are attached to form $R_1R_2$; and A, L, $R_1R_2$ and G are delineated for each example in TABLE 1:

TABLE 1

| Example | A | L | $R_1R_2$ | G |
|---|---|---|---|---|
| 1) | | | | —OH |

TABLE 1-continued

| Example | A | L | R₁R₂ | G |
|---|---|---|---|---|
| 2) | tert-butyl ester group | tert-butyl | fluorenylidene | cyclopropanesulfonamide |
| 3) | —H | tert-butyl | fluorenylidene | cyclopropanesulfonamide |
| 4) | cyclopentyl ester group | tert-butyl | fluorenylidene | cyclopropanesulfonamide |
| 5) | cyclobutyl ester group | tert-butyl | fluorenylidene | cyclopropanesulfonamide |
| 6) | isopropyl ester group | tert-butyl | fluorenylidene | cyclopropanesulfonamide |
| 7) | ethyl ester group | tert-butyl | fluorenylidene | cyclopropanesulfonamide |
| 8) | methyl ester group | tert-butyl | fluorenylidene | cyclopropanesulfonamide |
| 9) | methoxycarbonylamino-cyclohexyl acyl group | tert-butyl | fluorenylidene | cyclopropanesulfonamide |

US 8,361,958 B2
TABLE 1-continued
| Example | A | L | R₁R₂ | G |
|---|---|---|---|---|
| 10) | 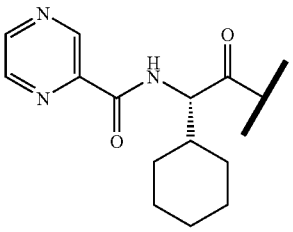 |  | 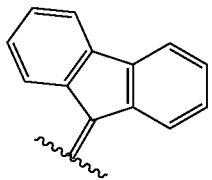 [SMILES: *=C1c2ccccc2-c2ccccc21] | 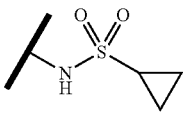 |
| 11) | 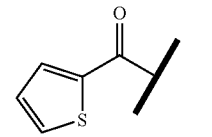 |  | 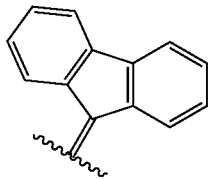 [SMILES: *=C1c2ccccc2-c2ccccc21] | 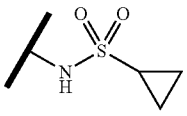 |
| 12) | 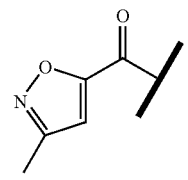 |  | 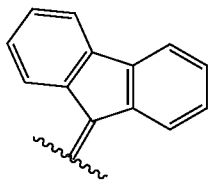 [SMILES: *=C1c2ccccc2-c2ccccc21] | 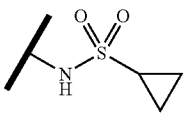 |
| 13) | 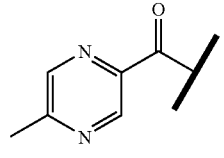 |  | 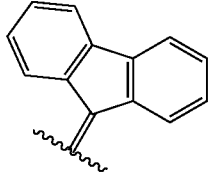 [SMILES: *=C1c2ccccc2-c2ccccc21] | 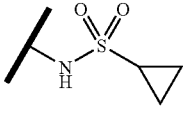 |
| 14) | 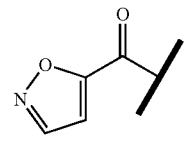 |  | 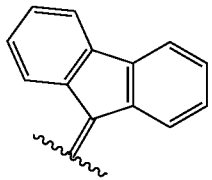 [SMILES: *=C1c2ccccc2-c2ccccc21] | 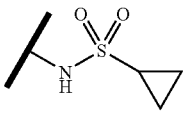 |
| 15) | 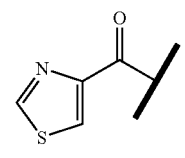 |  | 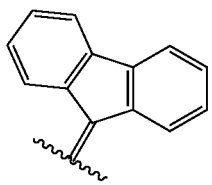 [SMILES: *=C1c2ccccc2-c2ccccc21] | 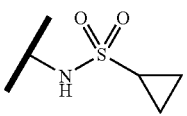 |
| 16) | 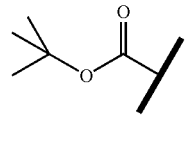 |  | 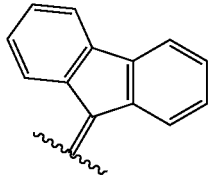 [SMILES: *=C1c2ccccc2-c2ccccc21] | —OH |
| 17) | 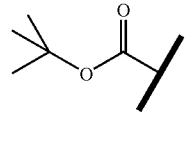 |  | 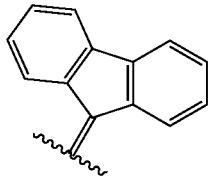 [SMILES: *=C1c2ccccc2-c2ccccc21] | 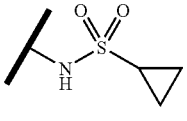 |

TABLE 1-continued

| Example | A | L | R₁R₂ | G |
|---|---|---|---|---|
| 18) | —H | isopropyl | fluorenyl | cyclopropylsulfonamide |
| 19) | cyclopentyl ester | isopropyl | fluorenyl | cyclopropylsulfonamide |
| 20) | ethyl ester | isopropyl | fluorenyl | cyclopropylsulfonamide |
| 21) | methyl carbamate with cyclohexyl | isopropyl | fluorenyl | cyclopropylsulfonamide |
| 22) | thiophene-2-carbonyl | isopropyl | fluorenyl | cyclopropylsulfonamide |
| 23) | tert-butyl amide | tert-butyl | fluorenyl | cyclopropylsulfonamide |
| 24) | cyclopentyl amide | tert-butyl | fluorenyl | cyclopropylsulfonamide |
| 25) | tert-butyl amide | isopropyl | fluorenyl | cyclopropylsulfonamide |

TABLE 1-continued

| Example | A | L | R₁R₂ | G |
|---------|---|---|------|---|
| 26) | | | | |
| 27) | | | | —OH |
| 28) | | | | —OH |
| 29) | | | | |
| 30) | | | | —OH |
| 31) | | | | |
| 32) | | | | —OH |
| 33) | | | | |

TABLE 1-continued
| Example | A | L | R₁R₂ | G |
|---|---|---|---|---|
| 34) | 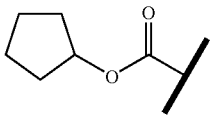 |  | 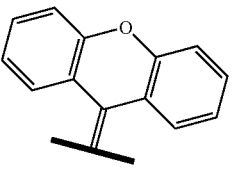 | 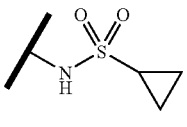 |
| 35) | 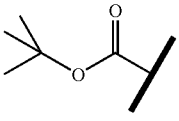 |  | 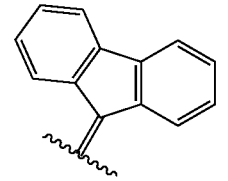 | —OH |
| 36) | 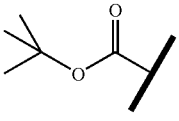 | 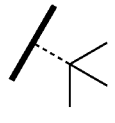 | 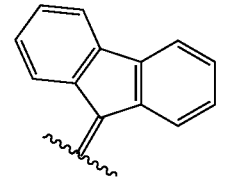 [SMILES: *=C1c2ccccc2-c2ccccc21] | 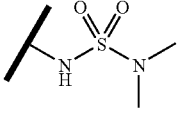 |
| 37) | 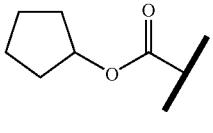 |  | 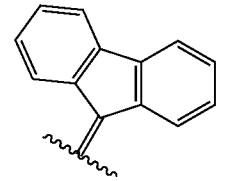 | 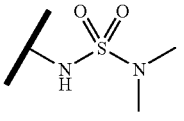 |
| 38) | 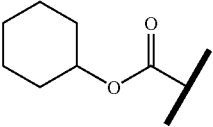 |  | 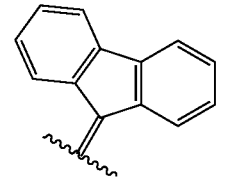 [SMILES: *=C1c2ccccc2-c2ccccc21] | 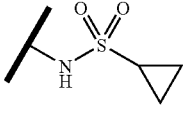 |
| 39) | 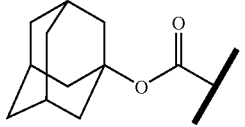 |  | 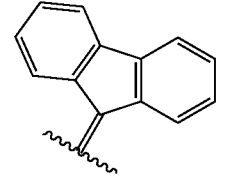 | 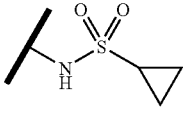 |
| 40) | 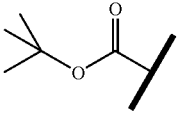 |  | 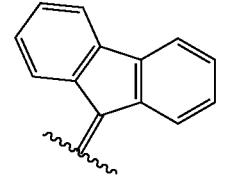 | 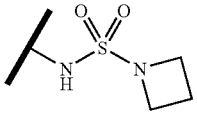 |
| 41) | 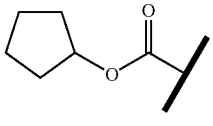 |  | 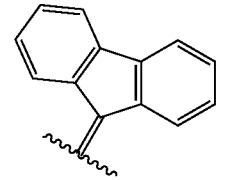 [SMILES: *=C1c2ccccc2-c2ccccc21] | 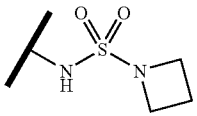 |

TABLE 1-continued

| Example | A | L | R₁R₂ | G |
|---|---|---|---|---|
| 42) | tert-butyl ester | tert-butyl | fluorenylidene | pyrrolidine sulfonamide |
| 43) | cyclopentyl ester | tert-butyl | fluorenylidene | pyrrolidine sulfonamide |
| 44) | cyclopentyl ester | sec-butyl | fluorenylidene | cyclopropyl sulfonamide |
| 45) | cyclopentyl ester | cyclohexyl | fluorenylidene | cyclopropyl sulfonamide |
| 46) | cyclopentyl ester | cyclohexylmethyl | fluorenylidene | cyclopropyl sulfonamide |
| 47) | tert-butyl ester | tert-butyl | 2-thienyl-methoxyphenyl-propenyl | cyclopropyl sulfonamide |
| 48) | tert-butyl ester | tert-butyl | fluoro-chromanylidene | cyclopropyl sulfonamide |
| 49) | cyclobutyl ester | tert-butyl | 2-thienyl-methoxyphenyl-propenyl | cyclopropyl sulfonamide |

TABLE 1-continued
| Example | A | L | R₁R₂ | G |
|---|---|---|---|---|
| 50) | 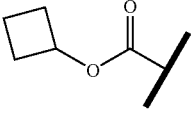 |  | 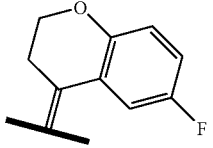 | 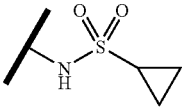 |
| 51) | 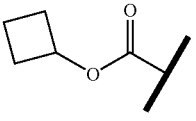 |  | 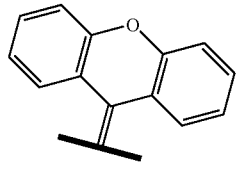 | 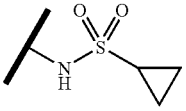 |
| 52) | 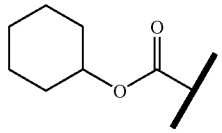 |  | 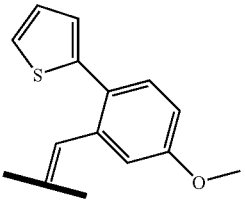 | 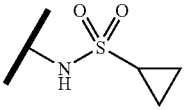 |
| 53) | 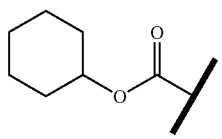 |  | 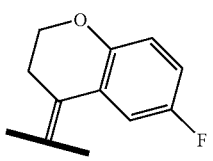 | 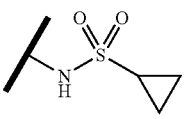 |
| 54) | 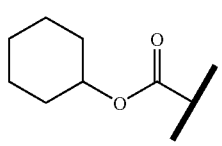 |  | 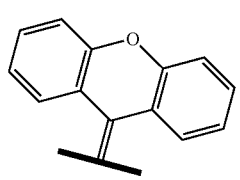 | 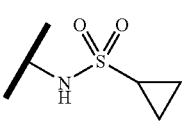 |
| 55) | 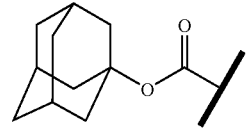 |  | 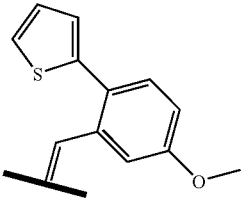 | 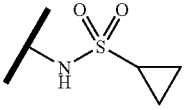 |
| 56) | 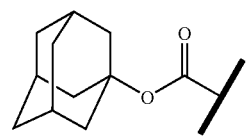 |  | 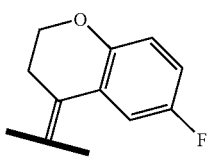 | 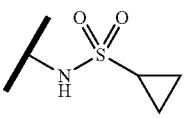 |
| 57) | 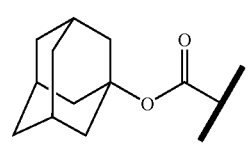 |  | 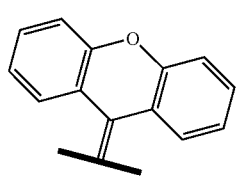 | 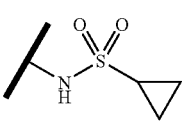 |
| 58) | 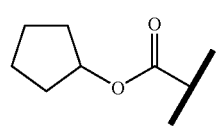 |  | 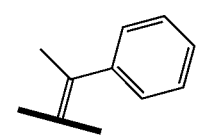 | —OH |

TABLE 1-continued

| Example | A | L | R₁R₂ | G |
|---|---|---|---|---|
| 59) | cyclopentyl ester | t-Bu | diphenyl vinyl | —OH |
| 60) | cyclopentyl ester | t-Bu | isopropyl phenyl vinyl | —OH |
| 61) | cyclopentyl ester | t-Bu | cyclopentyl phenyl vinyl | —OH |
| 62) | cyclopentyl ester | t-Bu | styryl | —OH |
| 63) | cyclopentyl ester | t-Bu | 2-biphenyl vinyl | —OH |
| 64) | cyclopentyl ester | t-Bu | 3-biphenyl vinyl | —OH |
| 65) | cyclopentyl ester | t-Bu | 4-biphenyl vinyl | —OH |
| 66) | cyclopentyl ester | t-Bu | 1-naphthyl vinyl | —OH |
| 67) | cyclopentyl ester | t-Bu | 2-naphthyl vinyl | —OH |

TABLE 1-continued

| Example | A | L | R₁R₂ | G |
|---|---|---|---|---|
| 68) | cyclopentyl ester | tBu | 2-ethylidene-biphenyl | —OH |
| 69) | cyclopentyl ester | tBu | quinolin-4-yl vinyl | —OH |
| 70) | cyclopentyl ester | tBu | quinolin-3-yl vinyl | —OH |
| 71) | cyclopentyl ester | tBu | 2-(thiophen-2-yl)phenyl vinyl | —OH |
| 72) | cyclopentyl ester | tBu | 2-(pyrazol-1-yl)phenyl vinyl | —OH |
| 73) | cyclopentyl ester | tBu | 2-(1,2,4-triazol-1-yl)phenyl vinyl | —OH |
| 74) | cyclopentyl ester | tBu | 2-(thiazol-2-yl)phenyl vinyl | —OH |

TABLE 1-continued

| Example | A | L | R₁R₂ | G |
|---------|---|---|------|---|
| 75) | | | | —OH |
| 76) | | | | —OH |
| 77) | | | | —OH |
| 78) | | | | —OH |
| 79) | | | | —OH |
| 80) | | | | —OH |
| 81) | | | | —OH |
| 82) | | | | —OH |

TABLE 1-continued

| Example | A | L | R₁R₂ | G |
|---|---|---|---|---|
| 83) | cyclopentyl-O-C(=O)- | -C(CH₃)₂- | 7-methoxy-tetrahydronaphthalen-1-ylidene | —OH |
| 84) | cyclopentyl-O-C(=O)- | -C(CH₃)₂- | 6-methoxy-tetrahydronaphthalen-1-ylidene | —OH |
| 85) | cyclopentyl-O-C(=O)- | -C(CH₃)₂- | 6,7-dimethoxy-tetrahydronaphthalen-1-ylidene | —OH |
| 86) | cyclopentyl-O-C(=O)- | -C(CH₃)₂- | 5,6,7,8-tetrahydroquinolin-8-ylidene | —OH |
| 87) | cyclopentyl-O-C(=O)- | -C(CH₃)₂- | thiochroman-4-ylidene | —OH |
| 88) | cyclopentyl-O-C(=O)- | -C(CH₃)₂- | chroman-4-ylidene | —OH |
| 89) | cyclopentyl-O-C(=O)- | -C(CH₃)₂- | 6-methoxy-chroman-4-ylidene | —OH |
| 90) | cyclopentyl-O-C(=O)- | -C(CH₃)₂- | 7-(thiophen-2-yl)-tetrahydronaphthalen-1-ylidene | —OH |
| 91) | cyclopentyl-O-C(=O)- | -C(CH₃)₂- | 2-phenyl-4H-chromen-4-ylidene | —OH |

TABLE 1-continued

| Example | A | L | R₁R₂ | G |
|---|---|---|---|---|
| 92) | cyclopentyl ester | t-butyl | 3-phenyl-4H-chromen-4-ylidene | —OH |
| 93) | cyclopentyl ester | t-butyl | 1-phenylethylidene | cyclopropanesulfonamide |
| 94) | cyclopentyl ester | t-butyl | diphenylmethylene | cyclopropanesulfonamide |
| 95) | cyclopentyl ester | t-butyl | 2-methyl-1-phenylpropylidene | cyclopropanesulfonamide |
| 96) | cyclopentyl ester | t-butyl | cyclopentyl(phenyl)methylene | cyclopropanesulfonamide |
| 97) | cyclopentyl ester | t-butyl | phenylmethylene | cyclopropanesulfonamide |
| 98) | cyclopentyl ester | t-butyl | (2-phenylphenyl)methylene | cyclopropanesulfonamide |
| 99) | cyclopentyl ester | t-butyl | (3-biphenyl)methylene | cyclopropanesulfonamide |
| 100) | cyclopentyl ester | t-butyl | (4-biphenyl)methylene | cyclopropanesulfonamide |

TABLE 1-continued
| Example | A | L | R₁R₂ | G |
|---|---|---|---|---|
| 101) | 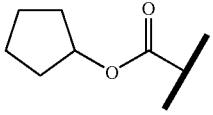 | 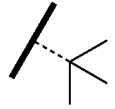 | 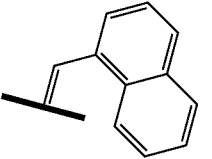 | 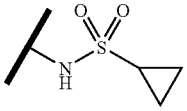 |
| 102) | 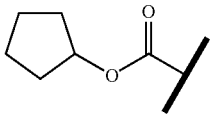 | 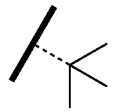 | 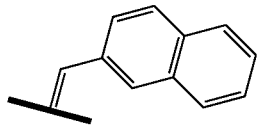 | 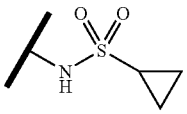 |
| 103) | 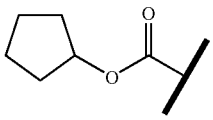 |  | 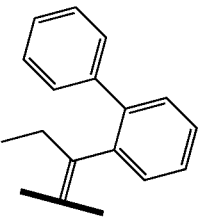 | 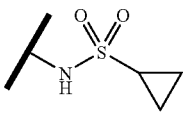 |
| 104) | 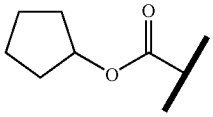 | 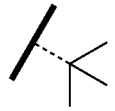 | 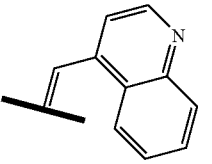 | 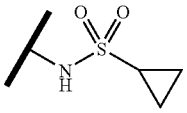 |
| 105) | 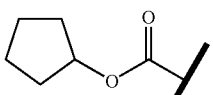 | 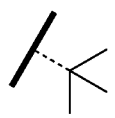 | 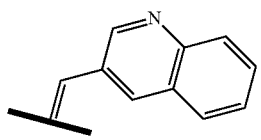 | 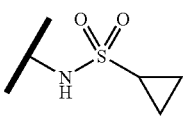 |
| 106) | 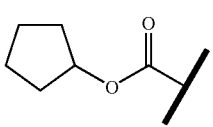 |  | 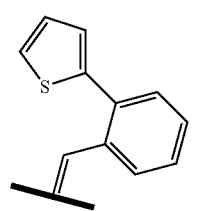 | 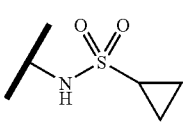 |
| 107) | 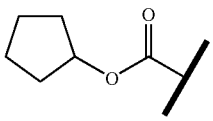 |  | 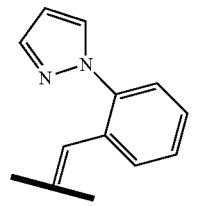 | 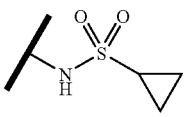 |
| 108) | 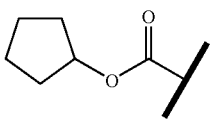 |  | 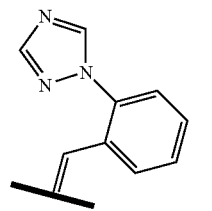 | 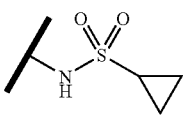 |

TABLE 1-continued
| Example | A | L | R₁R₂ | G |
|---|---|---|---|---|
| 109) | 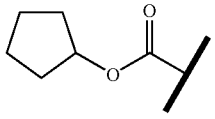 |  | 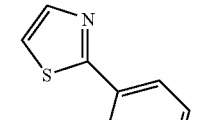 | 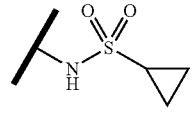 |
| 110) | 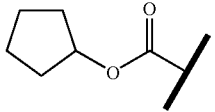 | 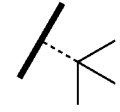 | 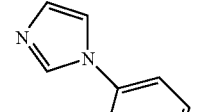 | 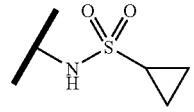 |
| 111) | 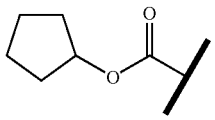 | 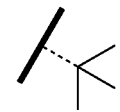 | 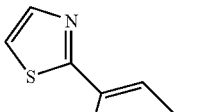 | 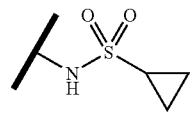 |
| 112) | 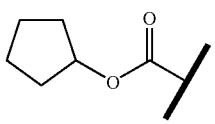 | 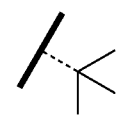 | 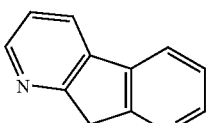 | 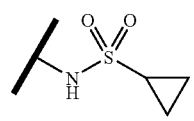 |
| 113) | 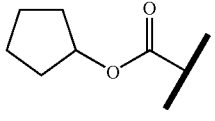 | 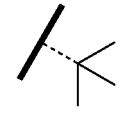 | 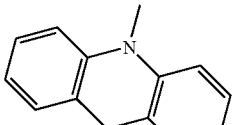 | 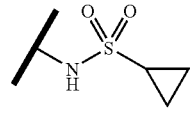 |
| 114) | 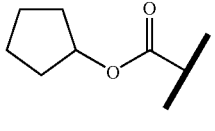 |  | 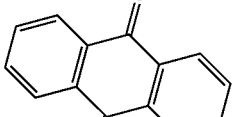 | 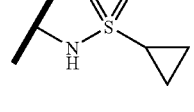 |
| 115) | 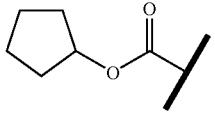 |  | 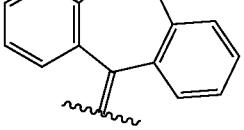 | 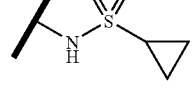 |
| 116) | 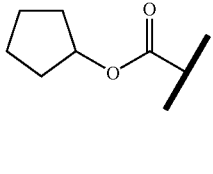 |  | 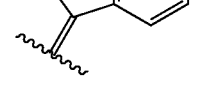 | 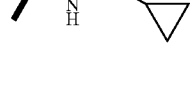 |

TABLE 1-continued
| Example | A | L | R₁R₂ | G |
|---|---|---|---|---|
| 117) | 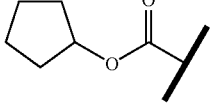 |  | 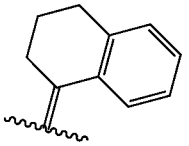 | 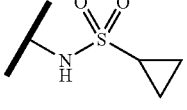 |
| 118) | 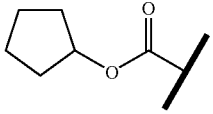 |  | 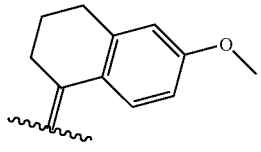 [SMILES: *=C1CCCc2cc(OC)ccc21] | 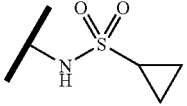 |
| 119) | 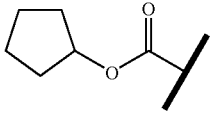 |  | 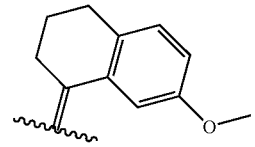 [SMILES: *=C1CCCc2ccc(OC)cc21] | 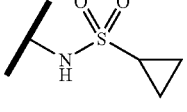 |
| 120) | 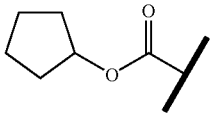 |  | 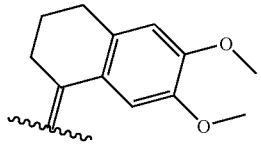 [SMILES: *=C1CCCc2cc(OC)c(OC)cc21] | 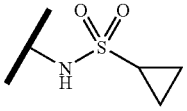 |
| 121) | 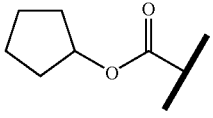 |  | 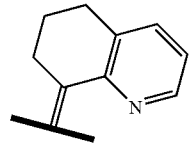 | 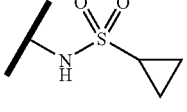 |
| 122) | 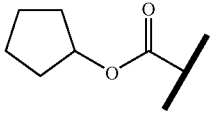 |  | 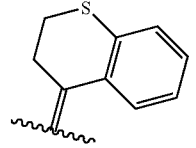 | 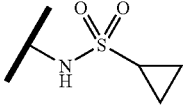 |
| 123) | 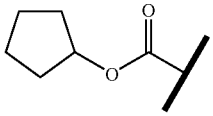 |  | 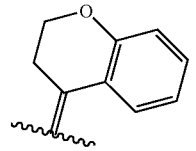 | 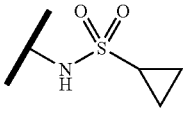 |
| 124) | 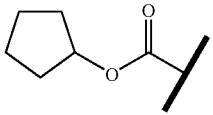 |  | 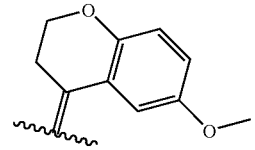 [SMILES: *=C1CCOc2ccc(OC)cc21] | 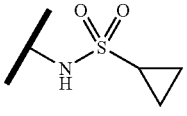 |
| 125) | 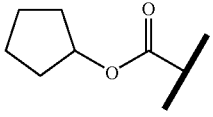 |  | 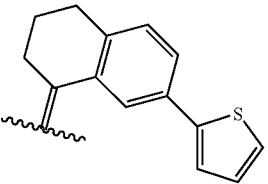 [SMILES: *=C1CCCc2ccc(-c3cccs3)cc21] | 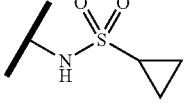 |

TABLE 1-continued
| Example | A | L | R₁R₂ | G |
|---|---|---|---|---|
| 126) | | | | |
| 127) | | | | |
15. A compound having the Formula VIII selected from compounds 128)-227) of Table 2:
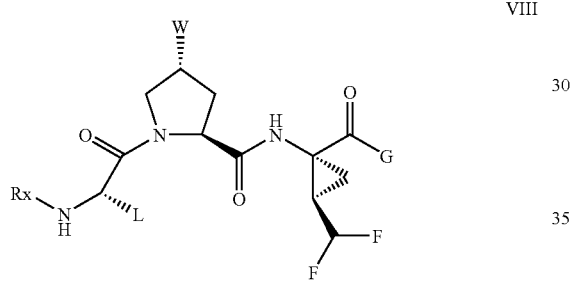
VIII
wherein Rx, L, W and G are delineated for each example in TABLE 2:
TABLE 2
| Example | Rx | L | W | G |
|---|---|---|---|---|
| 128) | | | | |
| 129) | | | | |

TABLE 2-continued

| Example | Rx | L | W | G |
|---|---|---|---|---|
| 130) | cyclopentyl ester | cyclohexyl | fluorenone oxime | cyclopropanesulfonamide |
| 131) | tert-butyl ester | cyclohexylmethyl | fluorenone oxime | cyclopropanesulfonamide |
| 132) | cyclopentyl ester | cyclohexylmethyl | fluorenone oxime | cyclopropanesulfonamide |
| 133) | tert-butyl ester | tert-butyl | fluorenone oxime | pyrrolidine sulfonamide |
| 134) | cyclopentyl ester | tert-butyl | fluorenone oxime | pyrrolidine sulfonamide |
| 135) | tert-butyl ester | tert-butyl | fluorenone oxime | thiophene-2-sulfonamide |
| 136) | cyclopentyl ester | tert-butyl | fluorenone oxime | thiophene-2-sulfonamide |

TABLE 2-continued

| Example | Rx | L | W | G |
|---|---|---|---|---|
| 137) | ethyl ester -CH(CH₃)- | tert-butyl | fluoren-9-ylidene-aminooxy | -NH-SO₂-(2-thienyl) |
| 138) | (S)-tetrahydrofuran-3-yl ester -CH(CH₃)- | tert-butyl | fluoren-9-ylidene-aminooxy | -NH-SO₂-cyclopropyl |
| 139) | (R)-tetrahydrofuran-3-yl ester -CH(CH₃)- | tert-butyl | fluoren-9-ylidene-aminooxy | -NH-SO₂-cyclopropyl |
| 140) | pyrrolidin-1-yl carbonyl -CH(CH₃)- | tert-butyl | fluoren-9-ylidene-aminooxy | -NH-SO₂-cyclopropyl |
| 141) | morpholin-4-yl carbonyl -CH(CH₃)- | tert-butyl | fluoren-9-ylidene-aminooxy | -NH-SO₂-cyclopropyl |
| 142) | tert-butyl ester -CH(CH₃)- | tert-butyl | fluoren-9-ylidene-aminooxy | -NH-SO₂-(azetidin-1-yl) |
| 143) | 2-(imidazol-1-yl)ethyl ester -CH(CH₃)- | tert-butyl | fluoren-9-ylidene-aminooxy | -NH-SO₂-cyclopropyl |

US 8,361,958 B2
175                                                                                          176
TABLE 2-continued
| Example | Rx | L | W | G |
|---|---|---|---|---|
| 144) | 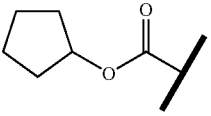 |  | —O—NH$_2$ | 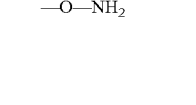 |
| 145) | 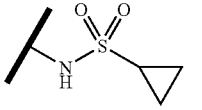 | 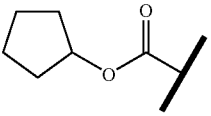 |  | 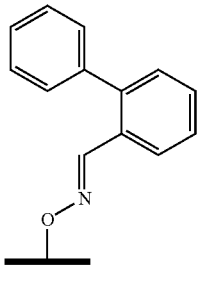 |
| 146) | 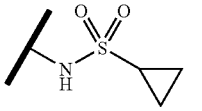 | 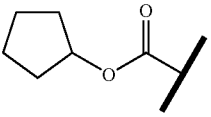 |  | 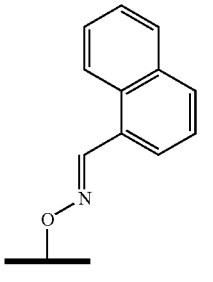 |
| 147) | 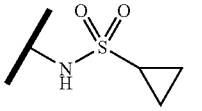 | 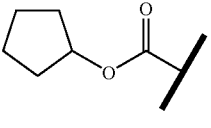 |  | 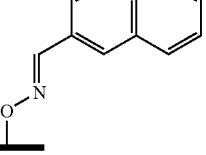 |
| 148) | 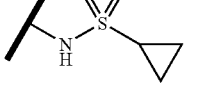 | 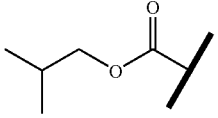 |  | 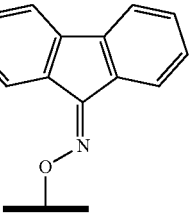 |
| 149) | 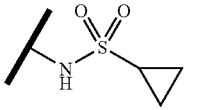 | 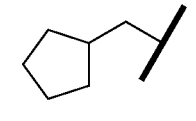 |  | 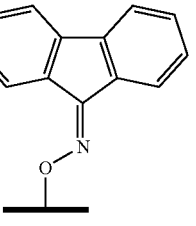 |
| 150) | 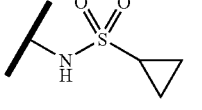 | 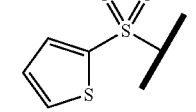 |  | 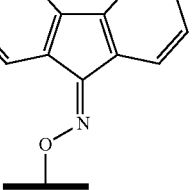 |

TABLE 2-continued
| Example | Rx | L | W | G |
|---|---|---|---|---|
| 151) | 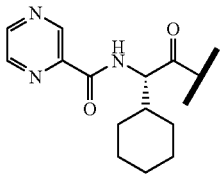 | 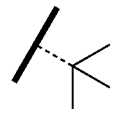 | 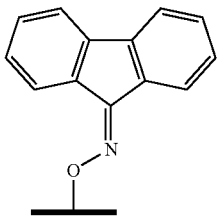 | 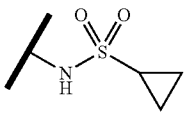 |
| 152) | 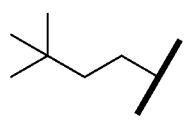 |  | 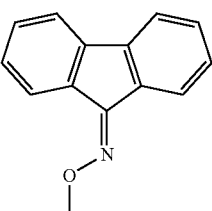 | 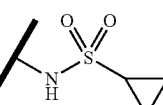 |
| 153) | 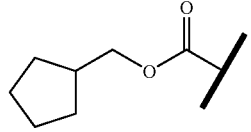 |  | 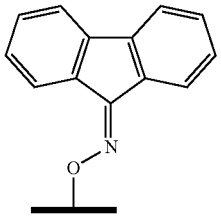 | 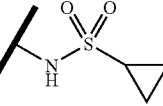 |
| 154) | 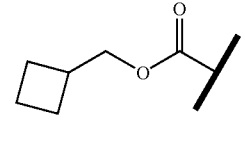 |  | 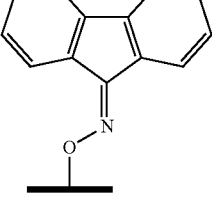 | 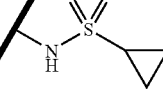 |
| 155) | 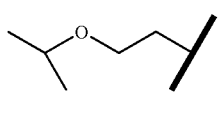 |  | 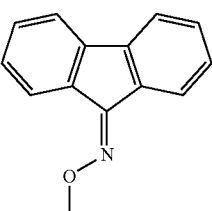 | 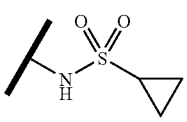 |
| 156) | 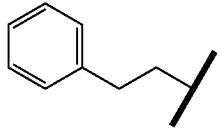 |  | 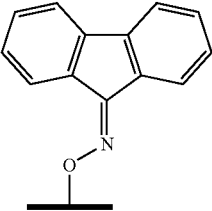 | 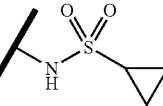 |
| 157) | 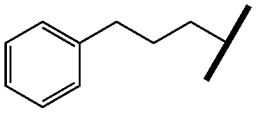 |  | 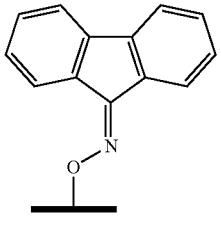 | 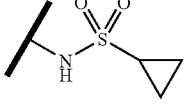 |

TABLE 2-continued
| Example | Rx | L | W | G |
|---|---|---|---|---|
| 158) | 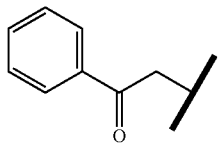 | 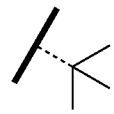 | 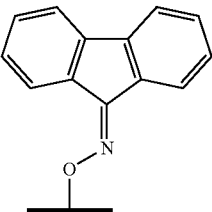 | 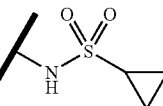 |
| 159) | 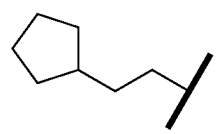 |  | 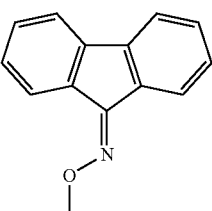 | 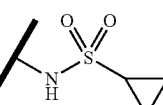 |
| 160) | 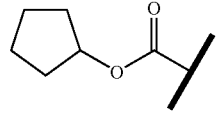 |  | 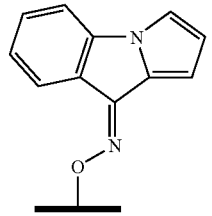 | 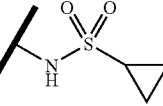 |
| 161) | 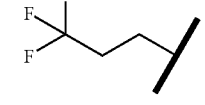 |  | 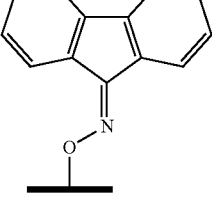 | 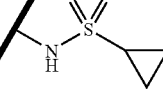 |
| 162) | 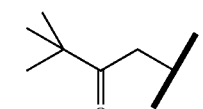 |  | 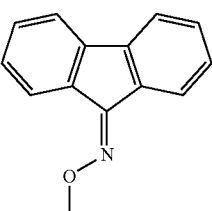 | 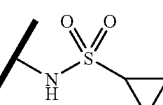 |
| 163) | 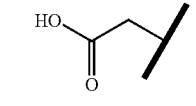 |  | 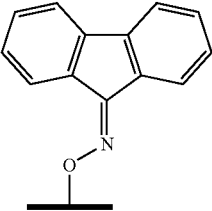 | 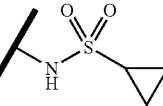 |
| 164) | 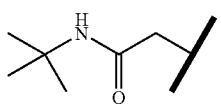 |  | 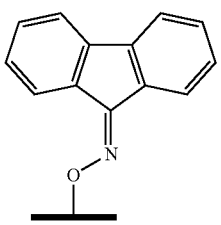 | 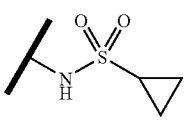 |

TABLE 2-continued
| Example | Rx | L | W | G |
|---|---|---|---|---|
| 165) | 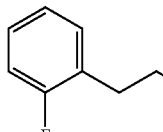 | 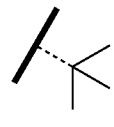 | 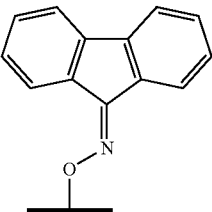 | 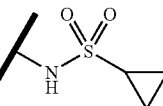 |
| 166) | 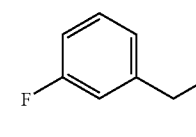 |  | 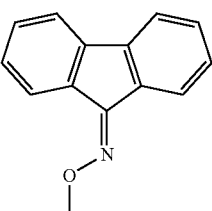 | 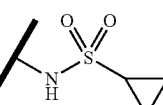 |
| 167) | 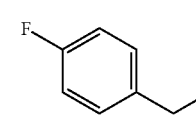 | 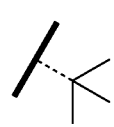 | 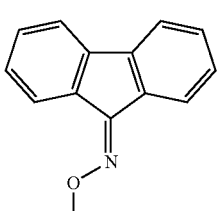 | 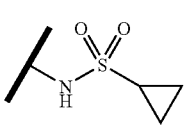 |
| 168) | 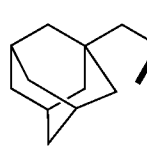 |  | 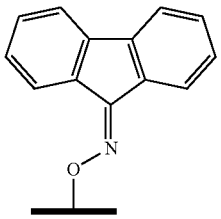 | 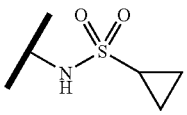 |
| 169) | 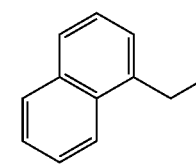 |  | 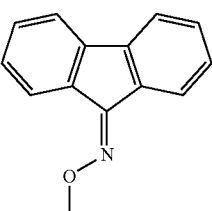 | 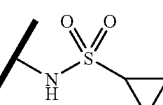 |
| 170) | 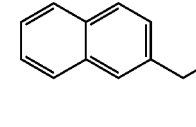 |  | 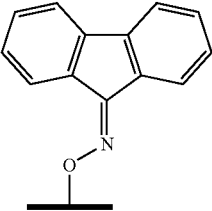 | 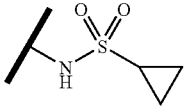 |
| 171) | 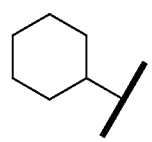 | 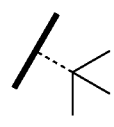 | 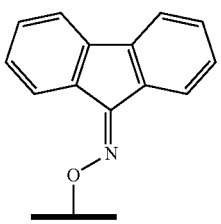 | 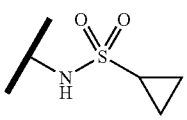 |

TABLE 2-continued

| Example | Rx | L | W | G |
|---|---|---|---|---|
| 172) | adamantyl-ethyl | C(CH3)2 | fluoren-9-ylidene-O-methyl (oxime ether) | -NHSO2-cyclopropyl |
| 173) | 2-adamantyl | C(CH3)2 | fluoren-9-ylidene-O-methyl (oxime ether) | -NHSO2-cyclopropyl |
| 174) | 2-(trifluoromethyl)phenethyl | C(CH3)2 | fluoren-9-ylidene-O-methyl (oxime ether) | -NHSO2-cyclopropyl |
| 175) | 2-methoxyphenethyl | C(CH3)2 | fluoren-9-ylidene-O-methyl (oxime ether) | -NHSO2-cyclopropyl |
| 176) | cyclopentyloxycarbonylmethyl | C(CH3)2 | (2'-fluorobiphenyl-2-yl)methylidene-O-methyl (oxime ether) | -NHSO2-cyclopropyl |
| 177) | cyclopentyloxycarbonylmethyl | C(CH3)2 | (3'-fluorobiphenyl-2-yl)methylidene-O-methyl (oxime ether) | -NHSO2-cyclopropyl |

TABLE 2-continued
| Example | Rx | L | W | G |
|---|---|---|---|---|
| 178) | 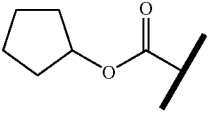 |  | 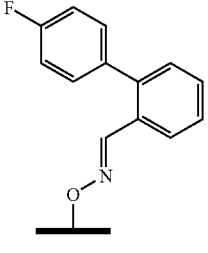 | 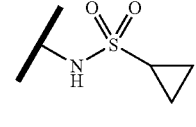 |
| 179) | 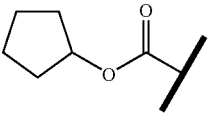 |  | 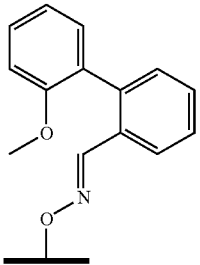 | 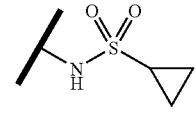 |
| 180) | 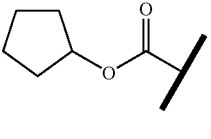 |  | 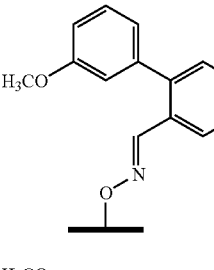 | 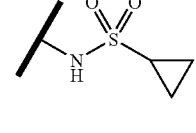 |
| 181) | 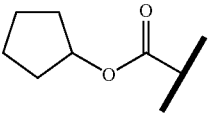 | 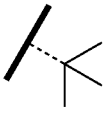 | 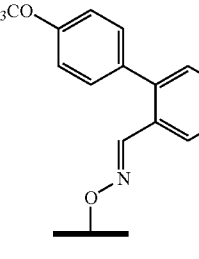 | 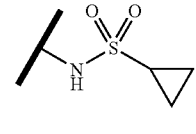 |
| 182) | 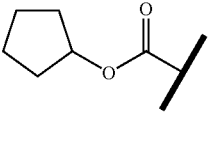 |  | 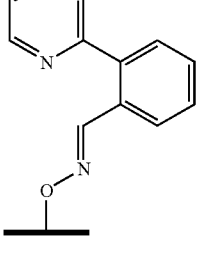 | 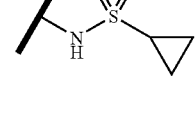 |
| 183) | 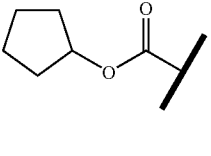 |  | 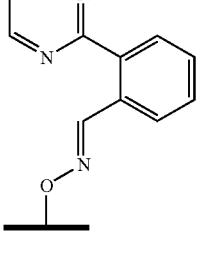 | 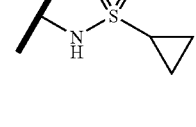 |

TABLE 2-continued
| Example | Rx | L | W | G |
|---|---|---|---|---|
| 184) | 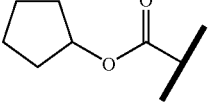 |  | 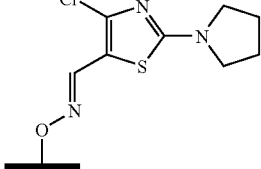 | 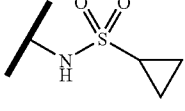 |
| 185) | 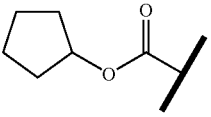 |  | 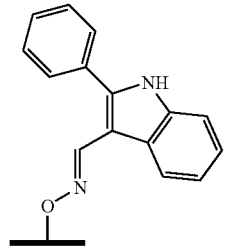 | 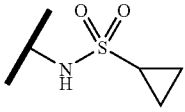 |
| 186) | 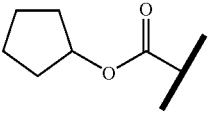 |  | 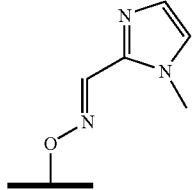 | 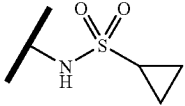 |
| 187) | 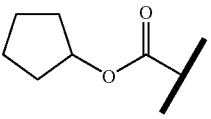 | 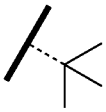 | 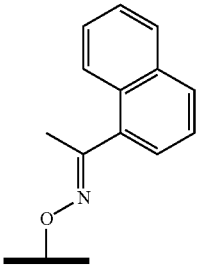 | 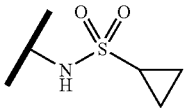 |
| 188) | 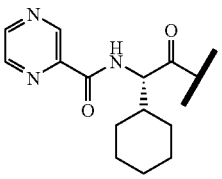 |  | 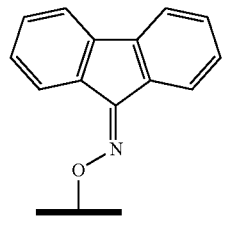 | 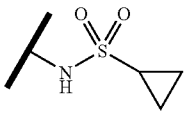 |
| 189) | 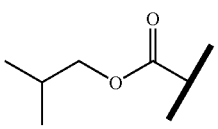 |  | 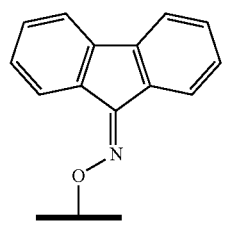 | 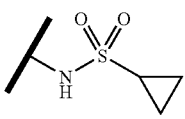 |

TABLE 2-continued
| Example | Rx | L | W | G |
|---|---|---|---|---|
| 190) | 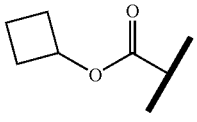 |  | 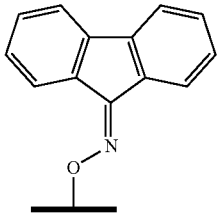 | 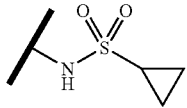 |
| 191) | 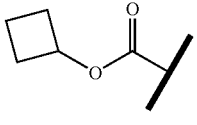 |  | 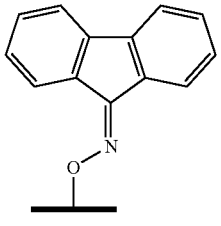 | 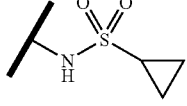 |
| 192) | 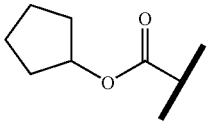 |  | 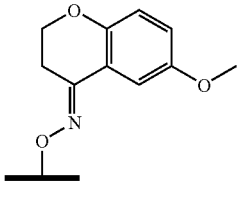 | 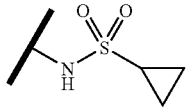 |
| 193) | 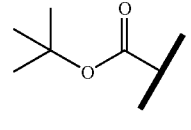 | 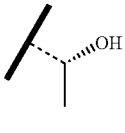 | 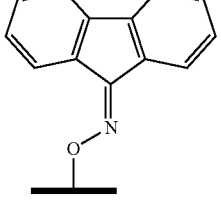 | 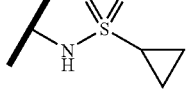 |
| 194) | 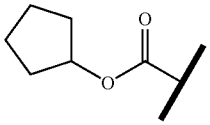 |  | 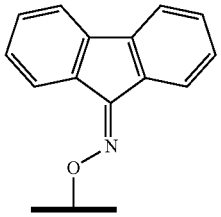 | 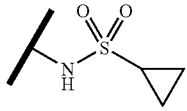 |
| 195) | 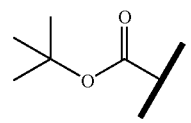 | 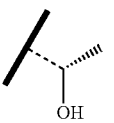 | 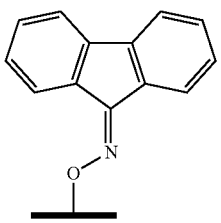 | 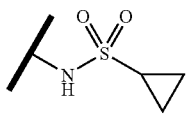 |
| 196) | 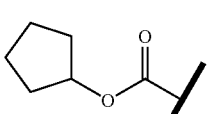 | 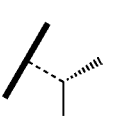 | 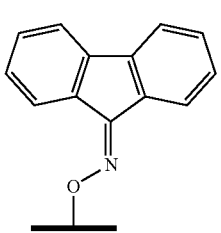 | 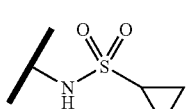 |

TABLE 2-continued
| Example | Rx | L | W | G |
|---|---|---|---|---|
| 197) | 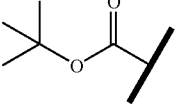 | 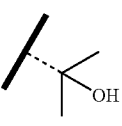 | 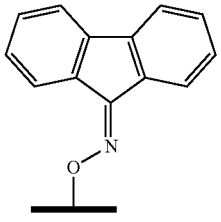 | 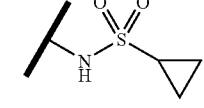 |
| 198) | 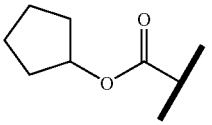 |  | 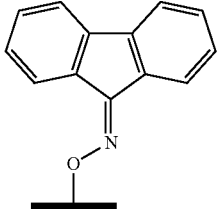 | 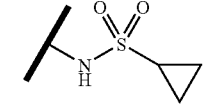 |
| 199) | 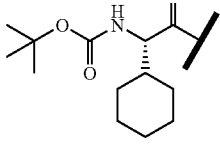 |  | 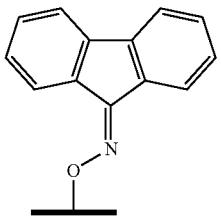 | 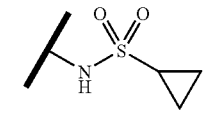 |
| 200) | 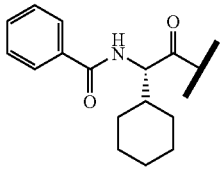 | 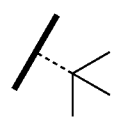 | 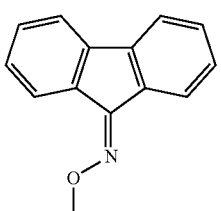 | 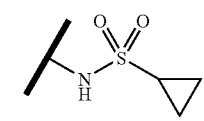 |
| 201) | 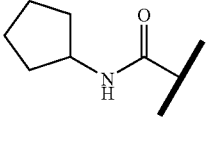 | 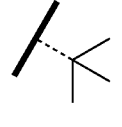 | 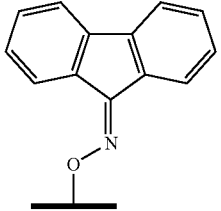 | 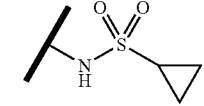 |
| 202) | 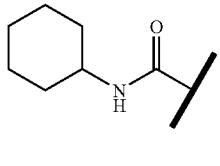 | 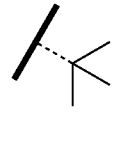 | 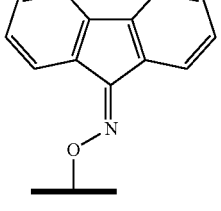 | 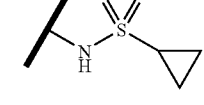 |
| 203) | 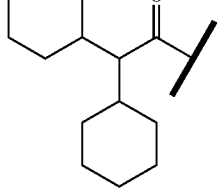 |  | 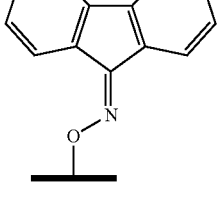 | 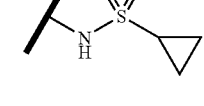 |

TABLE 2-continued
| Example | Rx | L | W | G |
|---|---|---|---|---|
| 204) | 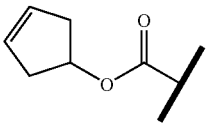 | 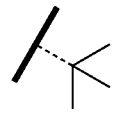 | 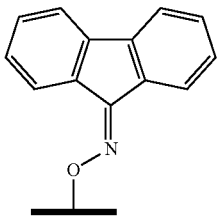 | 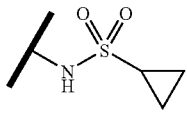 |
| 205) | 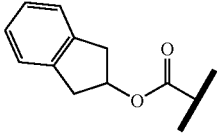 |  | 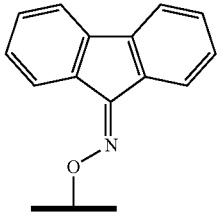 | 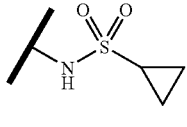 |
| 206) | 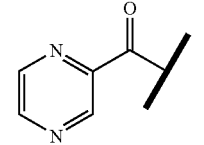 |  | 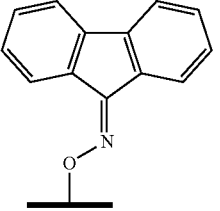 | 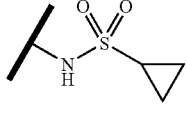 |
| 207) | 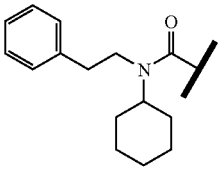 |  | 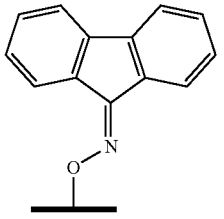 | 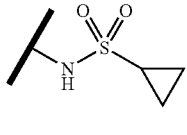 |
| 208) | 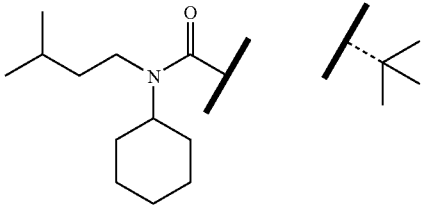 |  | 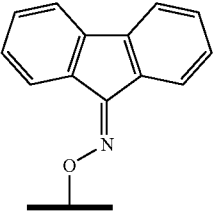 | 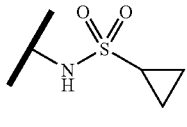 |
| 209) | 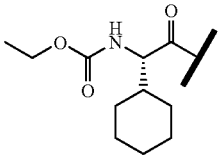 |  | 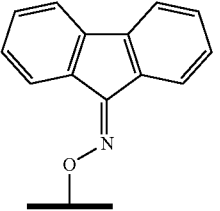 | 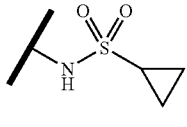 |
| 210) | 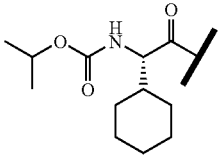 |  | 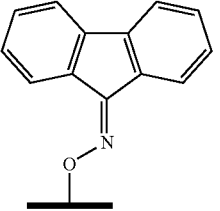 | 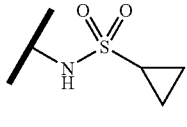 |

TABLE 2-continued

| Example | Rx | L | W | G |
|---|---|---|---|---|
| 211) | isobutyl carbamate-NH-CH(cyclohexyl)-C(=O)- | t-Bu | fluoren-9-ylidene-N-O- | -NH-S(=O)₂-cyclopropyl |
| 212) | pyrazine-2-C(=O)-N(Me)-CH(cyclohexyl)-C(=O)- | t-Bu | fluoren-9-ylidene-N-O- | -NH-S(=O)₂-cyclopropyl |
| 213) | cyclopentyl-O-C(=O)- | t-Bu | Ph-CH=N-O- | -NH-S(=O)₂-cyclopropyl |
| 214) | cyclopentyl-O-C(=O)- | t-Bu | Ph₂C=N-O- | -NH-S(=O)₂-cyclopropyl |
| 215) | cyclopentyl-O-C(=O)- | t-Bu | fluoren-9-ylidene-N-O- | -NH-S(=O)₂-(2-methylphenyl) |
| 216) | cyclopentyl-O-C(=O)- | t-Bu | fluoren-9-ylidene-N-O- | -NH-S(=O)₂-(3-chloro-4-methylphenyl) |
| 217) | cyclopentyl-O-C(=O)- | t-Bu | fluoren-9-ylidene-N-O- | -NH-S(=O)₂-(4-fluorophenyl) |

TABLE 2-continued
| Example | Rx | L | W | G |
|---|---|---|---|---|
| 218) | 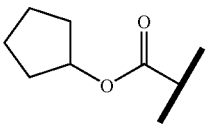 | 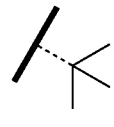 | 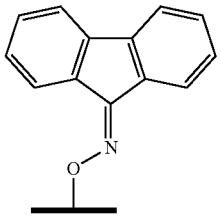 | 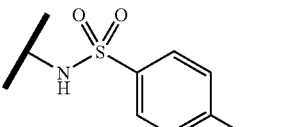 |
| 219) | 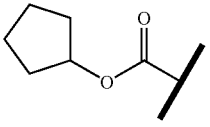 |  | 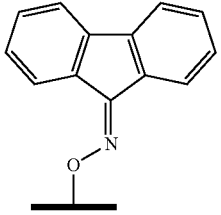 | 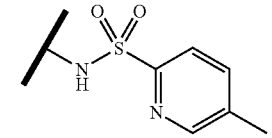 |
| 220) | 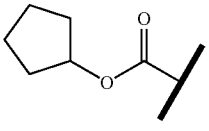 |  | 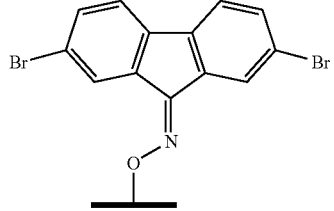 | 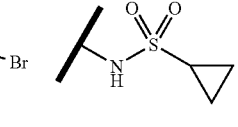 |
| 221) | 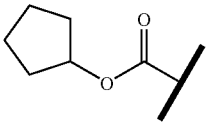 |  | 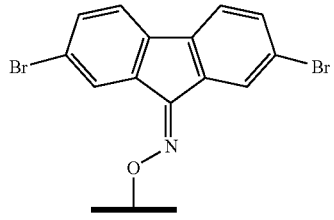 | 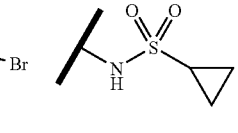 |
| 222) | 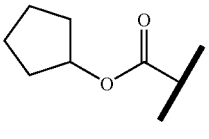 | 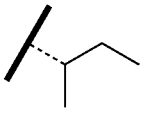 | 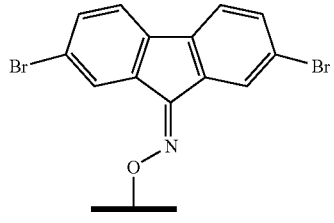 | 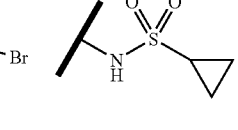 |
| 223) | 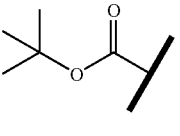 | 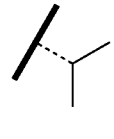 | 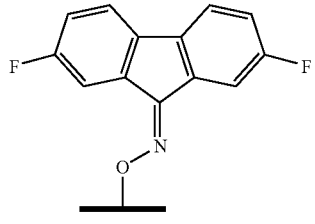 | 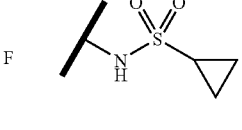 |
| 224) | 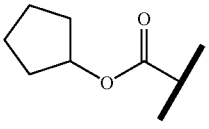 |  | 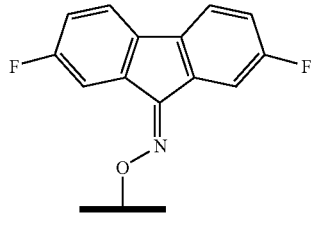 | 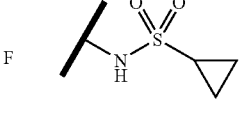 |

TABLE 2-continued

| Example | Rx | L | W | G |
|---|---|---|---|---|
| 225) | 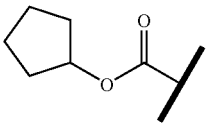 | 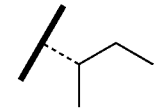 | 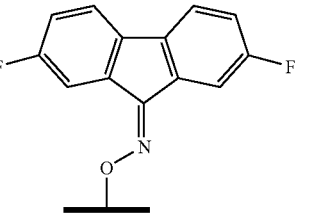 | 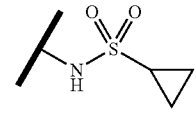 |
| 226) | 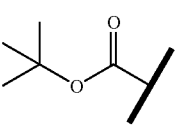 |  | 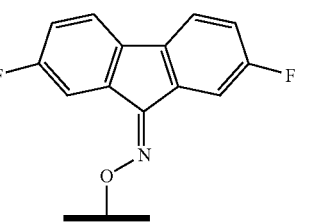 | 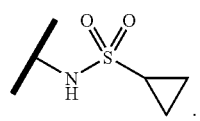 |

16. A pharmaceutical composition comprising a therapeutically effective amount of a compound according to claim 1 or a pharmaceutically acceptable salt thereof, in combination with a pharmaceutically acceptable carrier or excipient.

17. A method of treating a hepatitis C viral infection in a subject, comprising administering to the subject an inhibitory amount of a pharmaceutical composition according to claim 16.

18. A method of inhibiting the replication of hepatitis C virus, the method comprising administering a hepatitis C viral NS3 protease inhibitory amount of the pharmaceutical composition of claim 16.

19. The method of claim 17 further comprising administering concurrently an additional anti-hepatitis C virus agent.

20. The method of claim 19, wherein said additional anti-hepatitis C virus agent is selected from the group consisting of: α-interferon, β-interferon, ribavarin, and adamantine.

21. The method of claim 19, wherein said additional anti-hepatitis C virus agent is an inhibitor of hepatitis C virus helicase, polymerase, metalloprotease, or IRES.

22. The pharmaceutical composition of claim 16, further comprising another anti-HCV agent.

23. The pharmaceutical composition of claim 16, further comprising an agent selected from interferon, ribavirin, amantadine, pegylated interferon, another HCV protease inhibitor, an HCV polymerase inhibitor, an HCV helicase inhibitor, or an internal ribosome entry site inhibitor.

24. The pharmaceutical composition of claim 16, further comprising another anti-viral, anti-bacterial, anti-fungal or anti-cancer agent, or an immune modulator.

25. A process for making compounds of formula (I) comprising the steps of:

(1) coupling reaction between the oximes of formula (IX) and difluoromethyl derivatives of formula (X) or (XI);

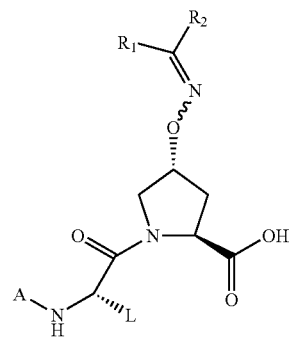

(iX)

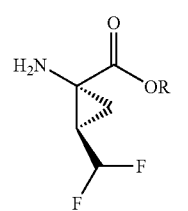

(X)

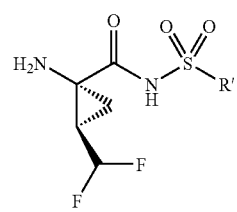

(XI)

(2) preparation of difluoromethyl derivatives of formula (X) or (XI) via fluorination of the corresponding protected amino aldehydes of formula (XII) using a flourinating agent;

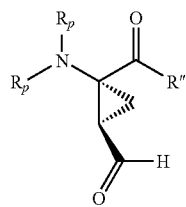
(XII)
(3) converting the ester moiety to the corresponding sulfonamide via ester hydrolysis, followed by acid coupling with sulfonamide in the presence of a coupling reagent and base.
26. The process of claim 25, wherein the fluorinating reagent is a dialkylaminosulfur trifluoride.
* * * * *

UNITED STATES PATENT AND TRADEMARK OFFICE
CERTIFICATE OF CORRECTION

PATENT NO. : 8,361,958 B2
APPLICATION NO. : 12/328433
DATED : January 29, 2013
INVENTOR(S) : Yonghua Gai et al.

It is certified that error appears in the above-identified patent and that said Letters Patent is hereby corrected as shown below:

In the Claims

At Column 133

In Claim 6, at line 59, delete "$(SO_2)OR_s$," and insert -- $(SO_2)OR_5$ --.

Signed and Sealed this
Sixteenth Day of April, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,361,958 B2 | Page 1 of 1 |
| APPLICATION NO. | : 12/328433 | |
| DATED | : January 29, 2013 | |
| INVENTOR(S) | : Gai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 874 days.

Signed and Sealed this
Eighteenth Day of November, 2014

Michelle K. Lee
*Deputy Director of the United States Patent and Trademark Office*